US012714569B2

(12) United States Patent
Forsell

(10) Patent No.: US 12,714,569 B2
(45) Date of Patent: Aug. 25, 2026

(54) HIP JOINT DEVICE AND METHOD

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 995 days.

(21) Appl. No.: 17/852,405

(22) Filed: Jun. 29, 2022

(65) Prior Publication Data

US 2022/0323228 A1 Oct. 13, 2022

Related U.S. Application Data

(62) Division of application No. 13/383,264, filed as application No. PCT/SE2010/050833 on Jul. 12, 2010, now abandoned.

(Continued)

(30) Foreign Application Priority Data

Jul. 10, 2009 (SE) .................................... 0900957-2
Jul. 10, 2009 (SE) .................................... 0900958-0
Jul. 10, 2009 (SE) .................................... 0900959-8
Jul. 10, 2009 (SE) .................................... 0900960-6
Jul. 10, 2009 (SE) .................................... 0900962-2
Jul. 10, 2009 (SE) .................................... 0900963-0
Jul. 10, 2009 (SE) .................................... 0900965-5
Jul. 10, 2009 (SE) .................................... 0900966-3
Jul. 10, 2009 (SE) .................................... 0900968-9
Jul. 10, 2009 (SE) .................................... 0900969-7
Jul. 10, 2009 (SE) .................................... 0900970-5

(Continued)

(51) Int. Cl.
*A61F 2/34* (2006.01)
*A61F 2/32* (2006.01)

(Continued)

(52) U.S. Cl.
CPC .................. *A61F 2/34* (2013.01); *A61F 2/32* (2013.01); *A61F 2/3609* (2013.01); (Continued)

(58) Field of Classification Search
CPC ...... A61F 2002/3443; A61F 2002/3483; A61F 2002/3615
See application file for complete search history.

(56) References Cited

U.S. PATENT DOCUMENTS 6,413,280 B1 * 7/2002 Feiler ........................ A61F 2/32 623/22.21
2008/0228283 A1 * 9/2008 Willi ..................... A61F 2/3609 623/23.35
2011/0054628 A1 * 3/2011 Banks ....................... A61F 2/32 623/22.35

FOREIGN PATENT DOCUMENTS

EP 1421919 A1 * 5/2004 ............... A61F 2/32

* cited by examiner

*Primary Examiner* — Megan Y Wolf

(57) ABSTRACT

A medical device for implantation in a hip joint of a patient, the natural hip joint having a ball shaped caput femur integrated with a collum femur having a collum and caput center axis, extending longitudinal along the collum and caput femur, in the center thereof, as the proximal part of the femoral bone with a convex hip joint surface towards the centre of the hip joint and a bowl shaped acetabulum as part of the pelvic bone with a concave hip joint surface towards the centre of the hip joint, the medical device comprising; an artificial caput femur comprising a convex surface towards the centre of the hip joint, an elongated portion adapted to be connected to a prosthetic spherical portion of said artificial convex caput femur and fixated to the pelvic bone of the human patient.

16 Claims, 40 Drawing Sheets

Related U.S. Application Data

(60) Provisional application No. 61/229,755, filed on Jul. 30, 2009, provisional application No. 61/229,789, filed on Jul. 30, 2009, provisional application No. 61/229,735, filed on Jul. 30, 2009, provisional application No. 61/229,738, filed on Jul. 30, 2009, provisional application No. 61/229,761, filed on Jul. 30, 2009, provisional application No. 61/229,767, filed on Jul. 30, 2009, provisional application No. 61/229,778, filed on Jul. 30, 2009, provisional application No. 61/229,786, filed on Jul. 30, 2009, provisional application No. 61/229,746, filed on Jul. 30, 2009, provisional application No. 61/229,748, filed on Jul. 30, 2009, provisional application No. 61/229,743, filed on Jul. 30, 2009, provisional application No. 61/229,796, filed on Jul. 30, 2009, provisional application No. 61/229,747, filed on Jul. 30, 2009, provisional application No. 61/229,752, filed on Jul. 30, 2009, provisional application No. 61/229,739, filed on Jul. 30, 2009, provisional application No. 61/229,745, filed on Jul. 30, 2009, provisional application No. 61/229,751, filed on Jul. 30, 2009.

(30) Foreign Application Priority Data

Jul. 10, 2009 (SE) .................................... 0900972-1
Jul. 10, 2009 (SE) .................................... 0900973-9
Jul. 10, 2009 (SE) .................................... 0900974-7
Jul. 10, 2009 (SE) .................................... 0900976-2
Jul. 10, 2009 (SE) .................................... 0900978-8
Jul. 10, 2009 (SE) .................................... 0900981-2

(51) Int. Cl.
*A61F 2/36* (2006.01)
*A61F 2/30* (2006.01)
*A61F 2/46* (2006.01)

(52) U.S. Cl.
CPC ............... *A61F 2002/30125* (2013.01); *A61F 2002/30153* (2013.01); *A61F 2002/30154* (2013.01); *A61F 2002/30166* (2013.01); *A61F 2002/30179* (2013.01); *A61F 2002/305* (2013.01); *A61F 2002/30578* (2013.01); *A61F 2002/3085* (2013.01); *A61F 2002/3241* (2013.01); *A61F 2002/3443* (2013.01); *A61F 2002/3483* (2013.01); *A61F 2002/3615* (2013.01); *A61F 2002/3625* (2013.01); *A61F 2002/4631* (2013.01)

Fig. 2d
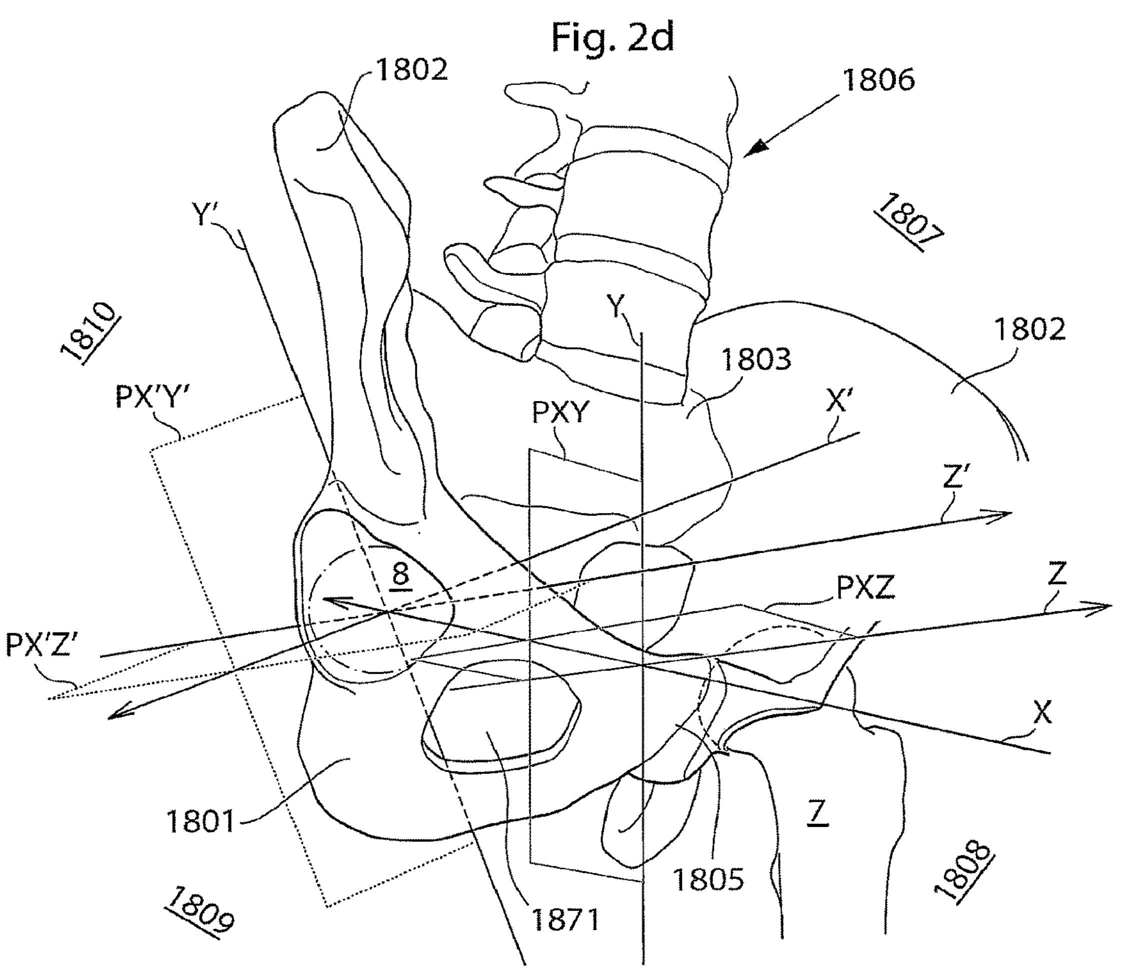
Fig. 2e
Fig. 2f
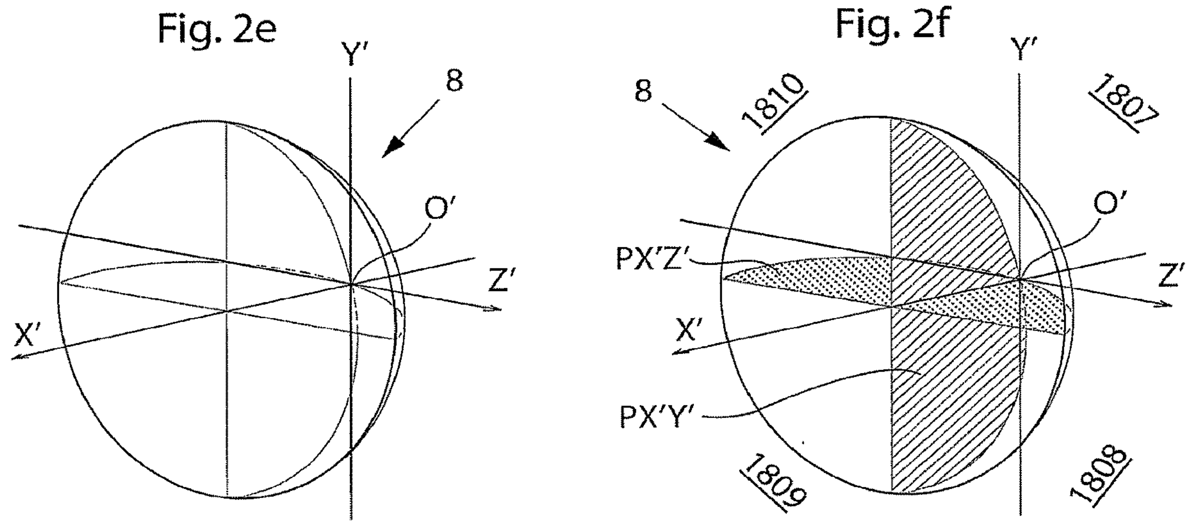

102
109
602
109c
109b
6
7

Fig. 6a
102
121
601
121
602
6
110
7
109
Fig. 6b
680
102
110
601
602
6
680
7
109
Fig. 6c
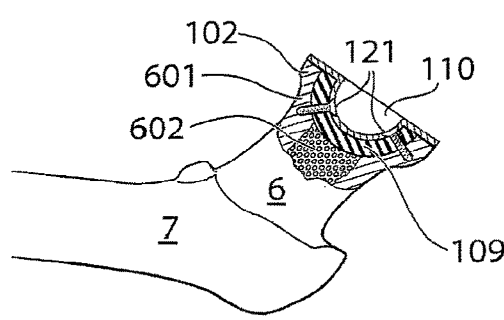
Fig. 6d
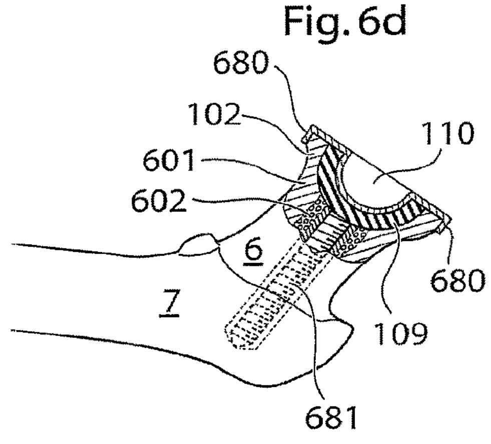
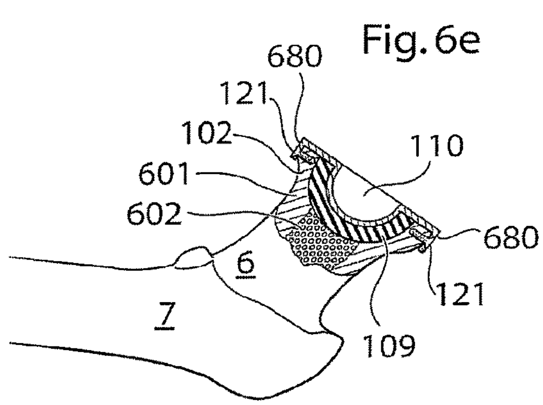

110
682
680
680

110
680
680
683
683

110
680
680
680
110
680
121
121
680
110
680
121b
121b 110
121
121
110

121
110
121
110

692
620
685
110
680
680
121
121
620
681
685

Fig. 9
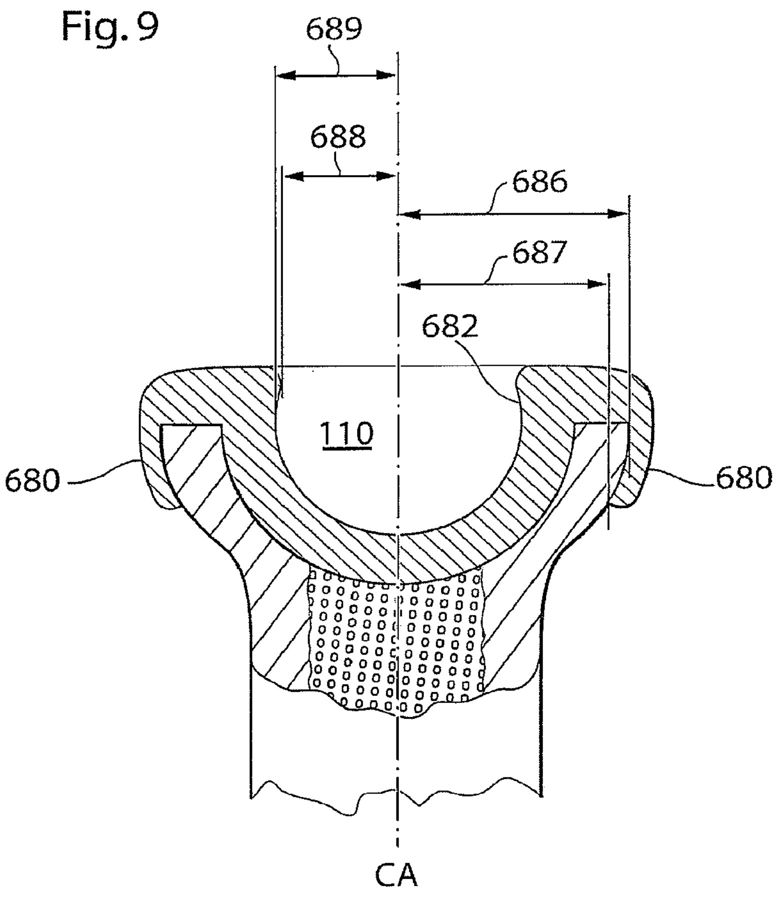
Fig.10a
688
690
Fig.10b
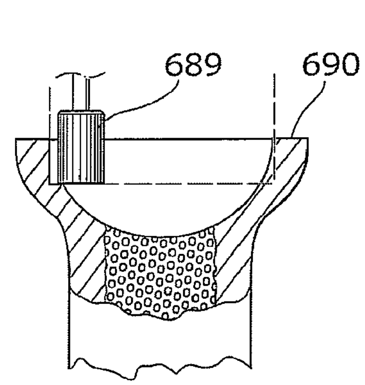

Fig.17a
CX
45
2201
Fig.17b
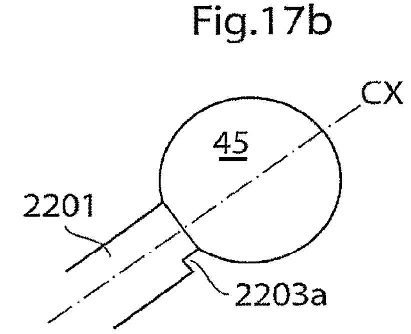
Fig.17c
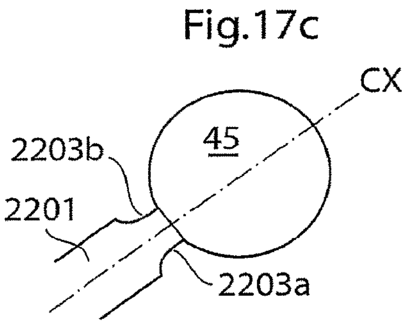
Fig.17d
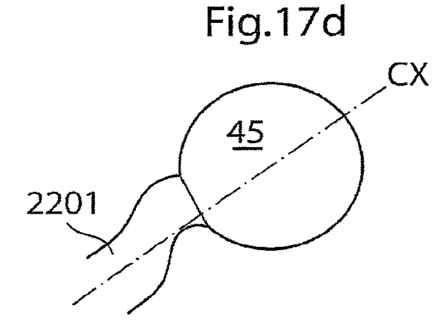
Fig.18
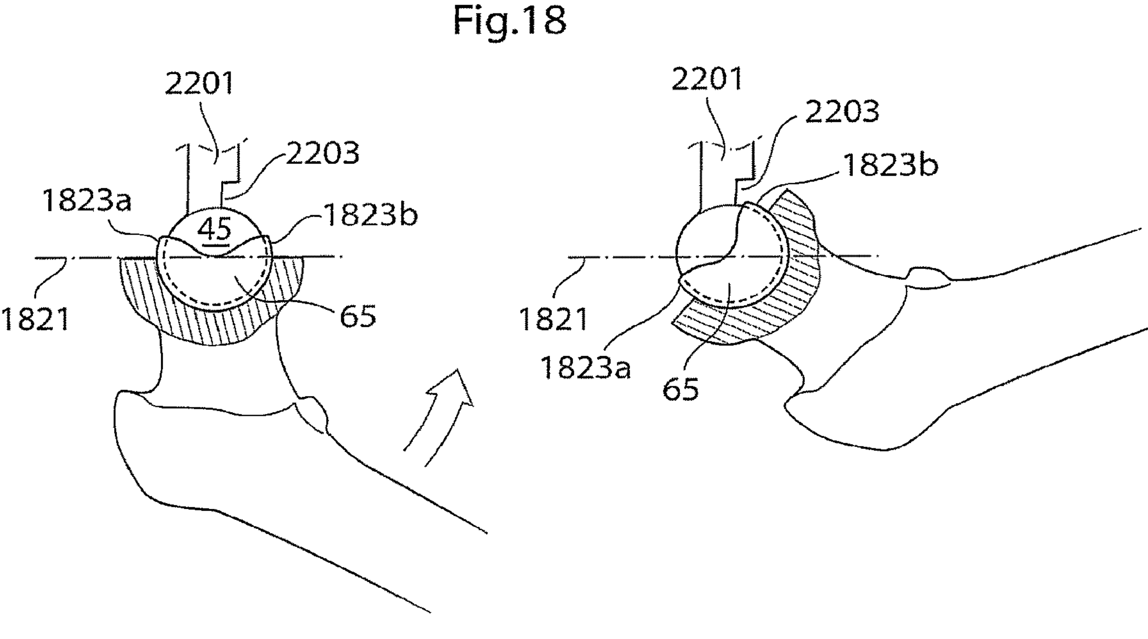

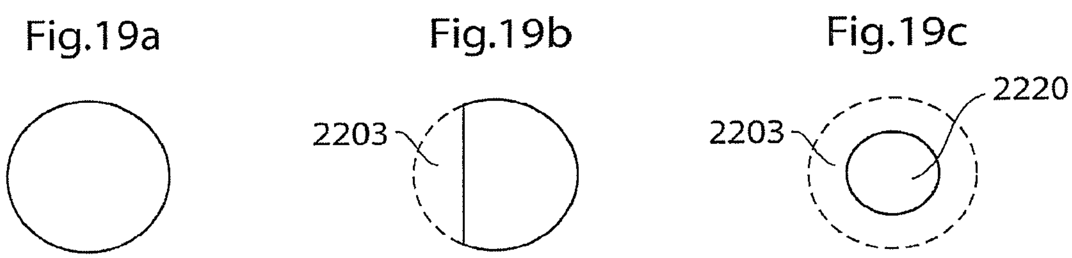
Fig.19a
Fig.19b
2203
Fig.19c
2203
2220
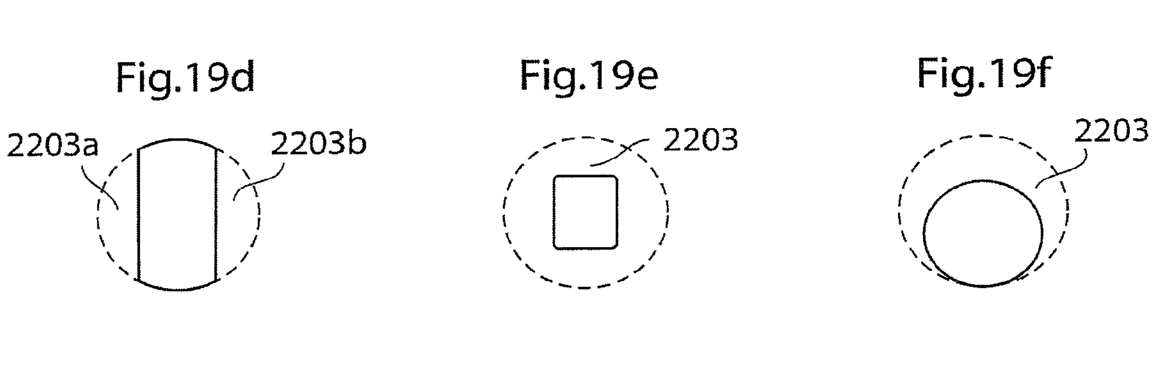
Fig.19d
2203a
2203b
Fig.19e
2203
Fig.19f
2203
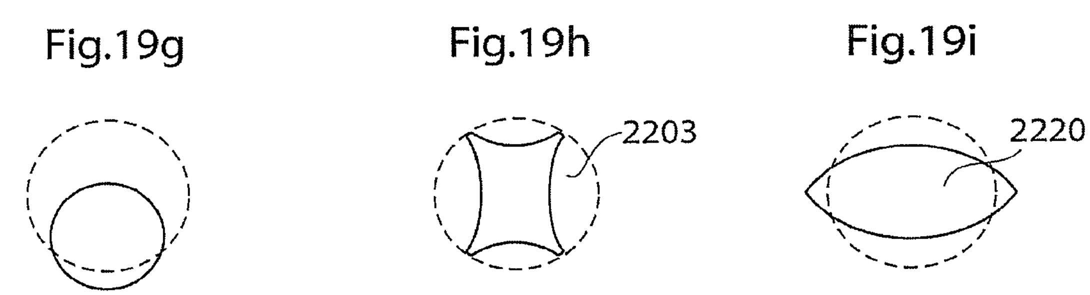
Fig.19g
Fig.19h
2203
Fig.19i
2220
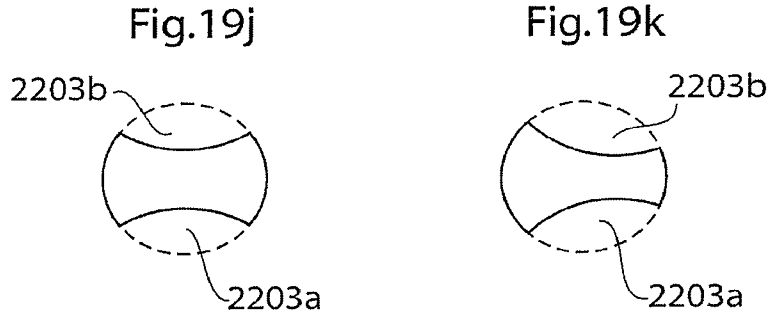
Fig.19j
2203b
2203a
Fig.19k
2203b
2203a Fig.20a
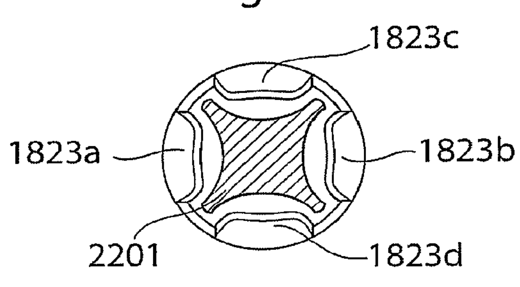
65
1823a
1823b
1823c
45
2201
Fig.20b
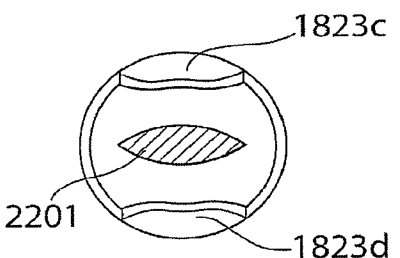
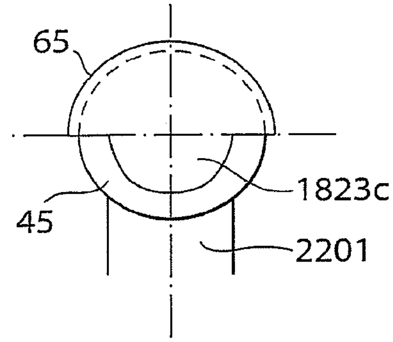
Fig.20c
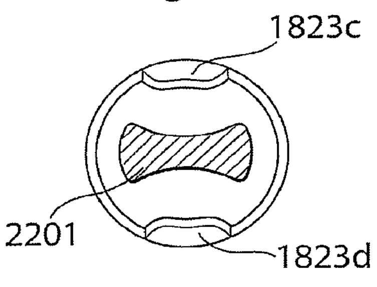
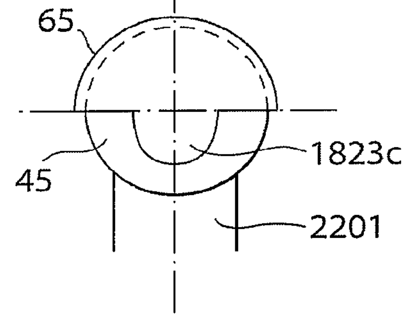
Fig.20d
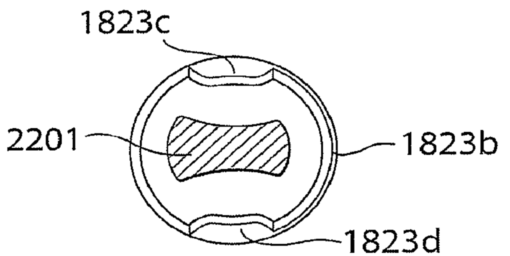
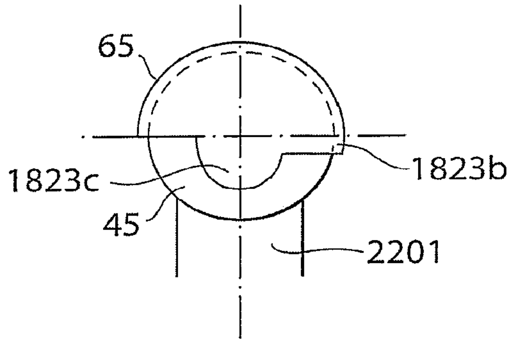

Fig.34a
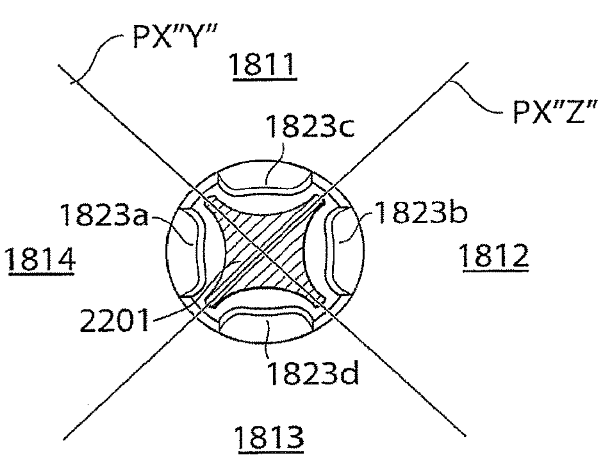
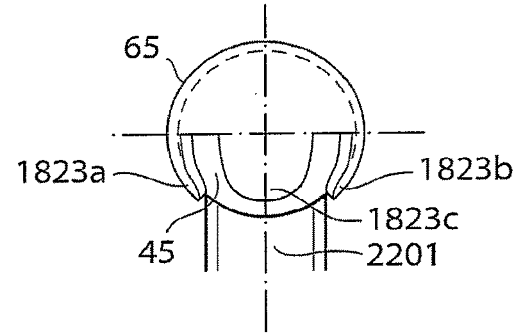
Fig.34b
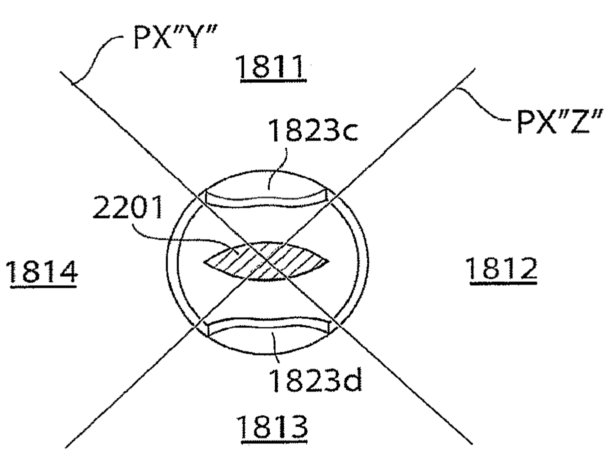
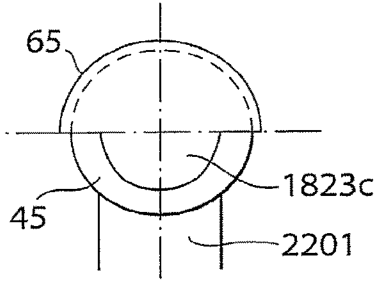

Fig.34c
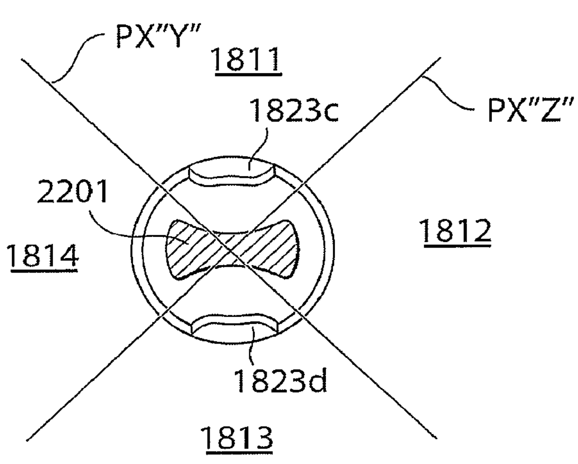
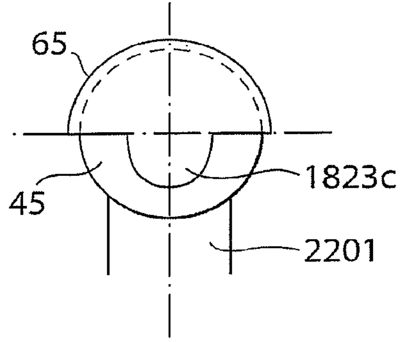
Fig.34d
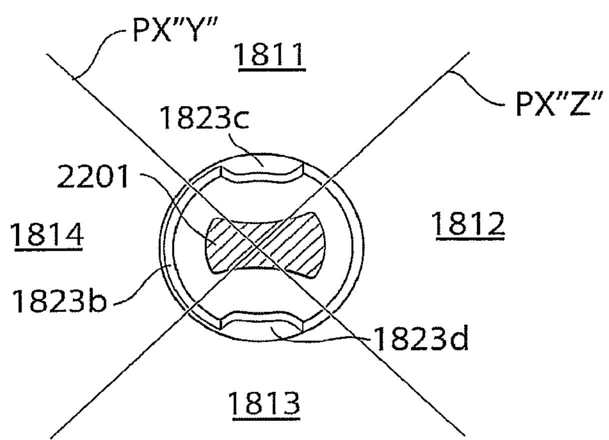
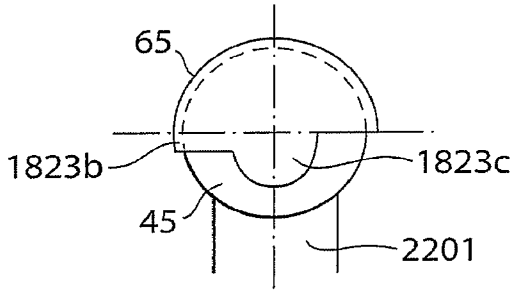

HIP JOINT DEVICE AND METHOD

This application is a divisional application of the U.S. application Ser. No. 13/383,264 filed on Jan. 10, 2012 which is the U.S national phase of International application No. PCT/SE2010/050833, filed 12 Jul. 2010, which designated U.S. and claims the benefit of U.S. Provisional Nos. 61/229,738, 61/229,739, 61/229,743, 61/229,745, 61/229,746, 61/229,747, 61/229,748, 61/229,751, 61/229,752, 61/229,755, 61/229,761, 61/229,767, 61/229,778, 61/229,786, 61/229,789, 61/229,796, 61/229,735, all filed on 30 Jul. 2009, and which further claims priority from Swedish Application Nos: 900958-0, 0900978-8, 0900976-2, 0900974-7, 0900973-9, 0900972-1, 0900970-5, 0900969-7, 0900968-9, 0900966-3, 0900965-5, 0900963-0, 0900962-2, 0900960-6, 0900959-8, 0900957-2, 0900981-2, all filed on 10 Jul. 2009.

FIELD OF INVENTION

The present invention relates generally to a medical device for implantation in a hip joint, and a method of providing said medical device.

BACKGROUND

The hip joint is a synovial joint, joining the pelvis to the proximal portion of the femoral bone. Synovial joints are the most common types of joints in mammals, and are typical of nearly all limb joints. The contacting surfaces of said the pelvic, the acetabulum, and the contacting surface of the femoral bone, the caput femur, are smooth and rounded, and covered by articular cartilage. A synovial membrane, encapsulates the joint, forming a hip joint cavity, which contains synovial fluid. Outside the synovial membrane is a fibrous capsule and ligaments, forming an articular capsule.

There are both natural and pathological processes leading to deteriorated joint function. With age and wear, the articular cartilage becomes less effective as a shock absorber and a lubricated surface. Different degenerative joint diseases, such as arthritis, osteoartrithis, or osteoarthrosis, accelerate the deterioration.

Hip joint Osteoarthritis is a syndrome in which low-grade inflammation results in pain in the hip joints, caused by abnormal wearing of the Cartilage that acts as a cushion inside if the hip joint. This abnormal wearing of the cartilage also results in a decrease of the joints lubricating fluid called Synovial fluid. Hip joint Osteoarthritis is estimated to affect 80% of all people over 65 years of age, in more or less serious forms.

The present treatment for hip osteoarthritis comprises NSAID drugs, local injections of Hyaluronic acid or Glucocorticoid to help lubricating the hip joint, and replacing parts of the hip joint with a prosthesis through hip joint surgery.

The replacing of parts of the hip joint is one of the most common surgeries to date performed at hundreds of thousands of patients in the world every year. The most common method comprises placing a metal prosthesis in Femur and a plastic bowl in Acetabulum. This operation is usually done through a lateral incision in the hip and upper thigh and through, Fascia Lata and the lateral muscles of the thigh. To get access to the hip joint, the supporting hip joint capsule attached to Femur and Ilium of Pelvis needs to be penetrated, making it difficult to get a fully functional joint after the surgery. Femur is then cut at the neck with a bone saw and the prosthesis is placed in femur either with bone cement or without. Acetabulum is slightly enlarged using an Acetabular reamer, and the plastic bowl is positioned using screws or bone cement. The complications after hip joint surgery includes dislocation of the hip joint and loosening of the prosthesis from its fixation in the femoral bone. The loosening and/or dislocation of the prosthesis could be induced by an abnormal strain being placed on the hip joint from e.g. the patient falling or making a rapid movement of the hip, or by a bodily macrophage reaction.

The surgery typically requires one week of hospitalization due to the increased risk of infection. The recovery process is on average about 6 weeks, but even after this period the patient should not perform any physical activates that places large strain on the joint.

SUMMARY

According to one embodiment of a medical device for implantation in a hip joint of a patient, the natural hip joint having a ball shaped caput femur integrated with a collum femur having a collum and caput center axis, extending longitudinal along the collum and caput femur, in the center thereof, as the proximal part of the femoral bone with a convex hip joint surface towards the centre of the hip joint and a bowl shaped acetabulum as part of the pelvic bone with a concave hip joint surface towards the centre of the hip joint, the medical device comprising; an artificial caput femur comprising a convex surface towards the centre of the hip joint, an elongated portion adapted to be connected to a prosthetic spherical portion of said artificial convex caput femur and fixated to the pelvic bone of the human patient, said artificial convex caput femur is adapted to, when implanted, be fixated to the pelvic bone of the human patient through said elongated portion fixation to the pelvic bone, and be in movable connection with a prosthetic artificial acetabulum surface fixated to the femoral bone of the patient, comprising at least one extending portion adapted to clasp said prosthetic spherical portion, wherein said elongated portion comprises a restricting portion adapted to restrict the motion range of the artificial acetabulum in relation to said artificial convex caput femur, and wherein said restricting portion of said elongated portion is adapted to enable an advantageous motion range in relation to said artificial acetabulum.

According to one embodiment, said elongated portion comprises at least one recess adapted to receive a portion of said prosthetic artificial acetabulum, when implanted.

According to one embodiment, said recess is adapted to be placed frontal to the coronal pelvis plane, when implanted and being in the base position.

According to one embodiment, said recess is adapted to be placed in the frontal quadrant, when implanted and being in the base position.

According to one embodiment, said recess is adapted to be placed in the dorsal quadrant, when implanted and being in the base position.

According to one embodiment, said recess is adapted to be placed in the proximal quadrant, when implanted and being in the base position.

According to one embodiment, said recess is adapted to be placed in the distal quadrant, when implanted.

According to one embodiment, said recesses is more than 2 mm deep.

According to one embodiment, said recesses is more than 4 mm deep.

According to one embodiment, said recesses is more than 6 mm deep.

According to one embodiment, said recesses is more than 8 mm deep.

According to one embodiment, said elongated portion comprises an adaptation adapted to receive said extending portion when implanted.

According to one embodiment, said adaptation comprises a bent portion of said elongated portion.

According to one embodiment, said bent portion is bent such that said restricting portion of said elongated portion mainly is placed frontal to the coronal pelvis plane, when implanted and being in the base position.

According to one embodiment, said bent portion is bent such that said restricting portion of said elongated portion mainly is placed dorsal to the coronal pelvis plane, when implanted and being in the base position.

According to one embodiment, said bent portion is bent such that said restricting portion of said elongated portion mainly is placed in the frontal quadrant, when implanted and being in the base position.

According to one embodiment, said bent portion is bent such that said restricting portion of said elongated portion mainly is placed in the dorsal quadrant, when implanted and being in the base position.

According to one embodiment, said bent portion is bent such that said restricting portion of said elongated portion mainly is placed in the proximal quadrant, when implanted and being in the base position.

According to one embodiment, said bent portion is bent such that said restricting portion of said elongated portion mainly is placed in the distal quadrant, when implanted and being in the base position.

According to one embodiment, a cross-section of said restricting portion of said elongated portion, perpendicular to the caput and collum center axis, comprises a first distance and a second distance, wherein a center point of a line of said first distance intersects a center point of a line of said second distance, and wherein said first distance is shorter than said second distance. According to one embodiment, said first distance is a cross-sectional distance of a narrow portion if said elongated portion, and wherein said second distance is a cross-sectional distance of a wide portion of said elongated member. According to one embodiment, said restricting portion of said elongated portion is adapted to be substantially aligned with said collum center axis and adapted to be eccentrically placed in relation to said collum axis, when implanted. According to one embodiment, a major portion of said restricting portion of said elongated portion is adapted to be placed frontal to the coronal pelvis plane when implanted.

According to one embodiment, the restricting portion of the elongated portion is adapted to be placed in the frontal quadrant, when implanted.

According to one embodiment, the restricting portion of the elongated portion is adapted to be placed in the dorsal quadrant, when implanted.

According to one embodiment, the restricting portion of the elongated portion is adapted to be placed in the proximal quadrant, when implanted.

According to one embodiment, the restricting portion of the elongated portion is adapted to be placed in the distal quadrant, when implanted.

According to one embodiment, a cross section of the restricting portion of the elongated portion, perpendicular to the collum center axis, is circular.

According to one embodiment, a cross section of the restricting portion of the elongated portion, perpendicular to the collum center axis, is polygonal.

According to one embodiment, a cross section of the restricting portion of the elongated portion, perpendicular to the collum center axis, is elliptical.

According to one embodiment, said restricting portion, when implanted, is adapted to be placed such that adduction is restricted more degrees than flexion.

According to one embodiment, said restricting portion, when implanted, is adapted to be placed such that abduction is restricted more degrees than flexion.

According to one embodiment, said restricting portion, when implanted, is adapted to be placed such that adduction is restricted more degrees than extension.

According to one embodiment, said restricting portion, when implanted, is adapted to be placed such that abduction is restricted more degrees than extension.

According to one embodiment, a medical device system comprises a medical device according to any one of embodiments 1-34 and a prosthetic replacement for the acetabulum comprises at least one extending portion adapted to clasp said spherical portion.

According to one embodiment, said prosthetic replacement for the acetabulum comprises an inner and an outer surface, wherein a contacting portion, of said inner surface is spherical and adapted to face the center of the hip joint when said medical device is implanted, and wherein said prosthetic replacement for the acetabulum is adapted to receive said spherical portion, wherein said prosthetic replacement for the acetabulum comprises at least one extending portion, extending said contacting portion of said inner surface such that said at least one extending portion clasps said spherical portion, such that said spherical portion is restrained in said medical device, and wherein said prosthetic replacement for the acetabulum is adapted to be fixated to the femoral bone of the patient.

According to one embodiment, said prosthetic replacement for the acetabulum is adapted to receive said spherical portion being in connection with said medical device, wherein:

said inner surface comprises an equator line, being the largest circular circumference of said inner contacting surface, being a surface adapted to be in contact with said spherical portion, and said at least one extending portion passes beyond said equator line, such that the end portion of said contacting portion of said inner surface forms a circular extension line having a smaller circumference than said equator line, and said at least one extending portion circumferentially extends discontinuously along said equator line, such that a portion of said medical device can be placed between said extension line and said equator line.

According to one embodiment, said extension line is placed proximal to the equator line, when the medical device is implanted.

According to one embodiment, said at least one extending portion extends circumferentially along said equator line, dorsal to the right-left axis of pelvis when being in the base position.

According to one embodiment, said at least one extending portion extends circumferentially along said equator line, dorsal to the coronal pelvis plane PXY and proximal to the horizontal pelvis PXZ plane when being in the base position.

According to one embodiment, said at least one extending portion extends circumferentially along said equator line, dorsal to the coronal pelvis plane PXY and distal to the horizontal pelvis PXZ plane when being in the base position.

According to one embodiment, at least one first extending portion extends circumferentially along said equator line dorsal to the coronal pelvis plane PXY and proximal to the horizontal pelvis PXZ plane, and at least one second extending portion extends dorsal to the coronal pelvis plane PXY and distal to the horizontal pelvis PXZ plane when being in the base position.

According to one embodiment, said at least one extending portion extends circumferentially along said equator line, in the proximal quadrant of the equator line when being in the base position.

According to one embodiment, said at least one extending portion extends circumferentially along said equator line, in the distal quadrant of the equator line when being in the base position.

According to one embodiment, two extending portions extends circumferentially along said equator line, in the distal and proximal quadrant thereof when being in the base position.

According to one embodiment, said at least one extending portion extends circumferentially along said equator line, in the proximal and dorsal quadrant thereof when being in the base position.

According to one embodiment, said at least one extending portion extends circumferentially along said equator line, in the distal and dorsal quadrant thereof when being in the base position.

According to one embodiment, at least one extending portion extends circumferentially along said equator line, in the distal, dorsal and proximal quadrant thereof when being in the base position.

According to one embodiment, at least a first portion of said prosthetic replacement for the acetabulum is an extending portion, extending beyond said circular equator line, and at least a second portion is a portion not extending beyond said circular equator line, wherein said second portion circumferentially extends along at least ¼ of said circular equator line.

According to one embodiment, at least a first portion of said prosthetic replacement for the acetabulum is an extending portion, extending beyond said circular equator line, and at least a second portion is a portion not extending beyond said circular equator line, wherein said second portion circumferentially extends along at least ⅓ of said circular equator line.

According to one embodiment, at least a first portion of said prosthetic replacement for the acetabulum is an extending portion, extending beyond said circular equator line, and at least a second portion is a portion not extending beyond said circular equator line, wherein said second portion circumferentially extends along at least ½ of said circular equator line.

According to one embodiment, at least a first portion of said prosthetic replacement for the acetabulum is an extending portion, extending beyond said circular equator line, and at least a second portion is a portion not extending beyond said circular equator line, wherein said first portion circumferentially extends along at least ¼ of said circular equator line.

According to one embodiment, at least a first portion of said prosthetic replacement for the acetabulum is an extending portion, extending beyond said circular equator line, and at least a second portion is a portion not extending beyond said circular equator line, wherein said first portion circumferentially extends along at least ⅓ of said circular equator line.

According to one embodiment, at least a first portion of said prosthetic replacement for the acetabulum is an extending portion, extending beyond said circular equator line, and at least a second portion is a portion not extending beyond said circular equator line, wherein said first portion circumferentially extends along at least ½ of said circular equator line.

According to one embodiment, at least a first portion of said prosthetic replacement for the acetabulum is an extending portion, extending beyond said circular equator line, and at least a second portion is a portion not extending beyond said circular equator line, wherein said first portion circumferentially extends along at least 1/10 of said circular equator line.

According to one embodiment, at least a first portion of said prosthetic replacement for the acetabulum is an extending portion, extending beyond said circular equator line, and at least a second portion is a portion not extending beyond said circular equator line, wherein said first portion circumferentially extends along at least 1/10 of said circular equator line, and said second portion circumferentially extends along at least ¼ of said circular equator line.

According to one embodiment, at least two first portions of said prosthetic replacement for the acetabulum are extending portions, extending beyond said circular equator line, and at least a second portion is a portion not extending beyond said circular equator line, wherein said first portions each circumferentially extends along at least 1/10 of said circular equator line, and said second portion circumferentially extends along at least ¼ of said circular equator line.

According to one embodiment, at least two first portions of said medical device are extending portions, extending beyond said circular equator line, and wherein one of said extending portions extends further than the other extending portion.

According to one embodiment, said medical device further comprises two second portions not extending beyond said circular equator line, and wherein said two first extending portion circumferentially extends along said equator line between said two second portions.

According to one embodiment, said extending portion adapted to clasp said spherical portion and said restricting portion of said elongated portion of said medical device is adapted to, when implanted in said base position, be placed such that their placement in relation to each other creates an advantageous motion range.

According to one embodiment, said extending portion said restricting portion of said elongated portion is adapted to be placed in relation to each other when implanted in said base position, such that adduction is restricted more degrees than flexion.

According to one embodiment, said extending portion said restricting portion of said elongated portion is adapted to be placed in relation to each other when implanted in said base position, such that abduction is restricted more degrees than flexion.

According to one embodiment, said extending portion said restricting portion of said elongated portion is adapted to be placed in relation to each other when implanted in said base position, such that adduction is restricted more degrees than extension.

According to one embodiment, said extending portion said restricting portion of said elongated portion is adapted to be placed in relation to each other when implanted in said base position, such that abduction is restricted more degrees than extension.

The artificial hip joint surface, according to any of the embodiments above may comprise an artificial convex caput femur or an artificial convex caput femur surface or an artificial concave acetabulum or an artificial concave acetabulum surface.

A surgical and/or laparoscopic and/or arthroscopic method of implanting the medical device is further provided, the method comprising the steps of: cutting the skin of the patient, dissecting an area of the pelvic bone, fixating the medical device to the pelvic bone such that the medical device is in movable connection with a prosthetic artificial acetabulum surface fixated to the femoral bone of the patient and that the restricting portion of the elongated portion is placed such to enable an advantageous motion range in relation to said artificial acetabulum.

The restricting portion of said elongated portion is placed, such that adduction is restricted more degrees than flexion.

The restricting portion of said elongated portion is placed, such that abduction is restricted more degrees than flexion.

The restricting portion of said elongated portion is placed, such that adduction is restricted more degrees than extension.

The restricting portion of said elongated portion is placed, such that abduction is restricted more degrees than extension.

The restricting portion of said elongated portion is placed in any of the ways described in above.

Please note that any embodiment or part of embodiment as well as any method or part of method could be combined in any way. All examples herein should be seen as part of the general description and therefore possible to combine in any way in general terms.

BRIEF DESCRIPTION OF DRAWINGS

The invention is now described, by way of example, with reference to the accompanying drawings, in which:

FIG. 2*d* shows pelvis in a perspective view from below,

FIG. 2*e* shows the acetabulum, schematically,

FIG. 2*f* shows the acetabulum, schematically,

FIG. 4*a* shows the reaming of the collum and caput femur,

FIG. 4*b* shows the step of applying an adhesive to the created hemi-spherical cavity in the femoral bone, FIG. 6*a* shows the femoral bone when a medical device having a concave contacting surface has been provided to the hemi-spherical cavity, FIG. 6*b* shows the femoral bone when a medical device having a concave contacting surface has been provided to the hemi-spherical cavity, FIG. 6*c* shows the medical device fixated to the surgically cut caput femur using screws, FIG. 6*d* shows the medical device fixated to the femoral bone using fixating portions, FIG. 6*e* shows the medical device in which fixating portions are additionally fixated using screws, FIG. 9 shows a section of the medical device according to the embodiment also described with reference to FIG. 7*a,*

FIG. 10*a* shows the step of milling the periphery of the cortical bone of the caput femur, FIG. 10*b* shows the milling of the inside of the cortical bone of the caput femur, FIG. 17*a*-17*d* shows embodiments of the medical device, in side views, FIG. 18 shows the medical device in section, according to one embodiment, FIG. 19*a*-19*k* shows cross-sections of embodiments of the medical device, FIG. 20*a*-20*d* shows embodiments of the medical device in sectional side view and in cross-section.

FIG. 34*a*-34*d* shows embodiments of the medical device in combination with embodiments of the prosthetic replacement for the acetabulum, in a sectional side view and in cross-section.

DETAILED DESCRIPTION

Figure 1A:
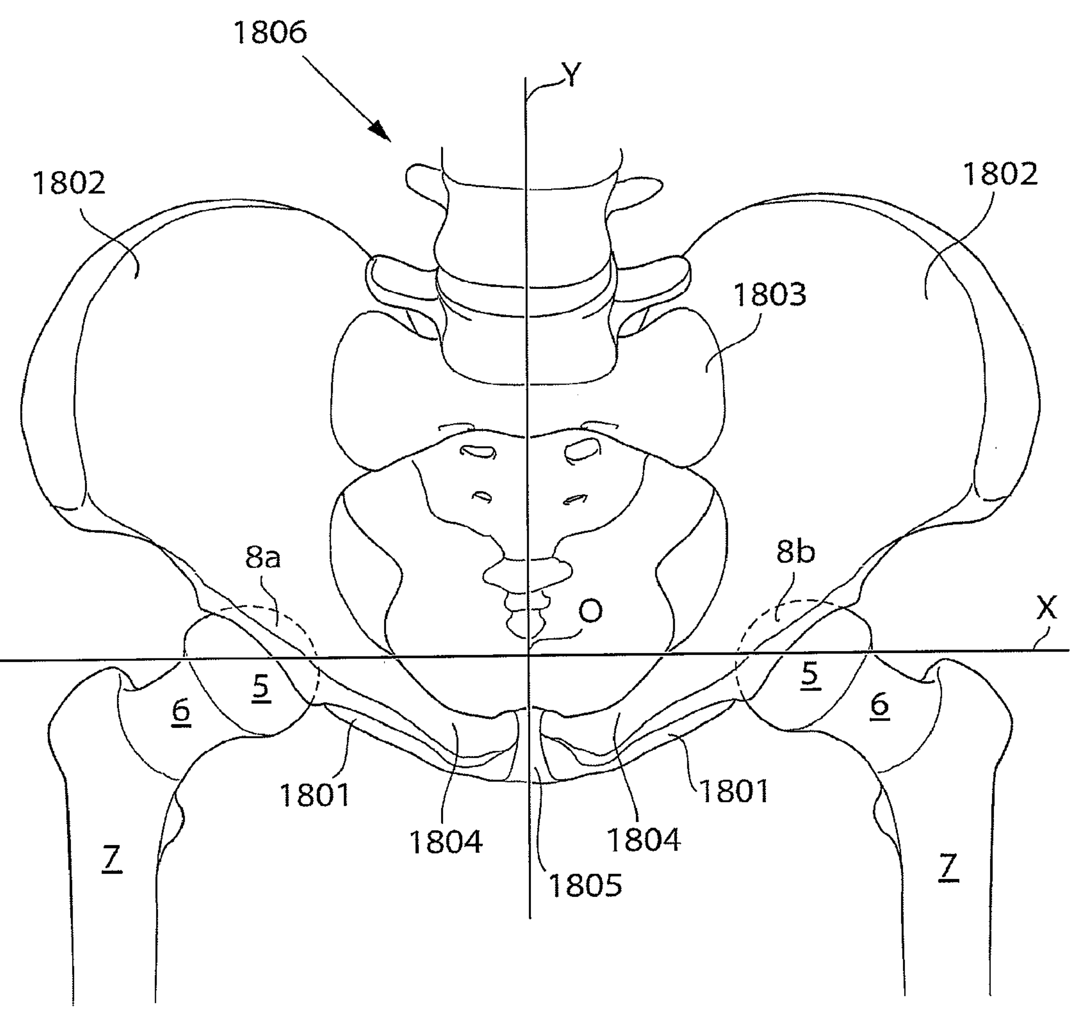
FIG. 1*a* shows pelvis in a frontal view.

The hip joint is a synovial ball and socket joint which permits a large motion range for allowing a plurality of different movements of the lower limb. From a neutral position the following movements of the hip joint are normally possible: Lateral or external rotation, 30° with the hip extended, 50° with the hip flexed, medial or internal rotation 40°, extension or retroversion 20°, flexion or anteversion 140°, abduction 50° with hip extended, 80° with hip flexed, adduction 30° with hip extended, 20° with hip flexed.

When replacing the natural hip joint with a prosthetic hip joint, the depth of the prosthetic acetabulum will affect the motion range, the deeper the acetabulum bowl is made the more restrictive it is to the motion range. A deeper bowl has the advantage of reducing the risk of hip joint luxation, the risk of which is a major drawback with prosthetic hips of today.

The anatomy of the hip joint and its surroundings is further disclosed in: Marieb et al., Human Anatomy, 2003, Benjamin Cummings, San Francisco, pages 195-202 and in Moore et al., Clinically oriented anatomy, 1999, Lippincott, Williams & Wilkins, Baltimore, pages 501-653, both hereby incorporated by reference.

Centrally in the body should herein be understood as a point of reference located at the intersection of the Median plane and the Coronal plane and in the center part of the heart along a longitudinal axis (Caudal-Cranial). Proximal and distal are direction or location terms used in relation to said point centrally in the body and hence a distal point is a point farther away from the central point in relation a proximal point of the same structure. Any plane disclosed herein is to be understood as having infinite extension. Other anatomical terms used herein are further described in Moore et al., Clinically oriented anatomy, 1999, Lippincott, Williams & Wilkins, Baltimore, pages 2-10, which is hereby incorporated by reference.

Functional hip movements are to be understood as movements of the hip that at least partly correspond to the natural movements of the hip. On some occasions the natural movements of the hip joint might be somewhat limited or altered after hip joint surgery, which makes the functional hip movements of a hip joint with prosthetic surfaces somewhat different than the functional hip movements of a natural hip joint.

Everyday activities is to be understood as activities which are not connected to any extreme movements, such that some physical sports require. For example, everyday activities comprise: walking, sitting, cycling etc.

The functional position of an implantable medical device or prosthesis is the position in which the hip joint can perform functional hip movements. The final position is to be understood as a functional position in which the medical device needs no further position change to function.

Arthroscopy is to be understood as key hole surgery performed in a joint, since the arthroscopic procedure could be performed in the abdomen of the patient some of the steps of this arthroscopic procedure is more laparoscopic, however for the purpose of this invention the two terms arthroscopy and laparoscopy is used synonymously and for the purpose of this invention the main purpose of these methods are is that they are minimally invasive.

Elastic deformation is when a material deforms under stress (e.g. external forces), but returns to its original shape when the stress is removed. A more elastic material is to be understood as a material having a lower modulus of elasticity. The elastic modulus of an object is defined as the slope of its stress-strain curve in the elastic deformation region. The elastic modulus is calculated as stress/strain, where stress is the force causing the deformation, divided by the area to which the force is applied; and strain is the ratio of the change caused by the stress.

Elasticity is to be understood as a materials ability to deform in an elastic way.

Stiffness is to be understood as the resistance of an elastic body to deformation by an applied force.

Biocompatible material is to be understood as being a material with low level of immune response. Biocompatible materials are sometimes also referred to as biomaterials. Analogous is biocompatible metals a biocompatible metal with low immune response such as titanium or tantalum. The biocompatible metal could also be a biocompatible alloy comprising at least one biocompatible metal.

Form fitting is to be understood as an element having a part or section which is adapted to enable a mechanical connection of said element to at least one other element using said part or section. Form fitted structure is a structure of an element which enables form fitting.

In the following a detailed description of embodiments of the present invention will be given. In the drawing figures, like reference numerals designate identical or corresponding elements throughout the several figures. It will be appreciated that these figures are for illustration only and are not in any way restricting the scope of the invention. Thus, any references to direction, such as "up" or "down", are only referring to the directions shown in the figures. Also, any dimensions etc. shown in the figures are for illustration purposes.

FIG. 1*a* shows the pelvis in a frontal view. Pelvis comprises the right and left hip bone making up the pelvic bone, in turn comprising the Sacrum 1803, Ilium 1802, Pubis 1804 and Ischium 1801. The hip joint houses the right and left acetabulum 8*a,b* placed laterally and distally in the pelvis. The acetabulum 8*a,b* being a spherically shaped cavity in the hip bones making up one of the parts of the hip joint, the acetabulum 8*a,b* being adapted to house the caput femur 5, being the proximal portion of the femoral bone 7 having a spherical contacting surface adapted to be placed in the acetabulum 8*a,b* and thus creating the operable hip joint. The pelvis has a right-left axis X extending substantially from the bottom of the left acetabulum 8*a* to the bottom of the right acetabulum 8*b*, the pelvis further having a caudal-cranial axis Y extending perpendicular to said right-left axis, centrally and substantially along the length of the patient, passing the dorsal portions of the pubic symphysis 1805 and substantially following the spinal cord 1806, intersecting the left-right axis X.

Figure 1B:
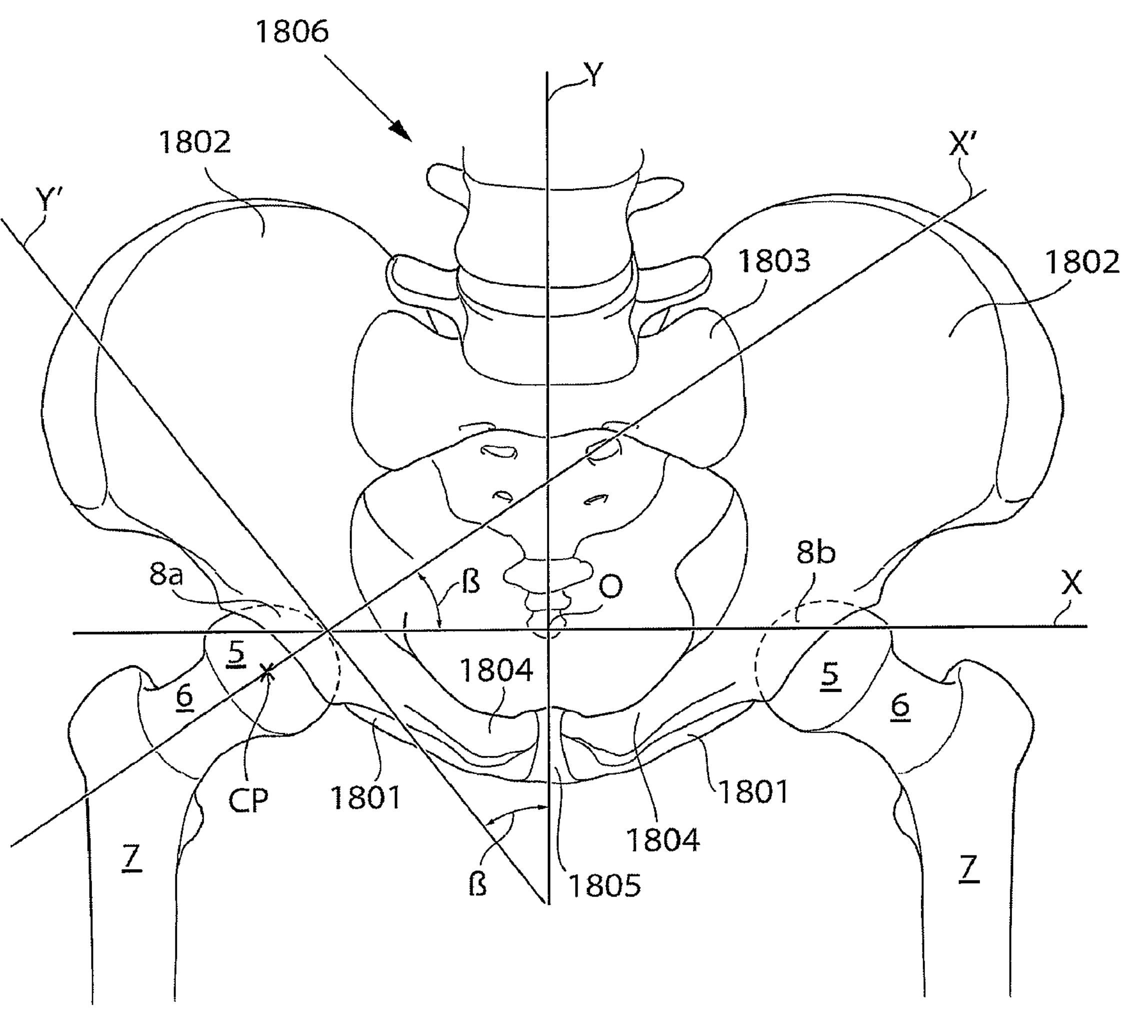
FIG. 1*b* shows pelvis in a frontal view.

FIG. 1*b* shows the pelvis in a frontal view disclosing a second, displaced coordinate system. The second displaced coordinate system has its origin O' in the bottom of the acetabulum bowl 8*a*. The axis X and Y have, in a frontal view, been rotated the angle β, creating the axis X' and Y'. The axis X' being aligned with the caput and collum femur center axis CX, when the hip joint is in its base position when the patient is standing up or lying down. In said base position, the axis X' goes through a point O' being the origin O' in the bottom of the acetabulum bowl 8*a*, and a center point CP, being a point in the center of a circle defined by the edges of the acetabulum bowl 8*a*, and further trough the top of the caput femur 5 and following inside of the collum femur 6, aligned with the collum femur 6. The axis Y' is perpendicular to the axis X' and goes through the origin O' in the bottom of the acetabulum bowl 8*a*, parallel to a plane defined by the circle defined by the edges of the acetabulum bowl 8*a*.

Figure 1C:
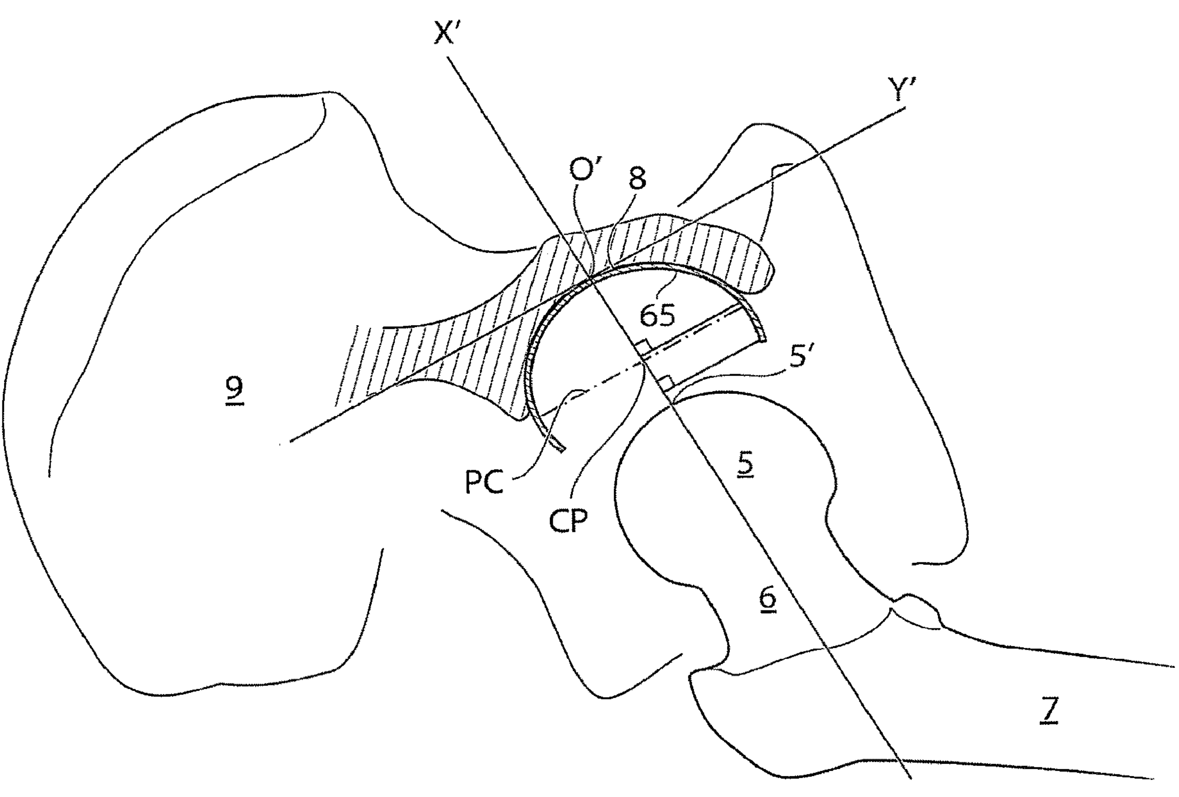
FIG. 1*c* shows the hip joint in section.

FIG. 1*c* shows the right pelvic bone 9 in section disclosing the second, displaced coordinate system. The origin O' is in the bottom of the acetabulum bowl 8. The axis X' is aligned with the caput 5 and collum 6 femur center axis CX, when the hip joint is in its base position when the patient is standing up or lying down with extended leg. In said base position the axis X' is goes through a point O' being the bottom of the acetabulum bowl 8, and a center point CP, being a point in the center of a circle defined by the edges of the acetabulum bowl 8, and further trough the top of the caput femur 5' and following inside of the collum femur 6, aligned with the collum femur 6. The axis Y' is perpendicular to the axis X', goes through the origin O' in the bottom of the acetabulum bowl 8, parallel to the plane PC defined by the circle defined by the edges of the acetabulum bowl 8.

Figure 2A:
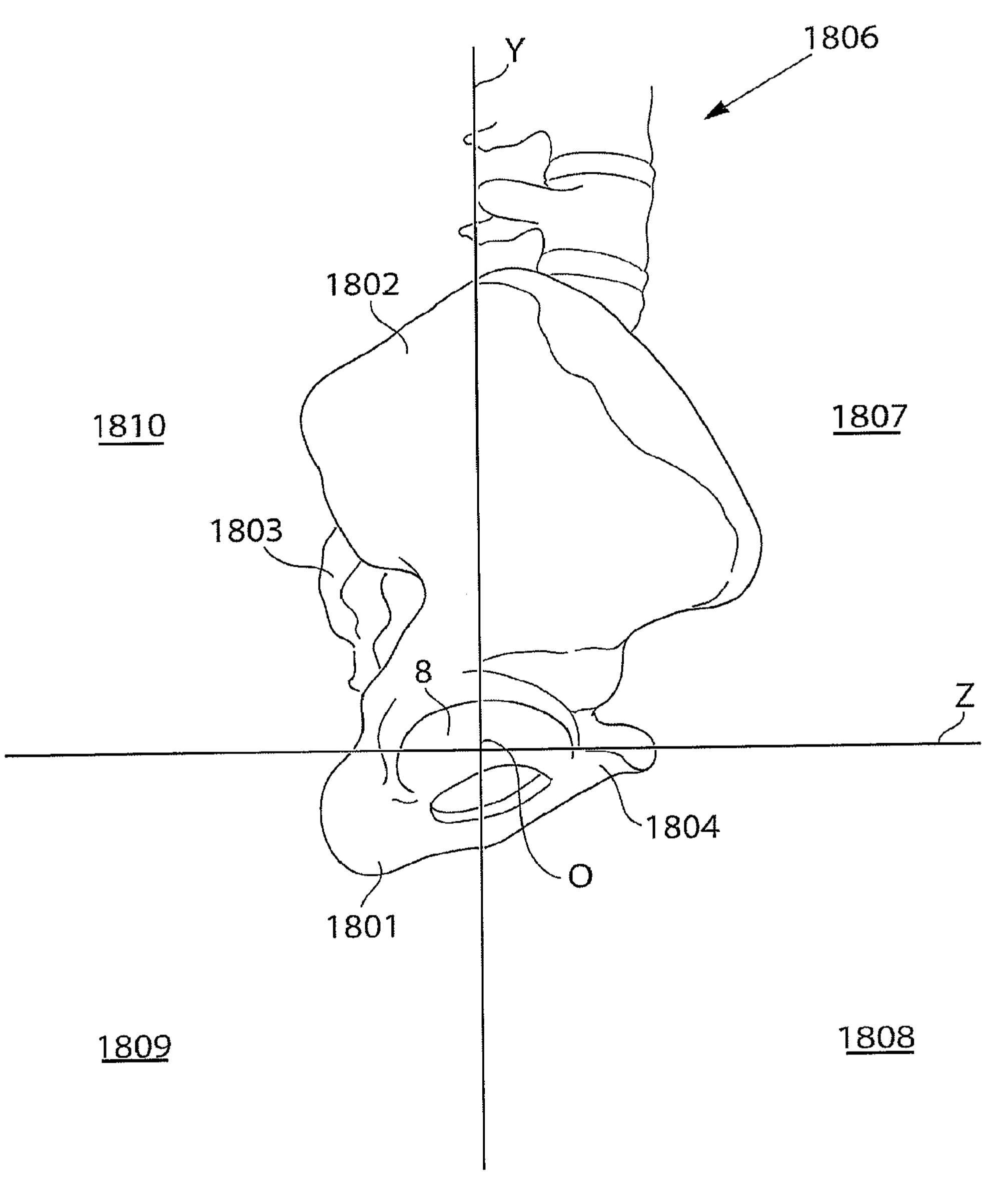
FIG. 2*a* shows pelvis in a lateral view.

FIG. 2*a* shows the pelvis in a lateral view, thus displaying the posterior side of Ilium 1802, the anterior side of Ichum 1801, the anterior side of Pubis 1804, and Sacrum 1803 in a lateral view. The pelvis has furthermore a dorsoventral axis Z being perpendicular to the caudal-cranial axis Y and the right-left axis X shown in FIG. 1, and intersecting them both creating a common origin O for the three axis X,Y,Z. The dorsoventral axis Z and the caudal-cranial axis Y thus being oriented such that a horizontal pelvis plane PXZ extends from the dorsoventral axis Z, and a coronal plane PXY extends from the caudal-cranial axis Y.

Figure 2B:
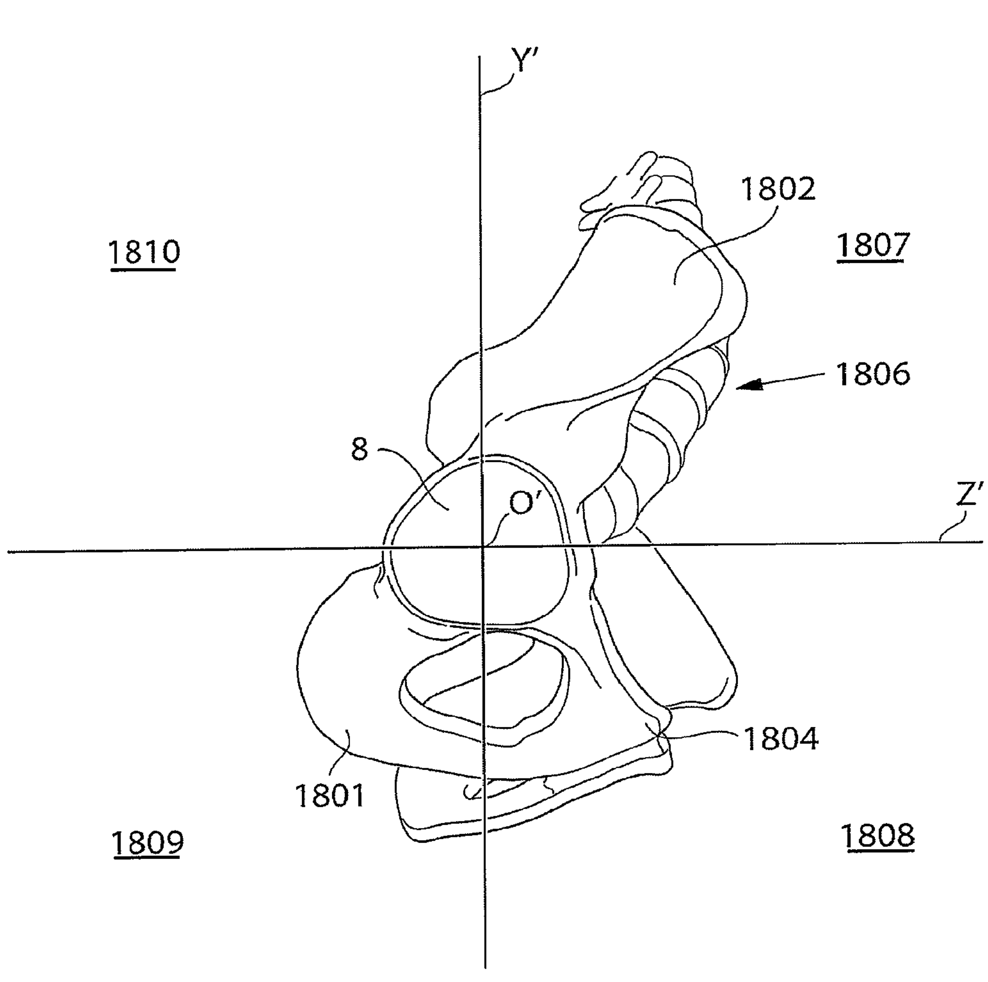
FIG. 2*b* shows pelvis in a lateral view.

FIG. 2*b* shows the pelvis in a plane view from the side and slightly from below, in the direction of the axis X' (further disclosed with reference to FIGS. 1*b* and 1*c*). The view of FIG. 2*b* displaying the axis Y' and Z' with origin O' in the bottom of the acetabulum bowl 8 making up the acetabulum coordinate system. The axis Y', Z', in this plane view, dividing the acetabulum bowl 8 into four quadrants: the proximal-frontal quadrant 1807, the distal-frontal quadrant 1808, the distal-dorsal quadrant 1809 and the proximal-dorsal quadrant 1810.

Figure 2C:
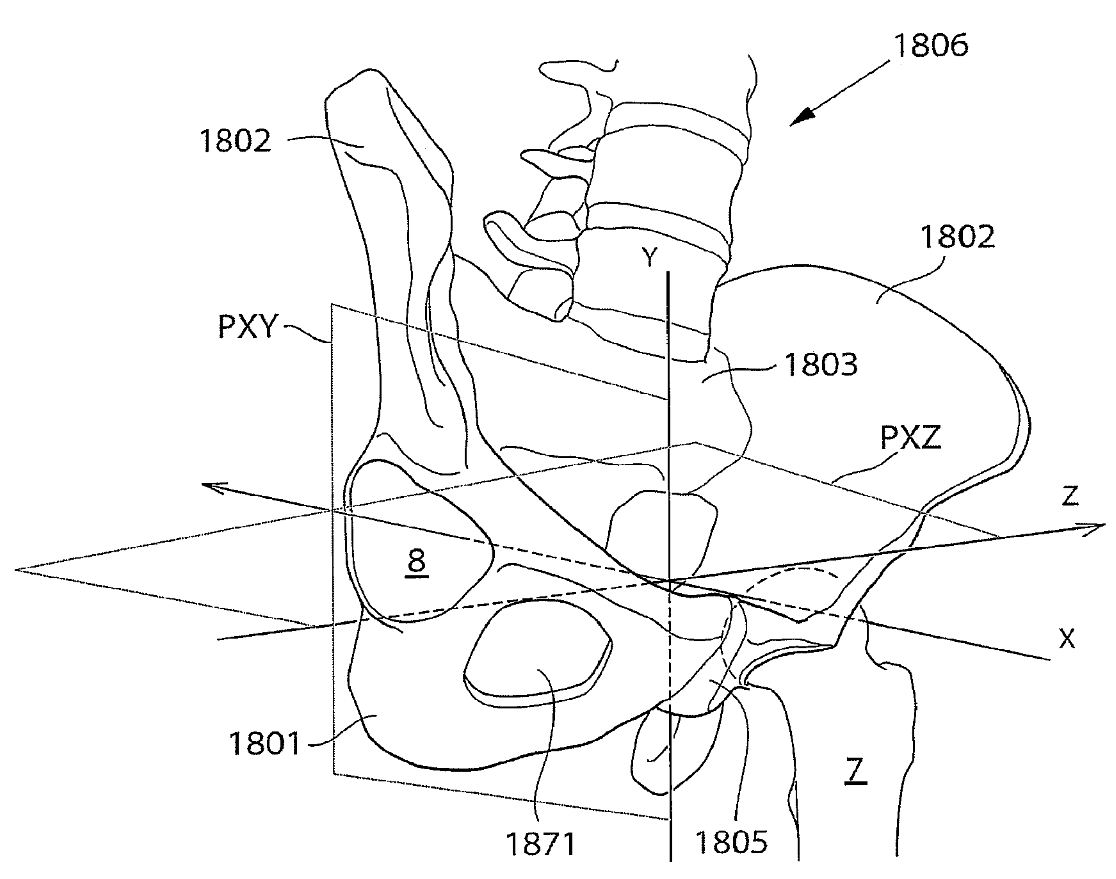
FIG. 2*c* shows pelvis in a perspective view from below.

FIG. 2*c* shows the pelvis in a perspective view from below and slightly from the front, displaying the right-left axis X passing through the center of the right and left acetabulum 8. The right-left axis X is perpendicular to the dorsoventral axis Z which also is perpendicular to the caudal-cranial axis Y. The coronal plane PXY extends from the dorsoventral axis Y, and the horizontal pelvis plane PXZ extends from the dorsoventral axis Z, thus being perpendicular to the coronal plane PXY.

FIG. 2*d* shows the coordinate system X,Y,Z and planes PXY, PXZ of FIG. 2*c*, and the second, displaced, coordinate system X', Y', Z' being the coordinate system of the acetabulum 8, also shown in FIG. 2*b*. The axis of the coordinate system of the acetabulum X', Y', Z' having their origin O' in the bottom of the acetabulum bowl 8, the axis X' being aligned with the caput and collum center axis. FIG. 2*d* further discloses the vertical acetabulum plane PX'Y' and the horizontal acetabulum plane PX'Z', PX'Y' being defined by the axis X',Y' and the vertical acetabulum plane PX'Z' being defined by the axis X',Z'. The planes PX'Y' and PX'Z' dividing the acetabulum bowl 8 into four quadrants, the proximal-frontal quadrant 1807, the distal-frontal quadrant 1808, the distal-dorsal quadrant 1809 and the proximal-dorsal quadrant 1810, in accordance with what is previously disclosed, with reference to FIG. 2*b*. FIG. 2*d* further shows the location of foramen obturatum 1871.

FIG. 2*e* shows, schematically how the acetabulum coordinate system X',Y',Z' relates to the hemisphere defined by the acetabulum bowl 8.

FIG. 2*f* shows, schematically, how the vertical acetabulum plane PX'Y', and the horizontal acetabulum plane PX'Z' divides the acetabulum 8 into four quadrants; the proximal-frontal quadrant 1807, the distal-frontal quadrant 1808, the distal-dorsal quadrant 1809 and the proximal-dorsal quadrant 1810, in accordance with the previously disclosed, with reference to FIGS. 2*b* and 2*d*.

Figure 2G:
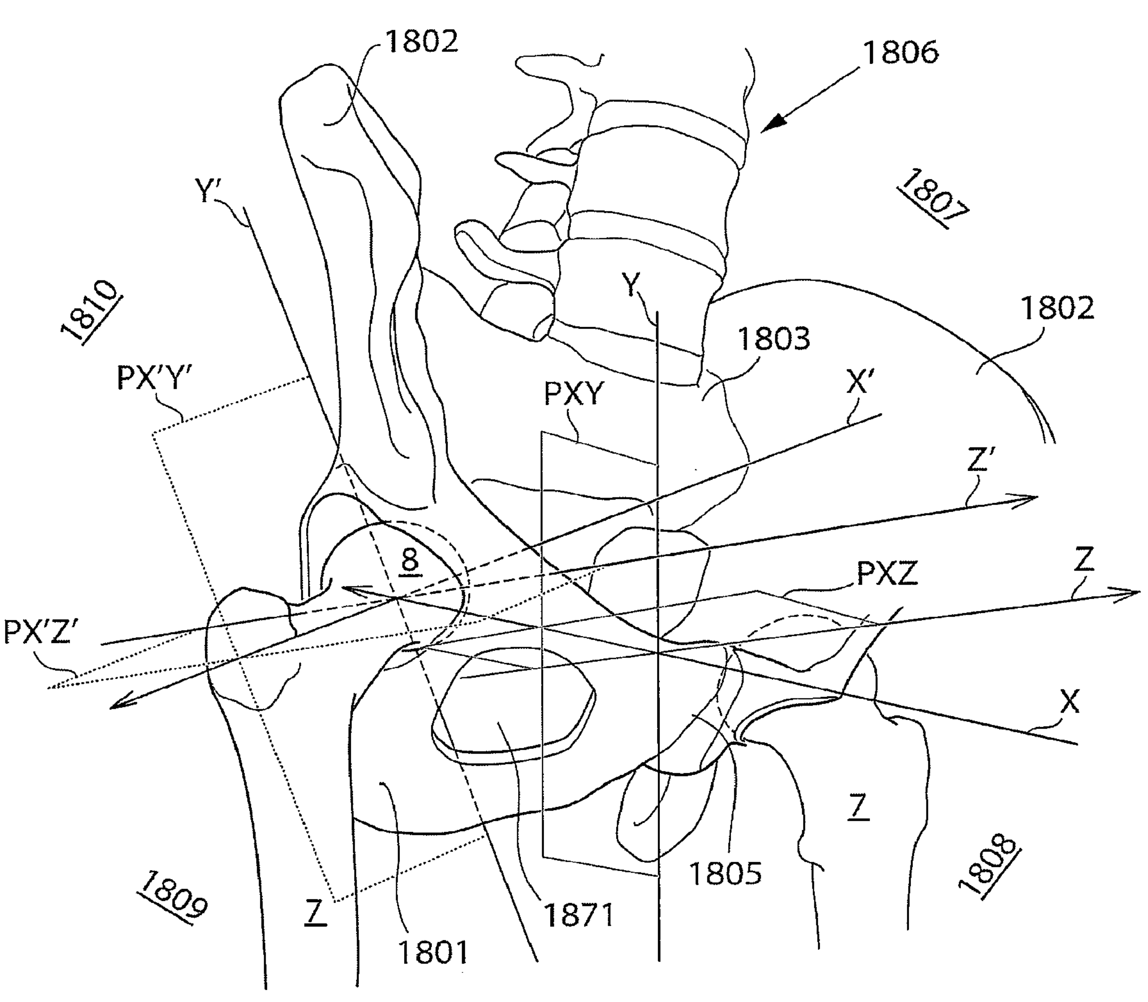
FIG. 2*g* shows pelvis in a perspective view from below.

FIG. 2*g* shows the view of FIG. 2*d*, and in addition it shows the horizontal and vertical acetabulum planes PX'Y' and PX'Z' also being the caput and collum femur horizontal and vertical planes PX'Y' and PX'Z', analogically dividing the caput and collum femur into four quadrants.

Figure 3A:
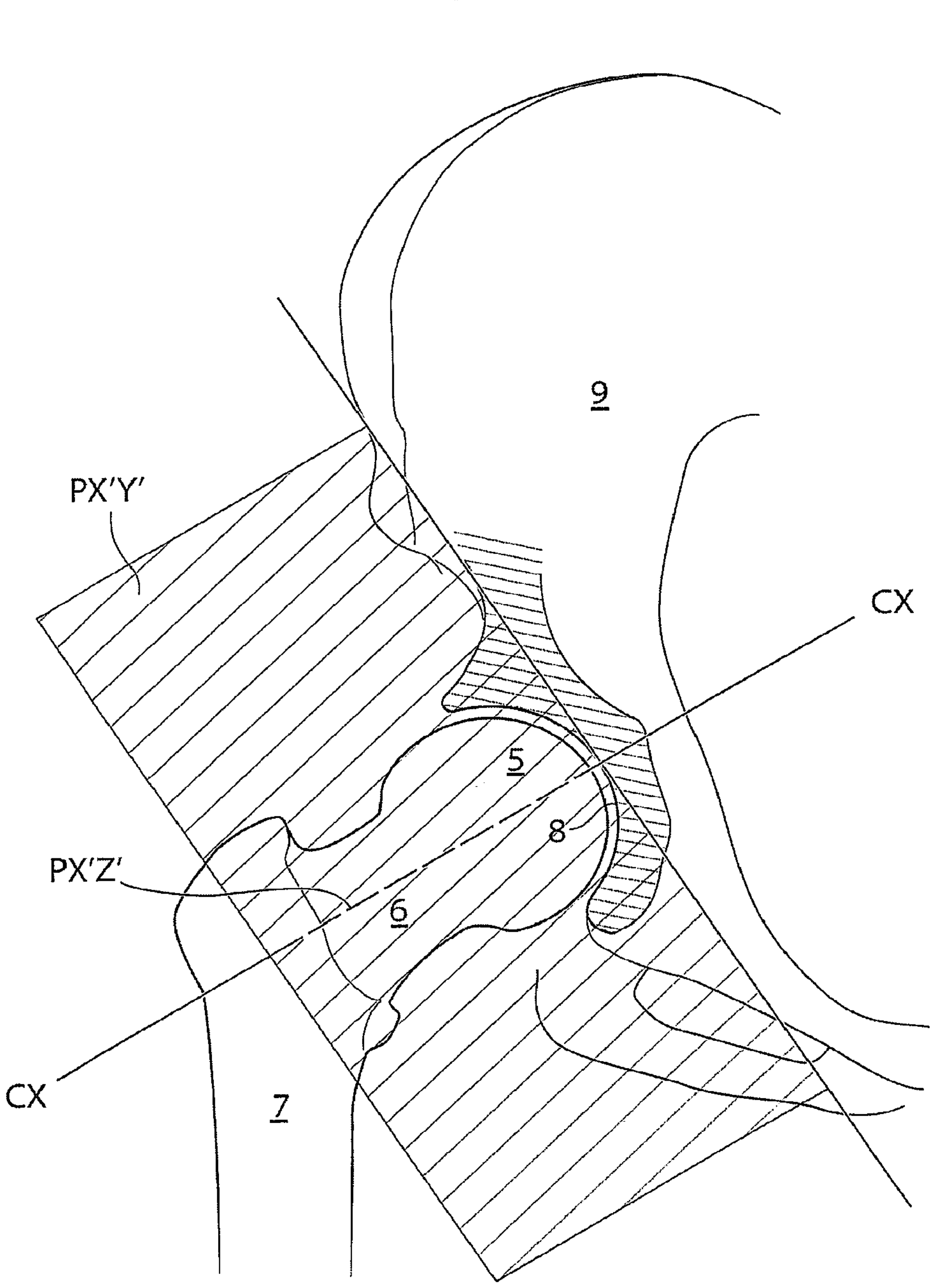
FIG. 3*a* shows the hip joint in section.

FIG. 3*a* shows a perspective view of the hip joint in section, displaying the horizontal and vertical planes PX'Y' and PX'Z' originating from the caput 5 and collum 6 center axis CX and dividing the caput 5 and collum 6 femur into quadrants.

Figure 3B:
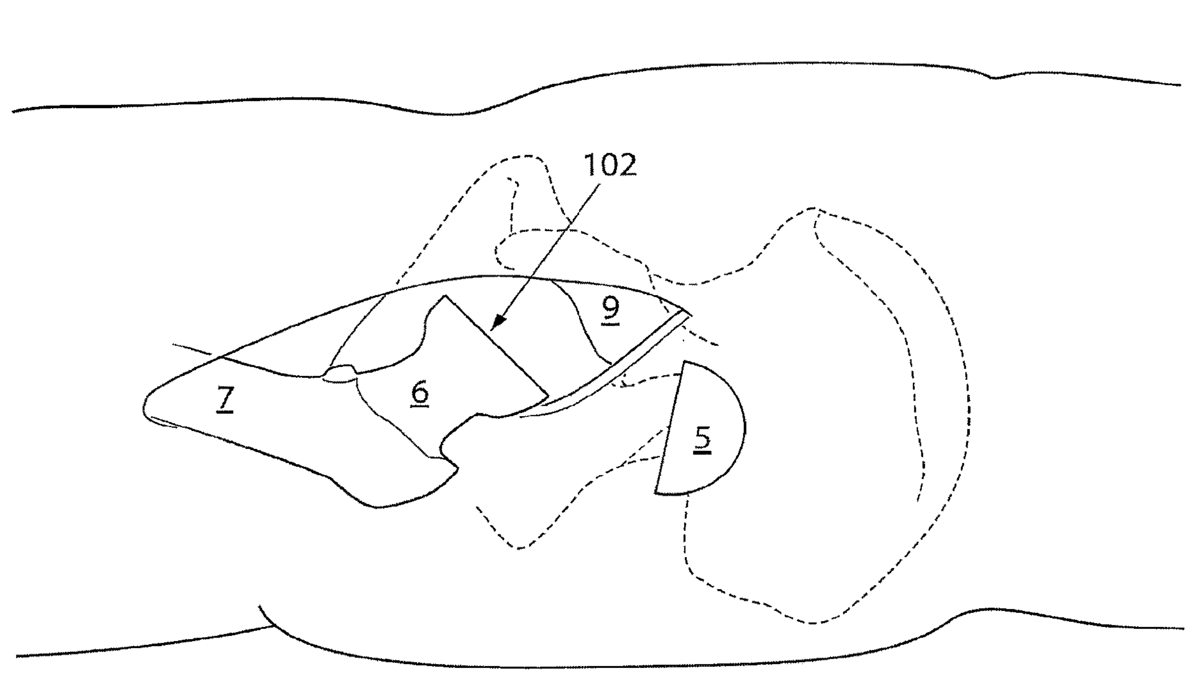
FIG. 3*b* shows the step of removing a proximal part of the caput femur.

FIG. 3*b* shows the proximal part of the caput femur 5 being removed e.g. by means of a bone saw. A surface of a section 102 is thus created perpendicularly to a length axis of the collum femur 6

FIG. 4*a* shows the reaming of the collum femur 6 and caput femur 5 using a reamer 40 connecting to an elongated member 21 by a connecting section 101. The reamer 40 creating a hemi-spherical cavity, having a concave surface 103, centrally placed in the caput 5 and collum femur 6.

FIG. 4*b* shows the step of applying an adhesive 106 to the created hemi-spherical cavity in the femoral bone using an injecting member 104 having an injecting nozzle 105. In the embodiment shown in FIG. 4*b* the injecting member is inserted into an area of the hip joint through a hole 18 in the pelvic bone 9, however it is equally conceivable that the injecting member is inserted through the hip joint capsule 12 or the femoral bone 7.

Figure 5:
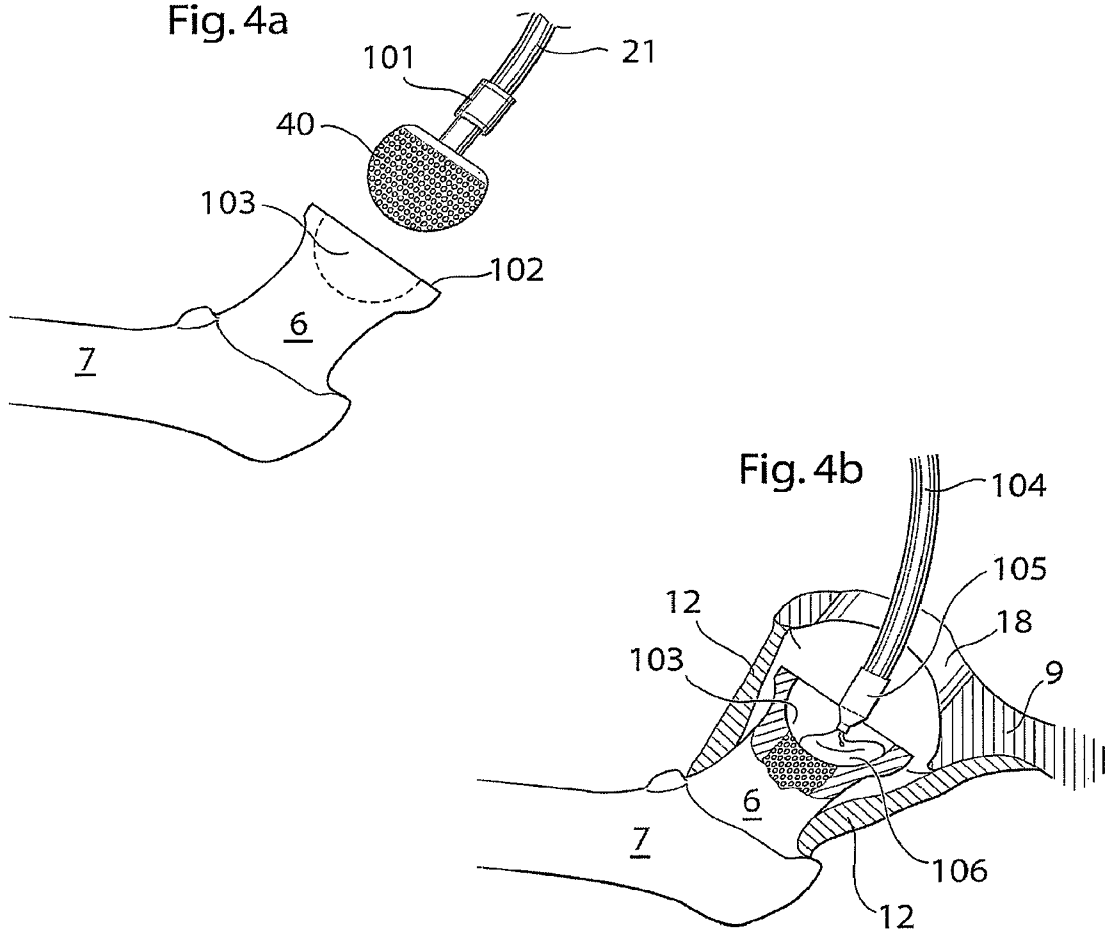
FIG. 5 shows the collum and caput femur when a medical device gas been fixated.

FIG. 5 shows the femoral bone 7 when a medical device 109 having a concave contacting surface has been provided to the hemi-spherical cavity, centrally placed in the caput 5 and collum femur. An elastic layer 109*b* adapted to absorb shocks from the femoral bone has been placed between the surface 109*c* adapted to be in contact with the artificial caput femur surface, and the femoral bone 7, 6. The elastic layer 109*b* could be an elastic polymer layer, such as a polyurethane or silicone layer. Having a layer absorbing shocks in the hip joint reduces the risk of fastening elements in contact with bone being affected by strains such that the fastening elements are loosened from their respective fastening positions, it also increases the comfort for the patient.

FIG. 6*a* shows the femoral bone 7 when a medical device having a concave contacting surface 110 has been provided to the hemi-spherical cavity, centrally placed in the caput 5 and collum femur. The medical device has been fixated to the femoral bone 7 using screws 121 placed aligned with the caput and collum femur center axis and entering the cortical bone of the caput femur.

FIG. 6*b* shows the femoral bone 7 when a medical device having a concave contacting surface 110 has been provided to the hemi-spherical cavity, centrally placed in the caput 5 and collum femur. The medical device comprises fixating portions 680 extending on the outside of the surface of a section 102 of the surgically cut caput femur, comprising cortical bone in the periphery thereof, thereby stabilizing the medical device with the artificial concave acetabulum surface 110 in the surgically cut caput femur.

FIG. 6*c* shows an alternative embodiment, in which the medical device has been fixated to the surgically cut caput femur using screws 121 entering the cortical bone 601 of the caput femur.

FIG. 6*d* shows yet another embodiment, in which the medical device is fixated to the femoral bone using fixating portions, in accordance with the embodiment described with reference to FIG. 6*b*, and an elongated member 681. The elongated member is according to this embodiment a threaded member 681 extending along the collum and caput femur center axis, in the cancellous bone 602 of the collum femur, and entering the cortical bone 601 of the femoral bone, on the inside thereof, in the area of the greater trochanter. The threaded elongated member 681 creates an axial force when pulled pressing the medical device towards the surface of a section 102 of the surgically cut caput femur, thereby stabilizing and fixating the medical device in the concave cavity created in the caput femur.

FIG. 6*e* shows yet an alternative embodiment of the medical device in which the fixating portions 680 are additionally fixated using screws 121 placed from the outside of the surgically cut caput femur, perpendicularly to the collum and caput femur center axis.

Figures 7A, 7B, 7C, 7D, 7E, 7F:
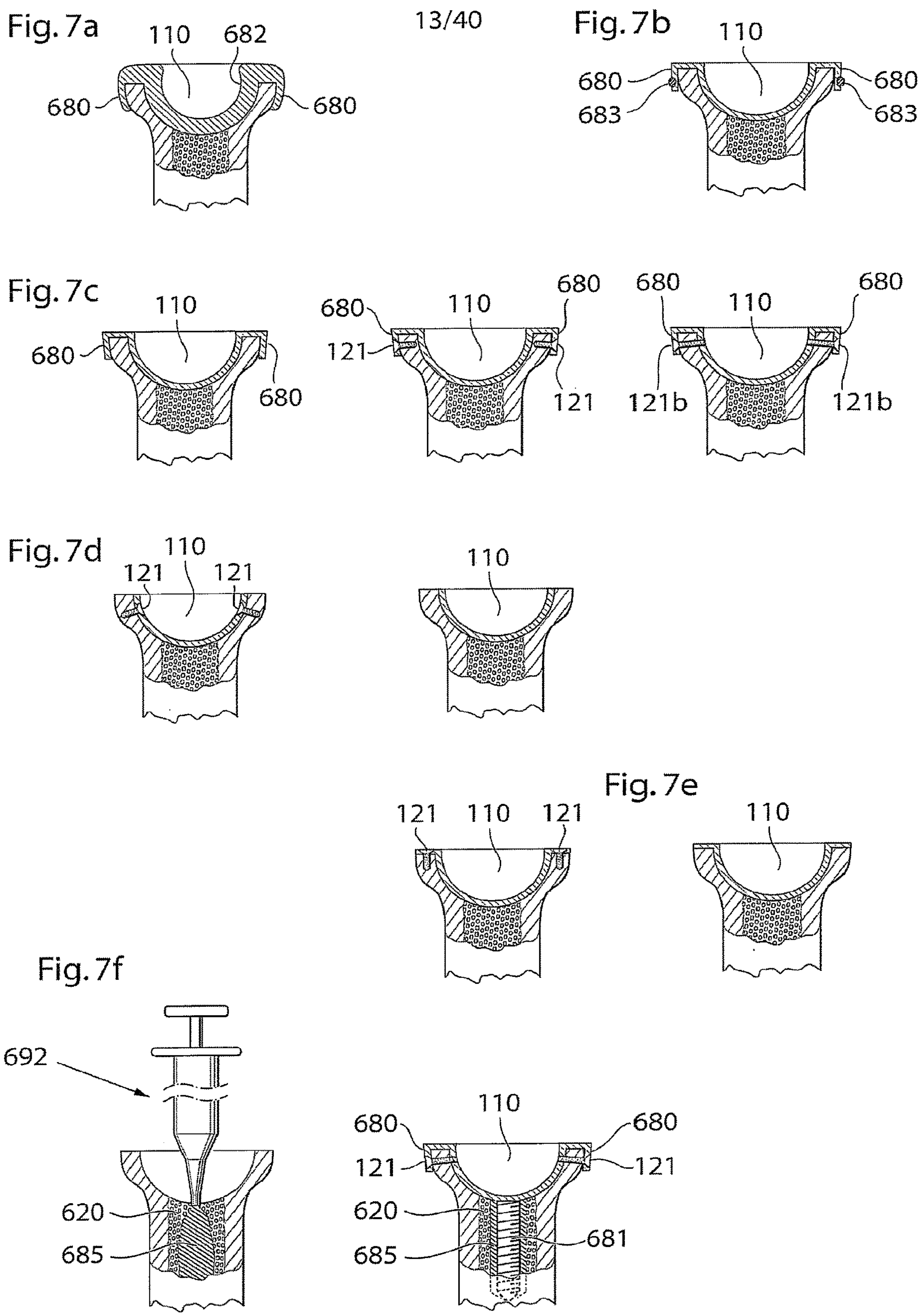
FIG. 7*a* shows the medical device in which the fixating portions extends beyond the greatest circumference of the surgically cut caput femur.
FIG. 7*b* shows the medical device additionally fixated using a fixating band.
FIG. 7*c* shows three different embodiment of medical devices comprising fixating portions which are slightly tilted towards the collum and caput femur.
FIG. 7*d* shows two embodiments in which the concave contacting surface only comprises the part placed inside of the concave cavity.
FIG. 7*e* shows two embodiments in which the artificial acetabulum surface extends into a portion placed on the surface of a section created when the caput femur is surgically cut, FIG. 7*f* describes the medical device fixated using an elongated member, fixating portions, and screws.

FIG. 7*a* shows the medical device in an embodiment in which the fixating portions 680 extends beyond the greatest circumference of the surgically cut caput femur and thereby clasps the medical device to the surgically cut caput femur, fixating the medical device thereon. The concave contacting surface 110 is also adapted to travel beyond the equator of an artificial caput femur which is placed in the artificial acetabulum when mounted into a functioning artificial hip joint, and clasping the artificial caput femur when mounted therein.

FIG. 7*b* shows yet another embodiment where the medical device is additionally fixated using a fixating band 683 encircling the fixating portions of the medical device and thereby further clasping the medical device to the surgically cut caput femur.

FIG. 7*c* shows three different embodiment of medical devices comprising fixating portions 680 which are slightly tilted towards the collum and caput femur center axis, thereby clasping a portion of the surgically cut caput femur for fixating the medical device to the surgically cut caput femur. The three different embodiments shown is first, without screws 121, second, with screws entering the cortical bone, and third, with screws penetrating the cortical bone and entering the medical device on the inside of the concave cavity, which enables the screws to squeeze a portion of the cortical bone for tight fixation of the medical device.

FIG. 7*d* shows two embodiments in which the concave contacting surface 110 only comprises the part placed inside of the concave cavity. The first embodiment shows the acetabulum surface 110 fixated to the concave cavity using screws 121, whereas the second embodiment shows the artificial acetabulum surface fixated without screws, such as using an adhesive.

FIG. 7*e* shows two embodiments in which the artificial acetabulum surface extends into a portion placed on the surface of a section created when the caput femur is surgically cut. In the first embodiment the medical device is fixated using screws entering the cortical bone, whereas in the second embodiment the artificial contacting surface is fixated without screws, such as using an adhesive.

FIG. 7*f* describes an embodiment in which the medical device is further fixated using an elongated member 681, fixating portions 680, and screws 121 placed between the fixating portions 680 and the inside of the artificial acetabulum contacting surface 110. The elongated member 681 is according to this embodiment a threaded member 681 and the first fig. discloses the preparation of the cancellous bone 602 with a curing fluid 685, such as bone cement, creating a sturdy base for the fixation of the threaded member 681.

Figure 8:
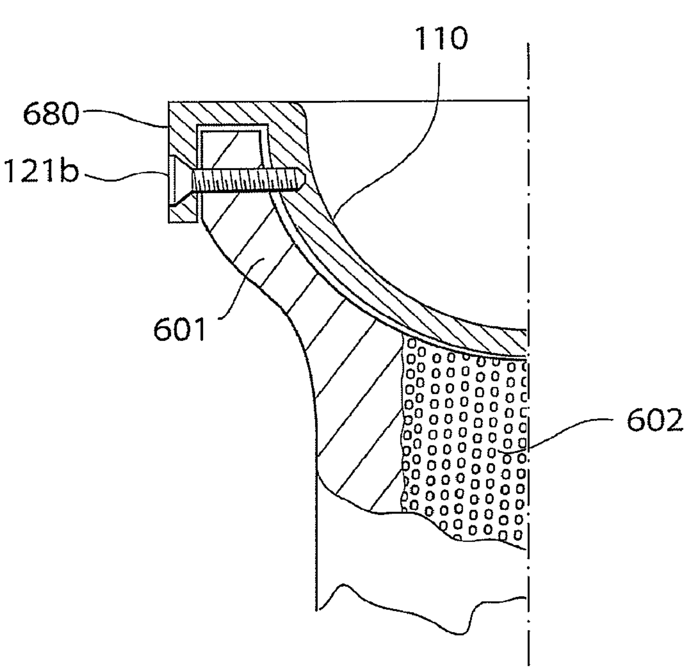
FIG. 8 shows the artificial acetabulum surface in further detail.

FIG. 8 shows the artificial acetabulum surface 110 in further detail when the artificial acetabulum surface comprises a fixating portion 680 extending on the outside of the cortical bone 601. The fixating portion 680 is further fixated using screws 121 placed from the outside, through a hole in the medical device, penetrating the cortical bone 601 of the surgically cut caput femur and entering the medical device placed in the concave cavity in the caput femur.

FIG. 9 shows a section of the medical device according to the embodiment also described with reference to FIG. 7*a*, in further detail. The medical device according to the embodiment in FIG. 9 comprises fixating portions 680 which reaches on the outside of the surgically cut caput femur and clasps the cortical bone of the caput femur. The medical device clasps the caput femur since a distance 687, between the collum and caput femur center axis CA and the fixating portion in shorter than a distance 686 between the collum and caput femur center axis CA and a portion of the fixating portion placed more proximally when the medical device is implanted. On the inside of the artificial concave acetabulum surface, the surface extends beyond the equator of the artificial caput femur adapted to be placed therein. An extending portion 682 clasps the artificial caput femur placed in the artificial acetabulum surface 110 since a distance 688, between the collum and caput femur center axis CA and the inside of the artificial acetabulum surface 110 is shorter than a distance 689 between the collum and caput femur center axis CA and a point on the inside of the artificial acetabulum contacting surface 110 being more distal when the medical device is implanted.

FIG. 10*a* shows the step of milling the periphery 690 of the cortical bone of the caput femur after the caput femur has been surgically cut, using a milling device 688 adapted therefor. The milling process creates a straighter edge which facilitates the fixation of a medical device on the outside of the caput femur.

FIG. 10*b* shows the milling of the inside of the cortical bone of the caput femur after the caput femur has been surgically cut, using a milling device 689 adapted therefore, creating a straighter edge which facilitates the fixation of a medical device on the inside of the caput femur.

Figure 11:
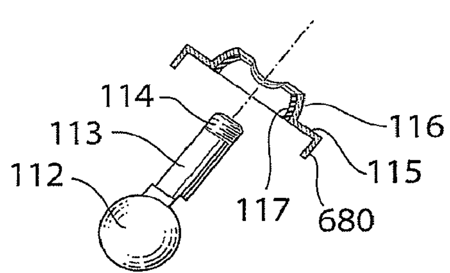
FIG. 11 shows an artificial convex caput femur surface adapted to be placed in an artificial acetabulum surface.

FIG. 11 shows an artificial convex caput femur surface 112 adapted to be placed in an artificial acetabulum surface according to any of the embodiments herein. After the artificial convex caput femur surface has been placed in the artificial acetabulum surface it is locked using a locking member 116 comprising a surface 117 adapted to be in contact with the artificial convex hip joint surface 112. The locking member 116 further comprises fixating members 115 which are adapted to assist in the fixation of the locking member 116 to the caput femur 5 or collum femur 6, which in turns fixates the artificial convex hip joint surface 112. The fixating members comprises a fixating portion 680 which travels on the outside of the surgically cut caput femur for radially stabilizing and fixating the locking member to the surgically cut caput femur. The artificial convex hip joint surface 112 is fixated to an elongated attachment rod 113 comprising a thread 114 and a recess 2203 for enabling further movement of the prosthetic replacement for the acetabulum 110 in relation to the spherical portion 112 connected to elongated portion 2201.

Figure 12:
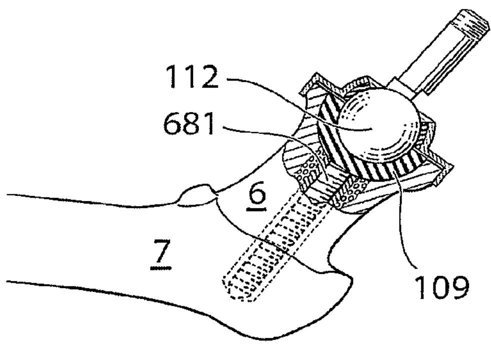
FIG. 12 shows the artificial convex caput femur surface as disclosed with reference to FIG. 11 when mounted in an artificial acetabulum surface.

FIG. 12 shows the artificial convex caput femur surface 112 as disclosed with reference to FIG. 11 when mounted in an artificial acetabulum surface 109 placed in a concave cavity in the femoral bone. The artificial acetabulum surface is according to this embodiment is fixated to the femoral bone using an elongated member 681, here being a threaded member placed aligned with the collum and caput center axis.

Figure 13:
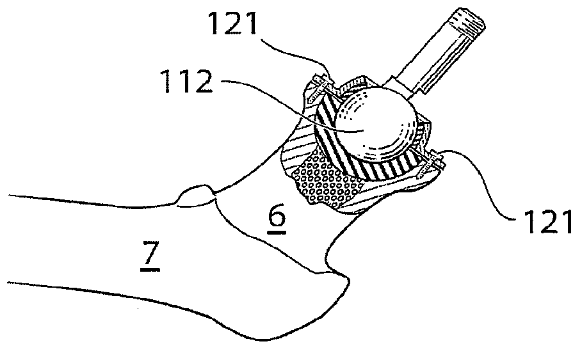
FIG. 13 shows the artificial convex caput femur surface as disclosed with reference to FIG. 11 when mounted in an artificial acetabulum surface.

FIG. 13 shows the artificial convex caput femur surface 112 as disclosed with reference to FIG. 11 when mounted in an artificial acetabulum surface 109 placed in a concave cavity in the femoral bone. The artificial acetabulum surface is according to this embodiment is fixated using screws 121 entering the cortical bone of the surgically cut caput femur.

Figure 14:
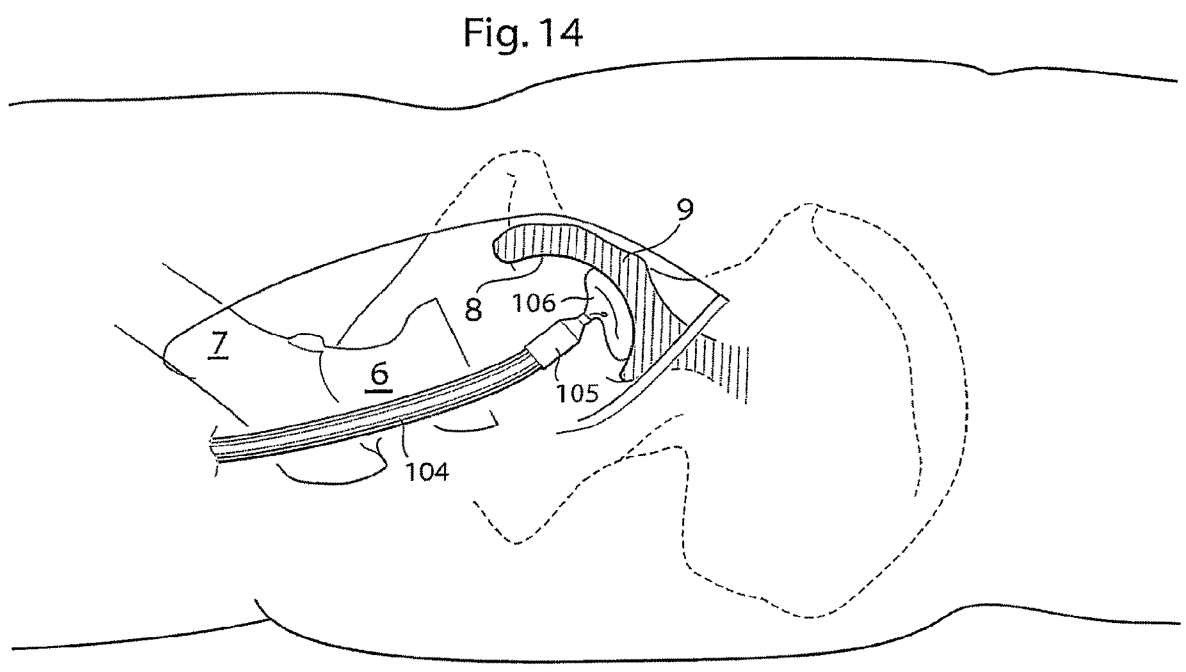
FIG. 14 shows the injection of an adhesive in the acetabulum in the pelvic bone.

FIG. 14 shows the injection of an adhesive 106 in the acetabulum 8 in the pelvic bone 9 using an injecting member comprising an injecting nozzle 105, which is a preparation for the fixation of a medical device to the pelvic bone 9.

Figure 15:
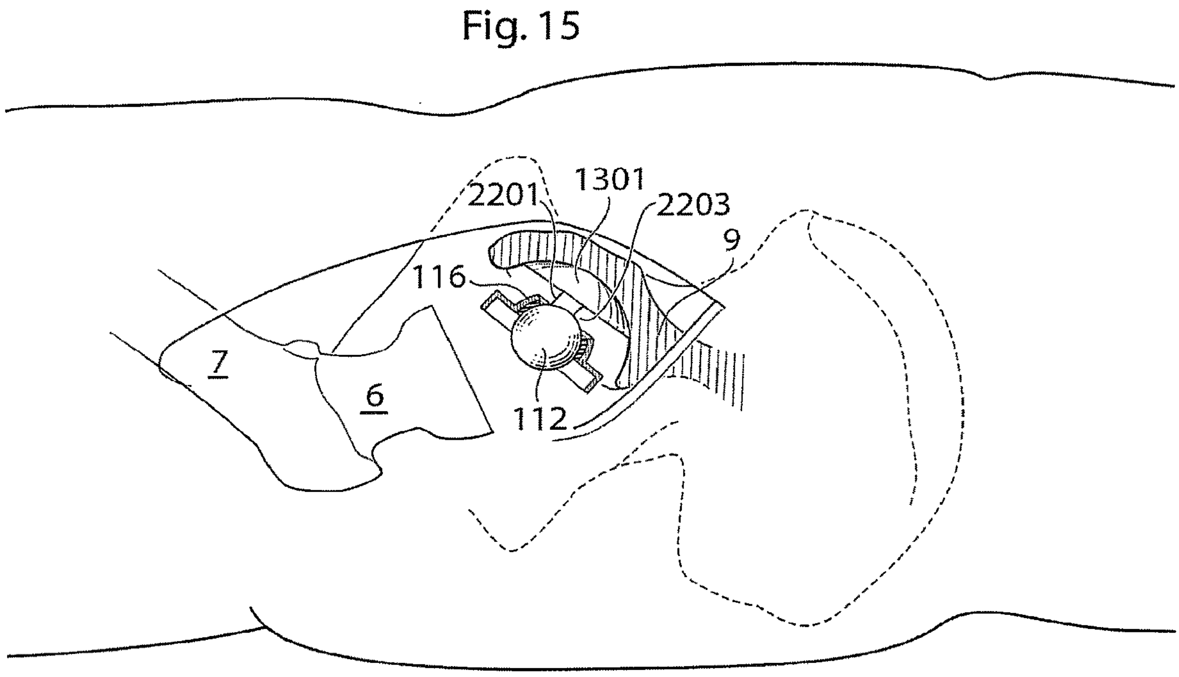
FIG. 15 shows the placing of a medical device in the reamed acetabulum surface of the pelvic bone.

FIG. 15 shows the placing of a medical device in the reamed acetabulum 8 surface of the pelvic bone 9. The medical device comprises a convex hip joint surface 112 fixated to a fixation element 1301, which in turn is fixated to the acetabulum 8 using the injected fluid, which could be assisted or replaced by a mechanical fixation element such as screws. The medical device further comprises a pre-mounted locking member 116 for locking the convex hip joint surface of the concave hip joint surface placed in the caput 5 and collum femur 6 for hindering dislocation of the hip joint when the hip joint is in its functional position. The artificial convex hip joint surface 112 is fixated to an elongated attachment rod 113 comprising a thread 114 and a recess 2203 for enabling further movement of the prosthetic replacement for the acetabulum 110 in relation to the spherical portion 112 connected to elongated portion 2201.

Figure 16A:
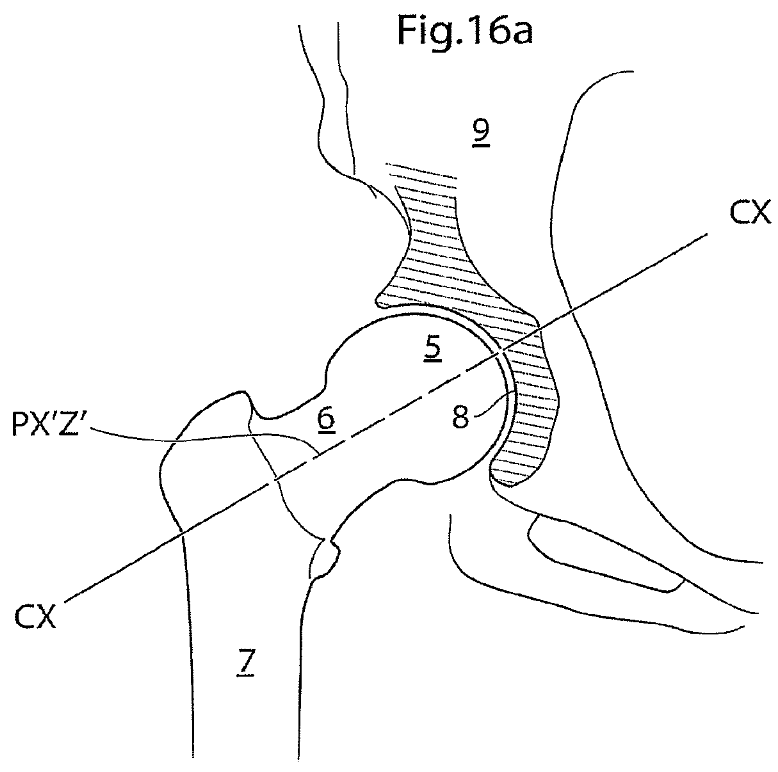
FIG. 16*a* shows the hip joint in section, separated.
Figure 16B:
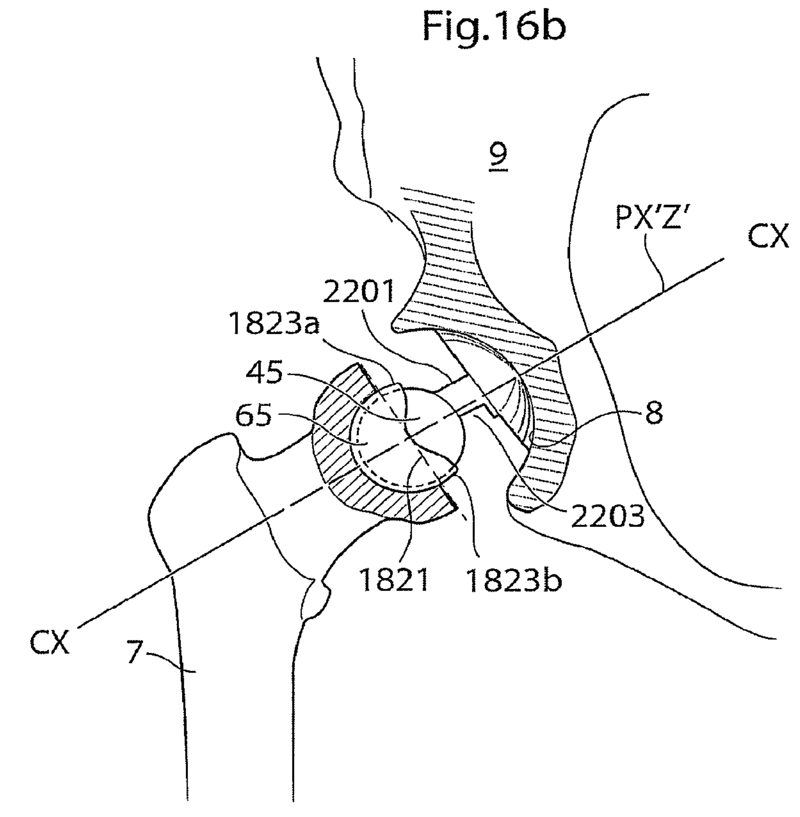
FIG. 16*b* shows the hip joint in section, with a prosthetic acetabulum surface placed in the hemi-spherical cavity in the femoral bone.

FIG. 16*b* shows the view of FIG. 16*a* when a prosthetic acetabulum surface 65 has been placed in the hemi-spherical cavity in the femoral bone replacing the natural contacting surface of the acetabulum 8. The prosthetic replacement for the acetabulum 8 comprises two extending portions 1823*a,b* adapted to clasp the spherical portion 45 being a prosthetic part adapted to replace the natural collum femur 5 and thus further restraining the prosthetic spherical replacement for the caput femur 45 in the prosthetic replacement for the acetabulum 65. The prosthetic replacement for the acetabulum 65 and the prosthetic spherical replacement for the caput femur 45 combined creating a functional prosthetic hip joint. FIG. 16*b* further shows an elongated portion 2201, adapted to at least partially replace the collum femur. The prosthetic spherical portion 45 and the elongated portion 2201 are connected to each other at the proximal portion of the elongated portion 2201. According to the embodiment shown in FIG. 16*b* the elongated portion 2201 is adapted to be placed and fixated inside of bowl shaped acetabulum 8 as part of the pelvic bone 9. The elongated portion 2201 restricts the movement of the prosthetic replacement for the acetabulum 65 in relation to the spherical portion 45, especially since the prosthetic replacement for the acetabulum comprises extending portions 1823*a,b* extending beyond the equator line of the prosthetic replacement for the acetabulum. The elongated portion thus further comprises a recess 2203 for enabling further movement of the prosthetic replacement for the acetabulum 110 in relation to the spherical portion 112 connected to elongated portion 2201.

Figure 16C:
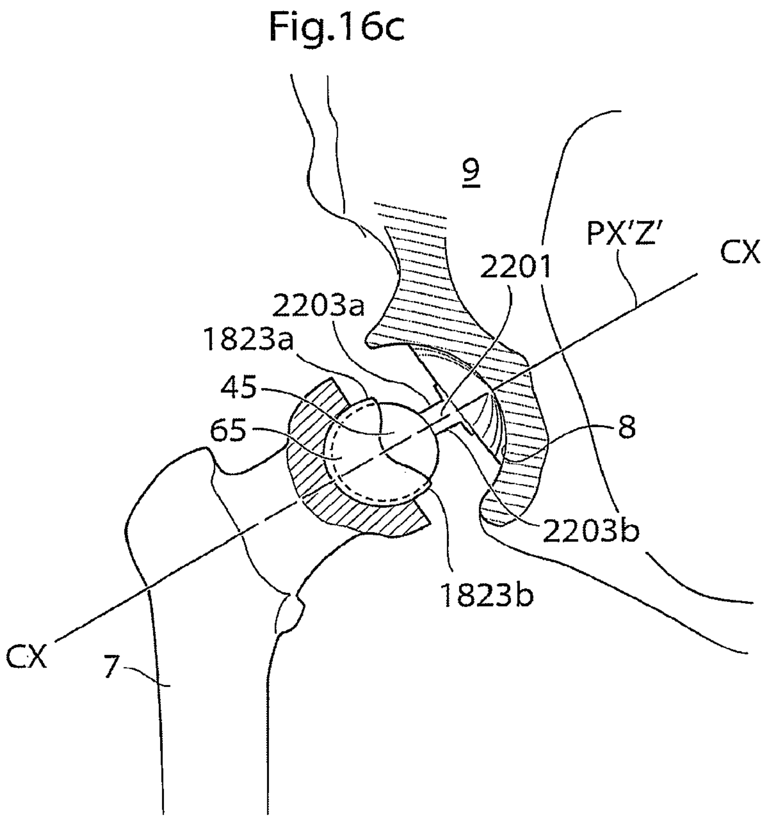
FIG. 16*c* shows the hip joint in section, with a prosthetic acetabulum surface placed in the hemi-spherical cavity in the femoral bone.

FIG. 16*c* shows a perspective view of the hip joint in section, similar to the embodiment shown in FIG. 16*b*. However, in the embodiment of FIG. 16*c* the elongated portion 2201 comprises two recesses 2203*a,b*, placed such that the elongated portion 2201 are adapted to receive the extending portions 1823*a,b* through the extending portions 1823*a,b* entering the recesses 2203*a,b* of the elongated portion 2201 when the prosthetic replacement for the acetabulum 65 move in relation to the elongated 2201 and spherical 45 portions.

Figure 16D:
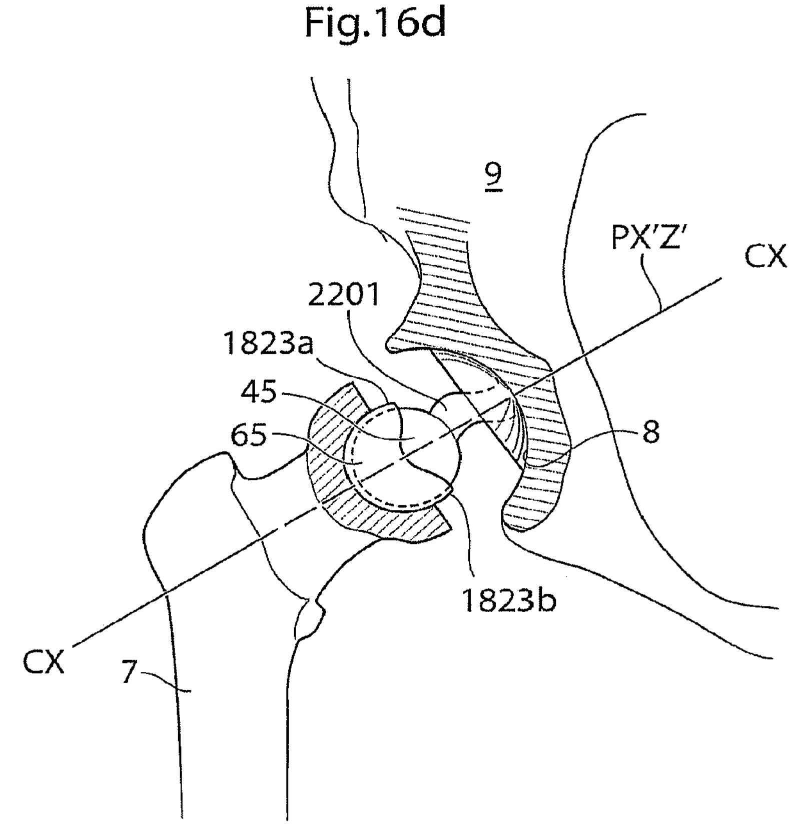
FIG. 16*d* shows the hip joint in section, with a prosthetic acetabulum surface placed in the hemi-spherical cavity in the femoral bone.

FIG. 16*d* shows a perspective view of the hip joint in section, similar to the embodiment shown in FIGS. 16*b* and 16*c*. However, in the embodiment of FIG. 16*d* the elongated portion 2201 is shaped such that the contacting portion between the elongated portion 2201 and the spherical portion 45 is eccentrically placed in relation to the center axis CX of the collum and caput femur. The eccentrically placed contacting portion enables replacement for the acetabulum to move more in one direction than in another. This embodiment, similar to the recess embodiments previously disclosed, enables the adaption of the elongated member to the prosthetic replacement for the acetabulum 65, and in particular the extending portions 1823*a,b* thereof, for enabling a particular motion pattern of the hip joint and thus the leg.

FIG. 17*a* shows a prosthetic spherical portion 45 and a prosthetic elongated portion 2201 in a schematic view, displaying the prosthetic elongated portion 2201 being connected to the prosthetic spherical portion 45. According to the embodiment shown in FIG. 17*a* the elongated portion 2201 does not have any recesses or adaptations facilitating the movement of the prosthetic portions in relation to a prosthetic replacement for the acetabulum comprising extending portions.

FIG. 17*b* shows a prosthetic spherical portion 45 and a prosthetic elongated portion 2201 in a schematic view in an embodiment where the elongated portion comprises a recess 2203*a* adapted to further enable movement of the prosthetic replacement for the acetabulum 65 in relation to the prosthetic spherical 45 and elongated portions 2201.

FIG. 17*c* shows a prosthetic spherical portion 45 and a prosthetic elongated portion 2201 in a schematic view in an embodiment in which the elongated portion 2201 comprises two recesses 2203*a,b* adapted to further enable movement of the prosthetic replacement for the acetabulum 65 in relation to the prosthetic spherical 45 and elongated portions 2201.

FIG. 17*d* shows a prosthetic spherical portion 45 and a prosthetic elongated portion 2201 in a schematic view in an embodiment in which the elongated portion 2201 is curved such that the area in which the elongated portion 2201 connects to the spherical portion 45 is eccentrically placed in relation to the collum and caput femur center axis CX.

FIG. 18 shows the prosthetic parts replacing the articulating surfaces of the hip joint. The prosthetic replacement for the acetabulum surface 65 comprises extending portions 1823*a,b* which are adapted to enter a recess 2203 of the prosthetic elongated portion 2201. The recess enables further movement of the prosthetic replacement for the acetabulum 65 in relation to the prosthetic spherical 45 and elongated portions 2201 in the direction of recess, such as disclosed in the right part of FIG. 5, where the prosthetic part is placed in a state in which the prosthetic replacement for the acetabulum 65 is moved maximally in the direction of the recess 2203.

FIG. 19*a* shows a cross-section of the prosthetic elongated portion without an adaptation to increase to motion range. This embodiment is disclosed in a schematic side view in FIG. 17*a*.

FIG. 19*b* shows a cross-section of the prosthetic elongated portion having a recess 2203 or adaptation such that said prosthetic replacement for the acetabulum 65 is adapted for further movement in relation to a prosthetic spherical 45 and elongated portion 2201 in the direction of the recess 2203 or adaptation. This embodiment is disclosed in a schematic side view in FIG. 17*b*.

FIG. 19*c* shows a cross-section of the prosthetic elongated portion where the restricting part of the elongated prosthetic portion is a narrow portion 2220, with a smaller cross-sectional area than other portions of the elongated portion. In embodiments where the extending portions of a prosthetic replacement for the acetabulum extends circularly 360° around the collum and caput center axis, the circular narrow portion 2220 disclosed in FIG. 19*c* enables further movement of the prosthetic replacement for the acetabulum 65 in all radial directions. This embodiment is disclosed in a schematic side view in FIG. 17*c*.

FIG. 19*d* shows a cross-section of the prosthetic elongated portion comprising two recesses 2203*a* and 2203*b* or adaptations, into which a prosthetic replacement for the acetabulum can enter for further increasing the motion range of the prosthetic hip joint in the directions of the recesses or adaptations. This embodiment is disclosed in a schematic side view in FIG. 17*c*.

FIG. 19*e* shows a cross-section of the prosthetic elongated portion wherein the restricting portion of the elongated portion has a narrow square cross-section such that for increasing the motion range of the prosthetic hip joint more in the directions of the sides of the square cross-section of the restricting portion of the elongated portion. This embodiment is disclosed in a schematic side view in FIG. 17*c*.

FIG. 19*f* shows a cross-section of the prosthetic elongated portion wherein the restricting portion of the elongated portion is more narrow that other portions of the elongated portions and eccentrically placed in relation to the caput and collum center axis. The eccentric placement of the restricting portion of the elongated portion increases the motion range of the prosthetic hip joint in the direction of the recess created by the narrow portion being placed eccentrically. This embodiment is disclosed in a schematic side view in FIG. 17*b*.

FIG. 19*g* shows a cross-section of the prosthetic elongated portion similar to the embodiment shown in FIG. 6*f*. However in the embodiment shown in FIG. 19*g* the narrow portion of the elongated portion is placed further eccentrically, further increasing the motion range of the prosthetic hip joint in the direction of the recess created by the narrow portion being placed eccentrically.

FIG. 19*h* shows a cross-section of the prosthetic elongated portion in which a portion of the elongated portion comprises a plurality of recesses 2203 which are adapted to a particular prosthetic replacement for the acetabulum. According to the embodiment shown in FIG. 19*h* the restricting portion is adapted for a prosthetic replacement for the acetabulum comprising extending portions with a circular surface entering the recess of the elongated prosthetic portion.

FIG. 19*i* shows a cross-section of the prosthetic elongated portion, wherein said cross section is a more narrow elliptically shaped cross section 2220 which enables further movement of the prosthetic replacement for the acetabulum 65 in the narrow direction of the elliptically shaped elongated portion.

FIG. 19*j* shows a cross-section of the prosthetic elongated portion in which a portion of the elongated portion comprises two recesses 2203*a,b* which are adapted to a particular prosthetic replacement for the acetabulum. According to the embodiment shown in FIG. 19*h* the restricting portion is adapted for a prosthetic replacement for the acetabulum comprising extending portions with a circular surface entering the recess of the elongated prosthetic portion.

FIG. 19*k* shows a cross-section of the prosthetic elongated portion in an embodiment similar to the embodiment shown in FIG. 19*j*, however, in the embodiment of FIG. 19*k* the recesses 2203*a,b* are somewhat eccentrically placed in relation to the caput and collum center axis. The eccentrically placed recesses 2203*a,b* thus altering the directions in which the motion range are further increased, such that the recesses could be adapted to more critical motions that a patient is interesting in doing.

FIG. 20*a* shows the prosthetic elongated portion 2201, also shown in FIG. 19*h*, when placed in the prosthetic replacement for the acetabulum 65 in a cross-sectional view, and in a side view. In the embodiment of FIG. 20*a*, the prosthetic replacement for the acetabulum surface comprises four extending portions 1823*a,b,c,d* clasping the prosthetic spherical portion 45 when implanted in the functional position in the hip joint. Each of the extending portions 1823*a, b,c,d* of the prosthetic replacement for the acetabulum has a rounded shape adapted to match corresponding rounded recesses of the elongated portion 2201. By the extending portions 1823*a,b,c,d* of the prosthetic acetabulum 65 entering the rounded recesses of the elongated portion 2201 the motion range of the prosthetic replacement for the acetabulum 65 is further increased.

FIG. 20*b* shows the prosthetic elongated portion 2201, also shown in FIG. 6*i*, when placed in the prosthetic replacement for the acetabulum 65 in a cross-sectional view, and in a side view. In the embodiment of FIG. 20*b*, the prosthetic replacement for the acetabulum surface comprises two rounded extending portions 1823*c,d* clasping the prosthetic spherical portion 45 when implanted in the functional position in the hip joint. The cross section of the prosthetic elongated portion is a more narrow, elliptically shaped cross section which enables further movement of the prosthetic replacement for the acetabulum 65 in the narrow direction of the elliptically shaped elongated portion, where according to this embodiment, the extending portions of the prosthetic acetabulum is placed.

FIG. 20*c* shows the prosthetic elongated portion 2201, also shown in FIG. 6*j*, when placed in the prosthetic replacement for the acetabulum 65 in a cross-sectional view, and in a side view. In the embodiment of FIG. 20*c*, the prosthetic replacement for the acetabulum surface comprises two rounded extending portions 1823*c,d* clasping the prosthetic spherical portion 45 when implanted in the functional position in the hip joint. The two extending portions 1823*c,d* of the prosthetic replacement for the acetabulum has a rounded shape adapted to match corresponding rounded recesses of the elongated portion 2201. The shape of the prosthetic replacement for the acetabulum 65 is so adapted that the prosthetic replacement for the acetabulum can move along a relatively large motion range whilst the extending portions still clasping the prosthetic spherical portion 45.

FIG. 20*d* shows the prosthetic elongated portion 2201, also shown in FIG. 19*k*, when placed in the prosthetic replacement for the acetabulum 65 in a cross-sectional view, and in a side view. In the embodiment of FIG. 20*d*, the prosthetic replacement for the acetabulum surface comprises two rounded extending portions 1823*c,d*, and one circumferentially elongated extending portion 1823*b* clasping the prosthetic spherical portion 45 when implanted in the functional position in the hip joint. The two extending portions 1823*c,d* of the prosthetic replacement for the acetabulum has a rounded shape adapted to match corresponding rounded recesses of the elongated portion 2201. The third extending portion 1823*b* is not extending as far as the two 1823*c* and 1823*d*, thus not limiting the motion range as much. The shape of the prosthetic replacement for the acetabulum 65 is so adapted that the prosthetic it can move along a relatively large motion range whilst the extending portions still clasping the prosthetic spherical portion 45.

Figure 21A:
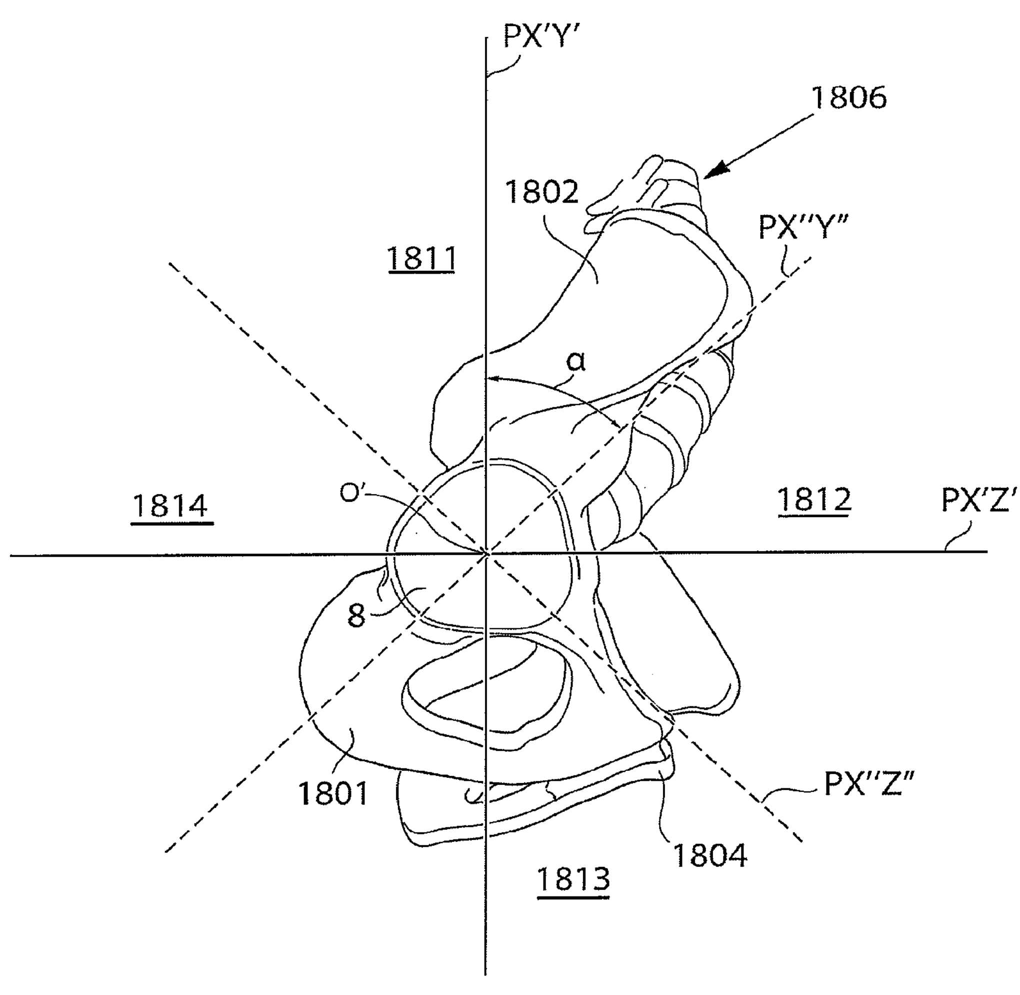
FIG. 21*a* shows pelvis in a lateral view.

FIG. 21*a* shows pelvis in the same view as FIG. 2*b*. Here the vertical and horizontal acetabulum planes PX'Y' and PX'Z' (further disclosed with reference to FIG. 2*d*) are shown in a strict plane view. Two further planes PX"Y" is introduced in FIG. 3, which planes are rotated an angle α of 45° clockwise. The planes PX"Y" and PX"Z", in accordance with the planes PX'Y' and PX'Z' divides the acetabulum bowl into four different quadrants, being a proximal quadrant 1811, a frontal quadrant 1812, a distal quadrant 1813 and a dorsal quadrant 1814.

Figure 21B:
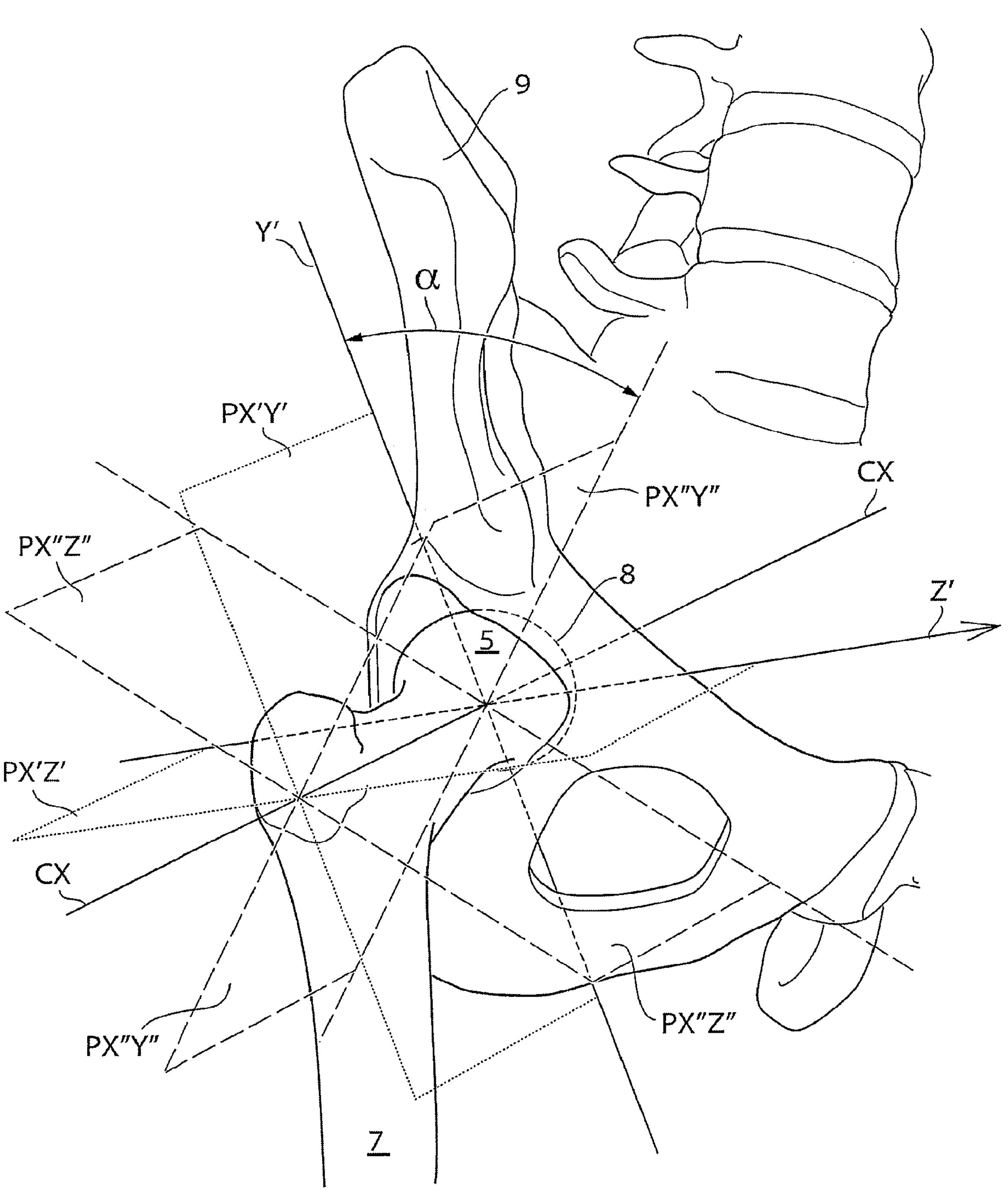
FIG. 21*b* shows the hip joint in section.

FIG. 21*b* shows a perspective view of the hip joint in section, displaying the horizontal and vertical planes PX'Y' and PX'Z' originating from the caput 5 and collum 6 center axis CX and dividing the caput 5 and collum 6 femur into quadrants. FIG. 21*b* further shows the planes PX"Y" and PX"Z" dividing the acetabulum bowl into four different quadrants, being a proximal quadrant 1811, a frontal quadrant 1812, a distal quadrant 1813 and a dorsal quadrant 1814, which is further disclosed with reference to FIG. 3*a*.

Figure 22A:
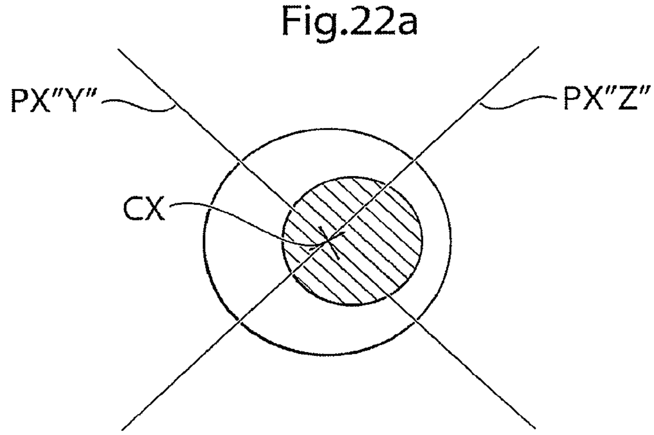
FIG. 22*a*-22*c* shows cross-sections of the medical device.

FIG. 22*a* shows a cross-section of an embodiment of the prosthetic elongated portion 2201, wherein said elongated portion is eccentrically placed in relation to the collum and caput center axis CX. The eccentric placement of the elongated portion 2201 places a large portion of the elongated portion 2201*a* in the dorsal quadrant, smaller portions of the elongated portions 2201*b,d* in the proximal and distal quadrants, respectively, and a smaller portion 2201*c* is placed in the frontal quadrant. The placing of a larger portion of the restricting portion of the elongated portion 2201 in the dorsal quadrant 1814 limits the motion range in the extension mostly. The movement range of the extension movements is less critical than for example flexion for every day activities, thus placing the major part of the elongated portion 2201*a* in the dorsal quadrant restricts the motion range needed in a less critical way. The eccentrically placed elongated portion is further disclosed with reference to FIGS. 19*f* and 19*g*.

Figure 22B:
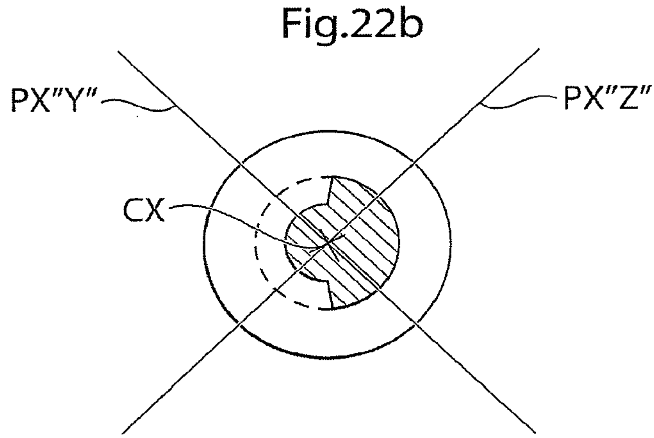

FIG. 22*b* shows a cross-section of an embodiment of the prosthetic elongated portion 2201, wherein said elongated portion comprises a recess 2203, mainly placed in the frontal 1812, proximal 1811 and distal 1813 quadrant, thus placing the major portion of the restricting portion of the elongated member in the dorsal quadrant 1814. The placing of a larger portion of the restricting portion of the elongated portion 2201 in the dorsal quadrant 1814 limits the motion range in the extension mostly. The movement range of the extension movements is less critical than for example flexion for every day activities, thus placing the major part of the elongated portion 2201*a* in the dorsal quadrant restricts the motion range needed in a less critical way. The elongated portion comprising a recess is further disclosed with reference to FIGS. 17*b* and 19*b*.

Figure 22C:
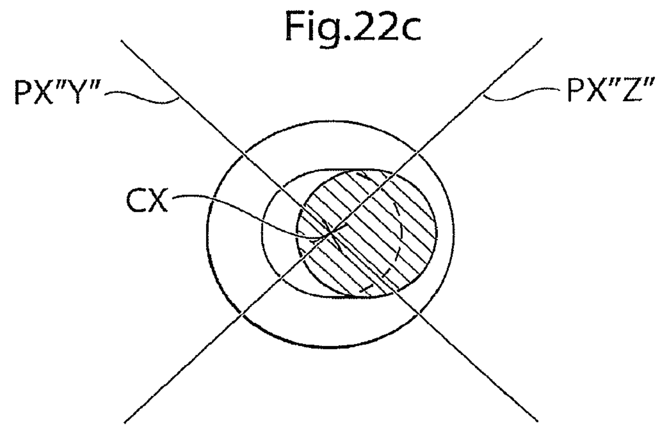

FIG. 22*c* shows a cross-section of an embodiment of the prosthetic elongated portion 2201, wherein said elongated portion 2201 is curved such that the connecting area between the prosthetic spherical portion 45 and the prosthetic elongated portion 2201 is eccentrically placed in relation to the caput and collum center axis CX, thus placing the major portion of the restricting portion of the elongated member 2201 in the dorsal quadrant 1814. The placing of a larger portion of the restricting portion of the elongated portion 2201 in the dorsal quadrant 1814 mainly limits the motion range in extension of the leg. The movement range of the extension movements is less critical than for example flexion for every day activities, thus placing the major part of the elongated portion 2201*a* in the dorsal quadrant restricts the motion range needed in a less critical way. The elongated portion comprising the curved elongated portion is further disclosed with reference to FIG. 17*d*.

Figure 23:
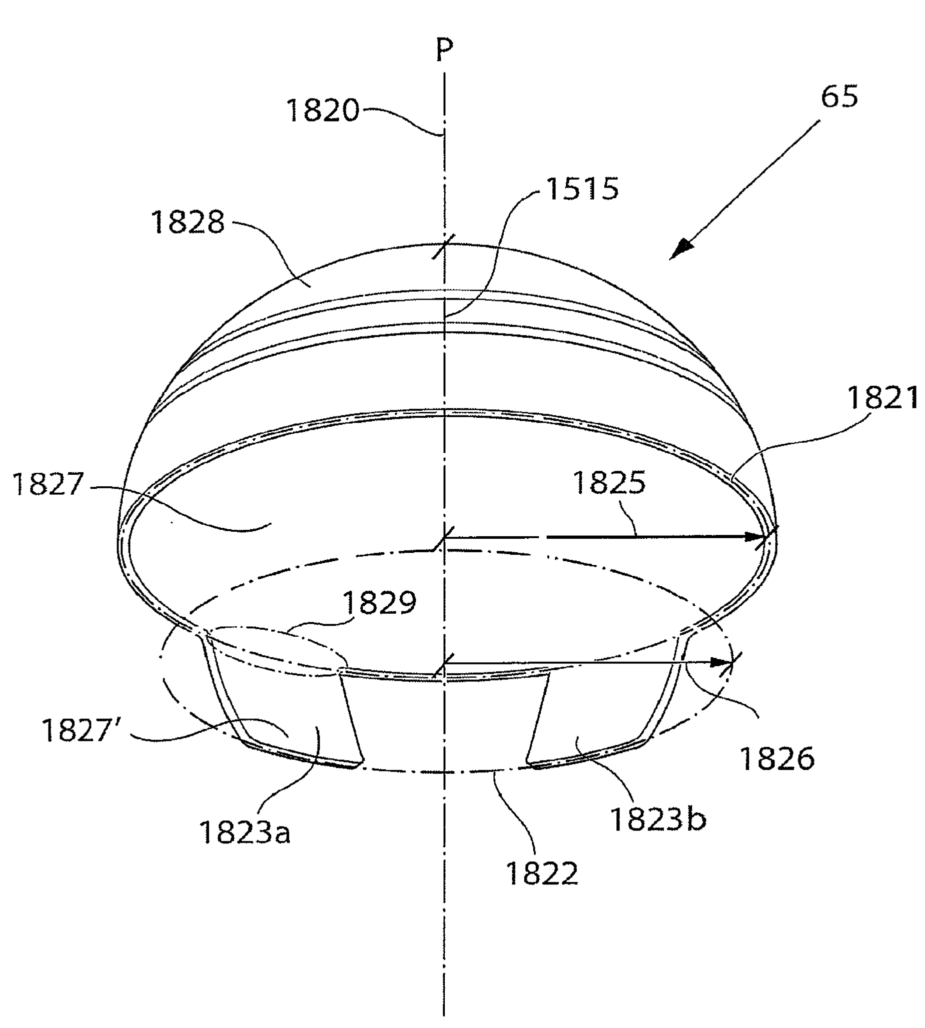
FIG. 23 shows a prosthetic replacement for the acetabulum, according to one embodiment.

FIG. 23 shows a medical device for implantation in a hip joint of a patient. The medical device is adapted to be fixated to the femoral bone of the patient, for example by means of an adhesive, such as bone cement, or mechanical fixating members, such as orthopedic screws. The medical device comprises an inner 1827 and an outer 1828 surface. A contacting portion of the inner surface 1827 is spherical and faces the center of the hip joint, when the medical device is implanted. The inside of the medical device is adapted to receive a prosthetic replacement for a caput femur having a spherical portion, and the spherical contacting portion of the inner surface 1827 is adapted to be in contact with a spherical portion of the outer surface of the prosthetic replacement of the caput femur. The medical device, according to the embodiment shown in FIG. 17 comprises two extending portions 1823*a,b*, extending the contacting portion of the inner surface 1827' such that the extending portions 1823*a,b* clasps the spherical portion of a prosthetic replacement of a caput femur, for restraining the spherical portion in the medical device. The medical device is adapted to receive the prosthetic spherical portion, connected to the prosthetic elongated portion. The inner surface 1827 comprises an equator line 1821, being the largest circular circumference of the inner surface. The two extending portions passes beyond the equator line 1821, such that an end portion 1829 of the contacting portion, here being of the extending portion 1823*b* of the inner surface 1827, forms a circular extension line 1822 placed proximal to the equator line 1821, when the medical device is implanted, and having a smaller circumference than the equator line 1821; thus a distance 1826 between a center axis P of the medical device and the extension line 1822 is shorter than a distance 1825 between the center axis P and the equator line 1821.

Figure 24:
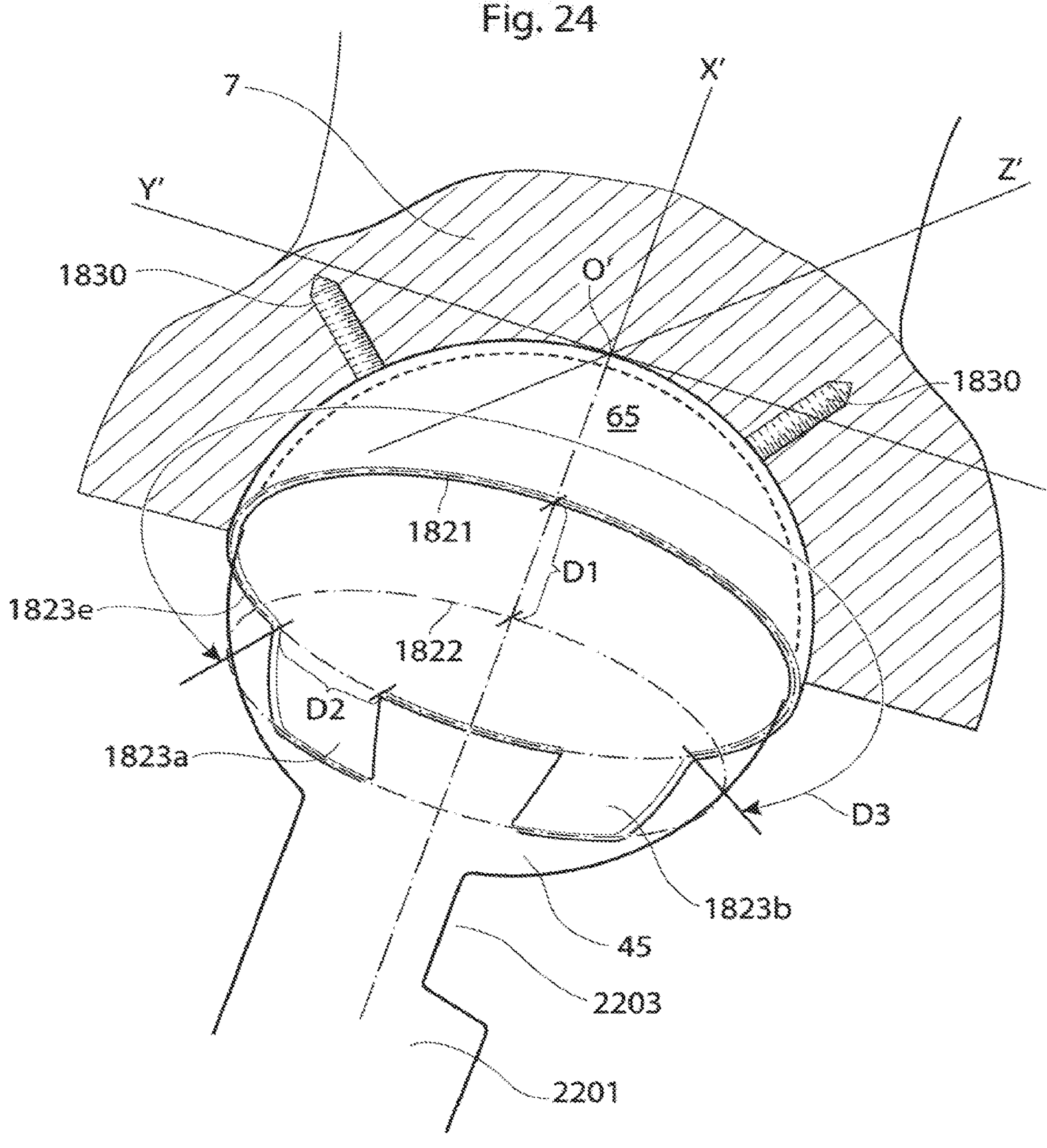
FIG. 24 shows the hip joint in section, when a prosthetic replacement for the acetabulum, and a medical device has been implanted.

FIG. 24 shows the medical device described with reference to FIG. 23 when implanted. According to this embodiment the medical device is adapted to be fixated using orthopedic screws 1830, mechanically fixating the medical device to the femoral bone 5, by the medical device comprising holes through which the screws 1830 are placed. In FIG. 5 the contacting portion of the inner surface 1827 has been placed in contact with the prosthetic spherical portion being connected to a the prosthetic elongated portion 2201, the prosthetic spherical 45 and elongated portions 2201 replacing the proximal portion of the femoral bone. The two extending portions 1823*a* and 1823*b* extending the contacting portion of the inner surface and clasping the spherical portion 45, for restraining the spherical portion in the medical device. The inner surface comprising the equator line 1821, and the extending portions 1823*a,b* passing beyond the equator line 1821 and comprising the more proximal extension line 1822 having a smaller circumference than the equator line 1821. The more proximal extension line 1822 being placed at a distance D1 from the equator line 1821. According to this embodiment the extension line 1822 is parallel to the equator line 1821, however this is not necessarily so in other embodiments. The extension portion 1823*a* according to the embodiment shown in FIG. 11 extends circumferentially along the equator line, a distance D2. Along another portion of the equator line, a distance D3, there are no extending portion, at a second portion 1823*e*, which enables the elongated portion 2201 to enter the space between the first and second extending portions 1823*a,b* which creates a larger movement range of the hip joint, for further increase of the movement range, the recess 2203 in the elongated portion 2201 is adapted for some section of the extending portion to enter the recess 2203.

The extending portion, according to any of the embodiments, adapted to clasp the prosthetic spherical portion, for restraining it the prosthetic acetabulum 65, could further be adapted to release the prosthetic spherical portion 45 when a large enough strain is placed on the joint. This feature enables the prosthetic spherical portion to be fixedly attached in the prosthetic acetabulum 65 in normal use, and be released from the prosthetic acetabulum, e.g. in case of an accident, thus reducing the risk of damaging the bodily structures, such as the femoral bone, or the fixations between bodily structures and prosthetic parts.

According to one embodiment, the extending elements, are placed such that the extending elements restricts the motion range minimally, or in ways which are not limiting the motion range used in everyday life. This is enabled through the placing of the extending portions, or the interaction between the extending portion and adaptations of the prosthetic elongated portion. The hip joint is a synovial ball and socket joint which permits a large motion range for allowing a plurality of different movements of the lower limb. From a neutral position, the following movements of the hip joint are normally possible: Lateral or external rotation, 30° with the hip extended, 50° with the hip flexed, medial or internal rotation 40°, extension or retroversion 20°, flexion or anteversion 140°, abduction 50° with hip extended, 80° with hip flexed, adduction 30° with hip extended, 20° with hip flexed. In the movement ranges of abduction and adduction the depth of the acetabulum bowl and thus the extending portions does not restrict the motion range in a critical way since the motion range of the normal hip is restricted in these movements, in normally agile persons, by the muscles, tenors and ligaments surrounding the hip joint.

Figure 25A:
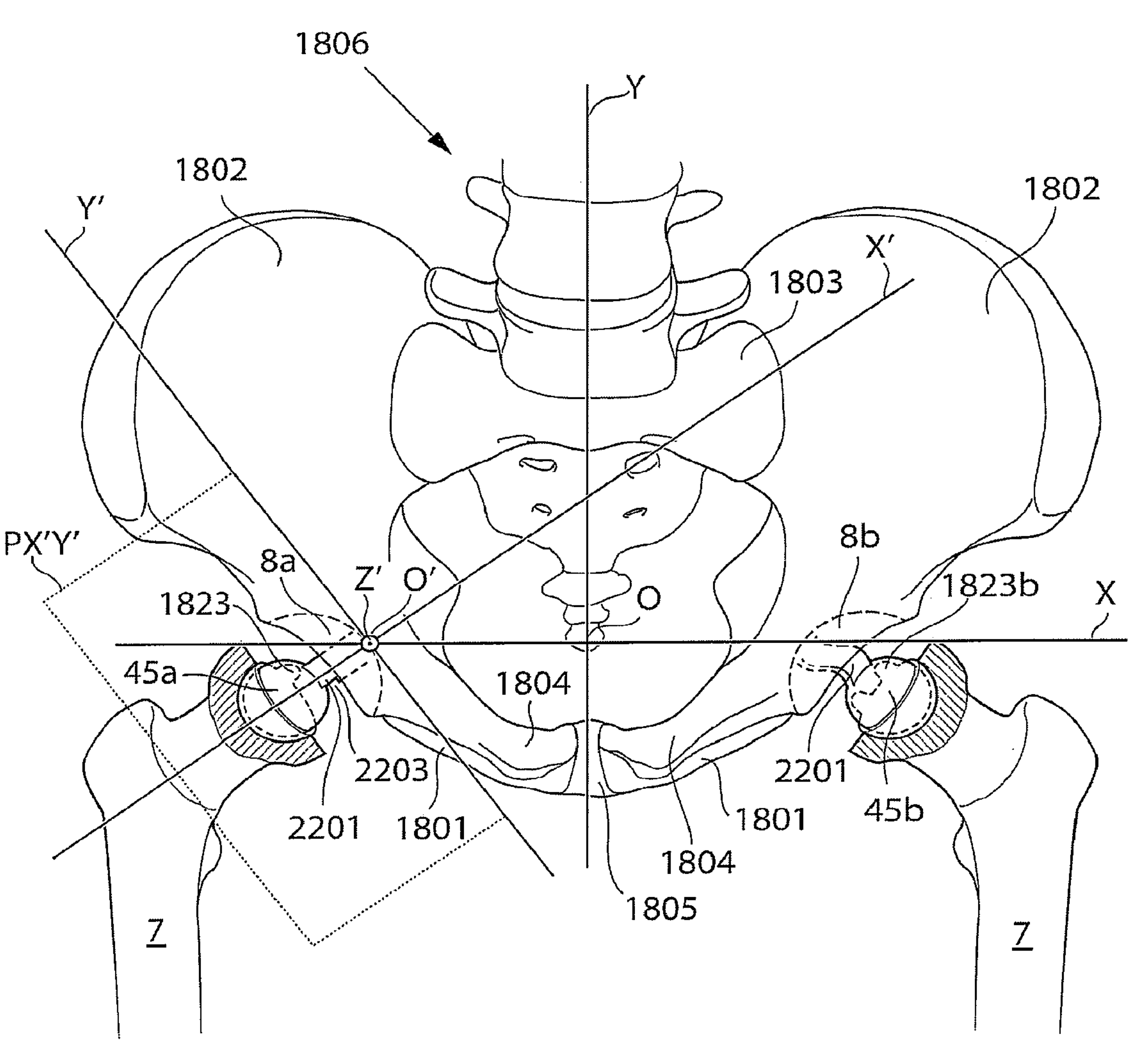
FIG. 25*a* shows the pelvic region in a frontal view.

FIG. 25*a* shows a frontal view of pubis and the proximal portions of the femoral bones 7 when two embodiments prosthetic replacement for the acetabulum 65 has been implanted in the hip joint. The prosthetic replacements for the acetabulum shown comprises one extending portion 1823, here placed dorsal to the vertical acetabulum plane PX'Y' in the base position, thus only partially limiting abduction in far excess of 50°. According to the embodiment shown, the extending portion 1823 extends circumferentially along the equator line 1821 about 1/10 of the length of the equator line 1821, however in other embodiments the extending portion 1823 extends along as much as half of the length of the equator line 1821, and in other embodiments the extending portion 1823 extends as little as about 1/30 of the length of the equator line 1821. The prosthetic replacement for the acetabulum placed in the left femoral bone comprises two extending portions 1823*a,b*, both being placed dorsal the corresponding vertical acetabulum plane PX'Y' of the left acetabulum (not shown) in the base position, thus limiting the motion range of the hip joint in a non restrictive way, in relation to everyday activities. In both the right and left embodiment the extending portions 1823 extends discontinuously along the equator line 1821 thus enabling the elongated portion 2201 to partially be placed between the equator line and the extension line, and in the left embodiment, be placed between the extending portions 1823*a,b* thus entering the cavity between the extending portions 1823*a,b*. The recess 2203 of the prosthetic elongated portion 2201 implanted in the right hip joint is radially placed, in relation to the caput and collum center axis, such that the a section of the prosthetic elongated portion 2201, can enter the recess for further increasing the movement range of the prosthetic acetabulum surface 65 in relation to the elongated 2201 and spherical 45*a* portion. The curving of the prosthetic elongated portion 2201 implanted in the left hip joint is radially placed, in relation to the caput and collum center axis, for further increasing the movement range of the prosthetic acetabulum surface 65 in relation to the elongated 2201 and spherical 45*b* portion.

Figure 25B:
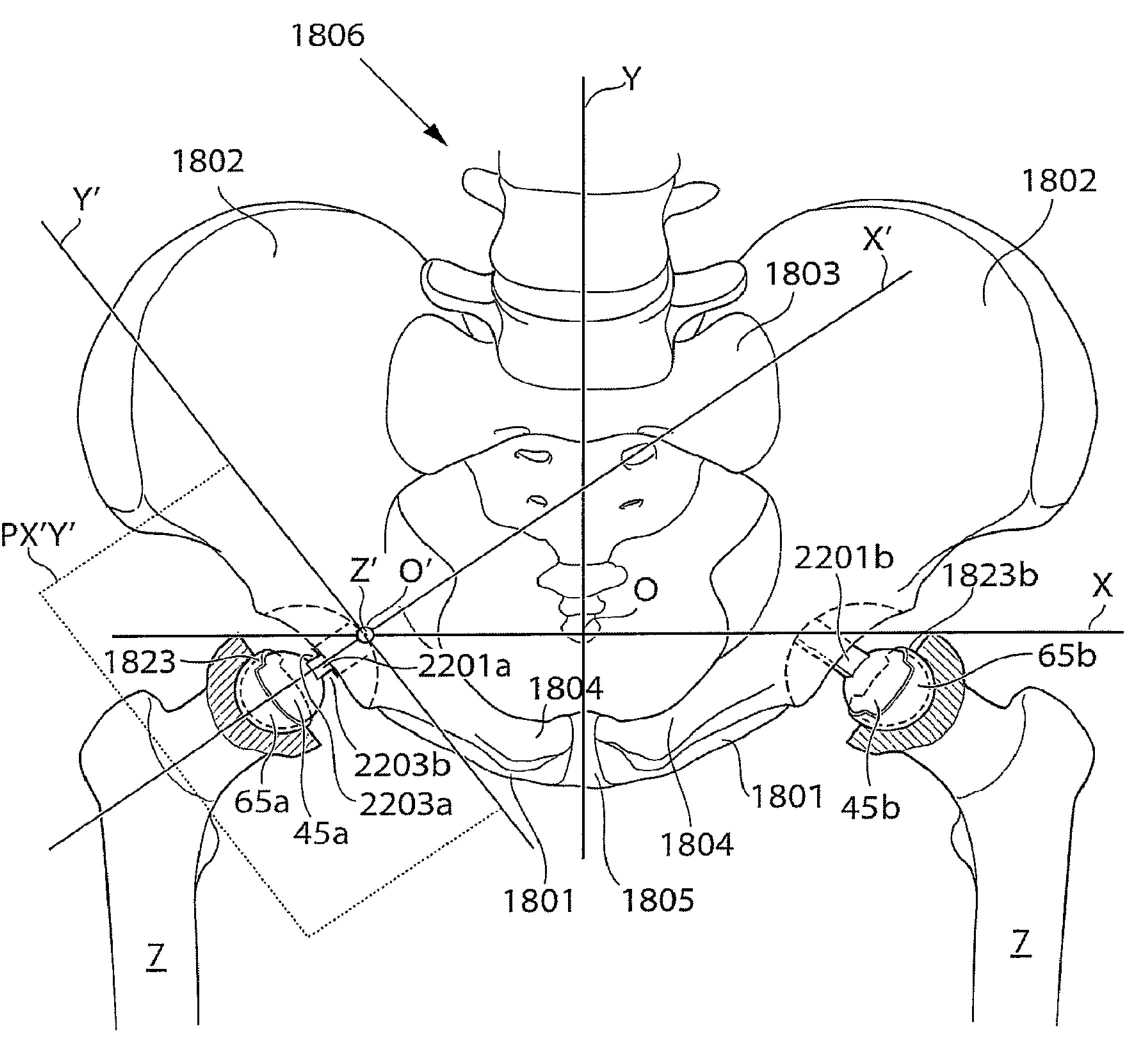
FIG. 25*b* shows the pelvic region in a frontal view.

FIG. 25*b* shows a frontal view of pubis and the proximal portions of the femoral bones 7, when two further embodiments of the prosthetic replacements have been implanted. The embodiment shown placed on the right side is an embodiment in which the prosthetic elongated portion 2201*a* comprises a first 2203*a* and second 2203*b* recess placed at the restricting portion of the elongated portion 2201*a*. The prosthetic elongated portion is connected to a prosthetic spherical portion 45*a* which is restrained in a prosthetic replacement for the acetabulum 65*a* fixated to the femoral bone. The prosthetic replacement for the acetabulum 65*a* comprises extending portions 1823 clasping the prosthetic spherical portion 45*a* and thus restraining the spherical portion in the prosthetic replacement for the acetabulum 65*a*. The extending portions 1823 is placed in the proximal quadrant in the base position, thus limiting the motion range of the hip joint in a non restrictive way, in relation to everyday activities. According to the embodiment shown, the extending portion 1823 extends circumferentially along the equator line 1821 about 1/10 of the length of the equator line 1821, however in other embodiments the extending portion 1823 extends along as much as half of the length of the equator line 1821, and in other embodiments the extending portion 1823 extends as little as about 1/30 of the length of the equator line 1821. The prosthetic elongated portion 2201*b* shown placed in the left hip joint comprises a narrow portion connected to the prosthetic spherical portion 45*b*. The narrow portion enables a relatively large motion range in relation to the elongated portion even though the prosthetic replacement for the acetabulum comprises extending portions 1823*a,b* extending beyond the equator line of the prosthetic spherical portion 45*b*, thus clasping the spherical portion and restraining it in a fixated position.

Figure 26:
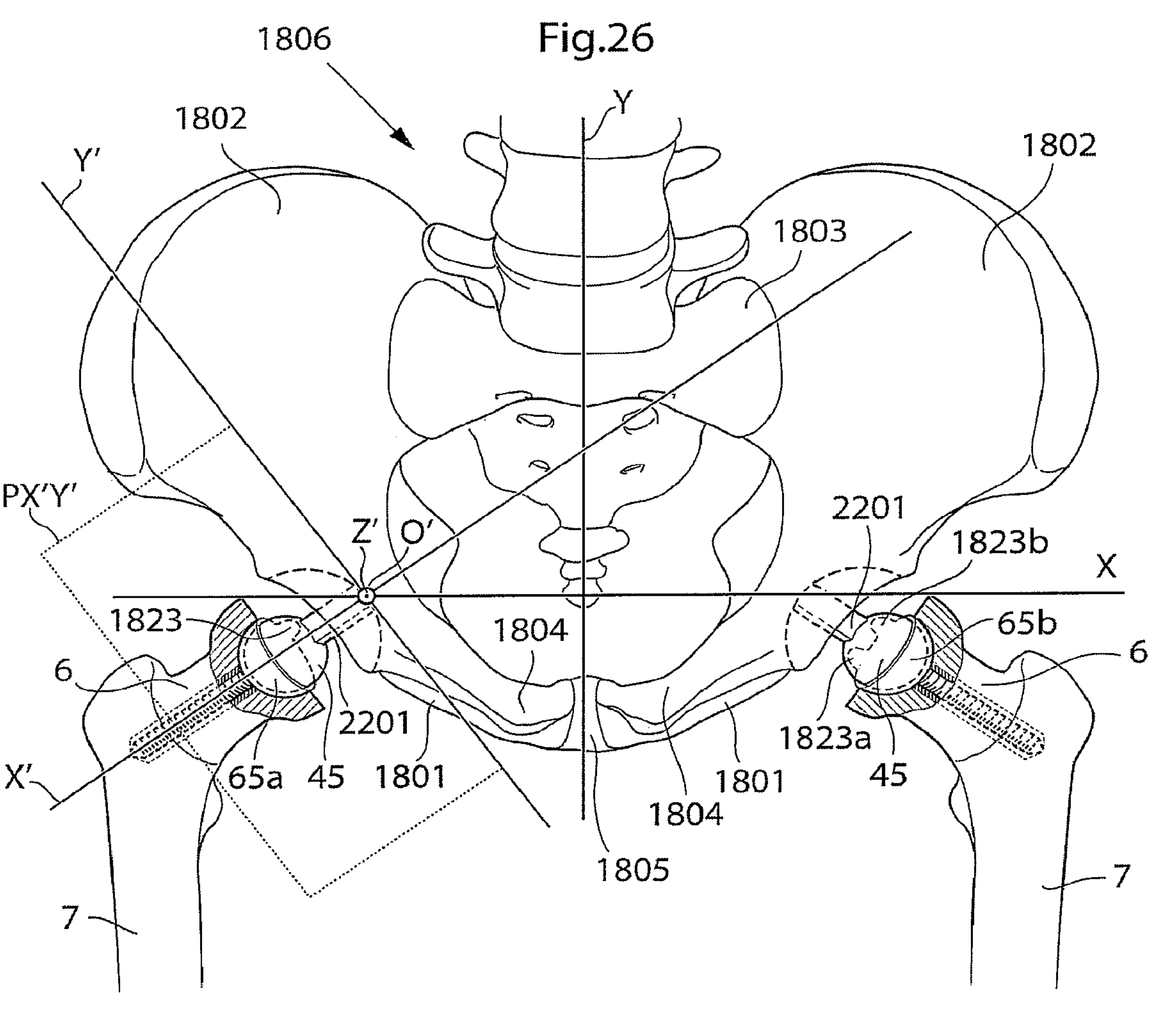
FIG. 26 shows the pelvic region in a frontal view.

FIG. 26 shows the pelvis and the proximal portions of the femoral bones 7 including the embodiment of FIG. 25*a*, with the difference that the natural caput femur and a portion of the natural collum femur has been replaced by a prosthetic replacement for the acetabulum. The prosthetic elongated portion 2201 is here coordinated with the extending portions 1823 of the prosthetic replacement for the acetabulum 65*a,b* for further improving the motion range of the hip joint, or not limiting the natural motion range of the hip joint.

Figure 27:
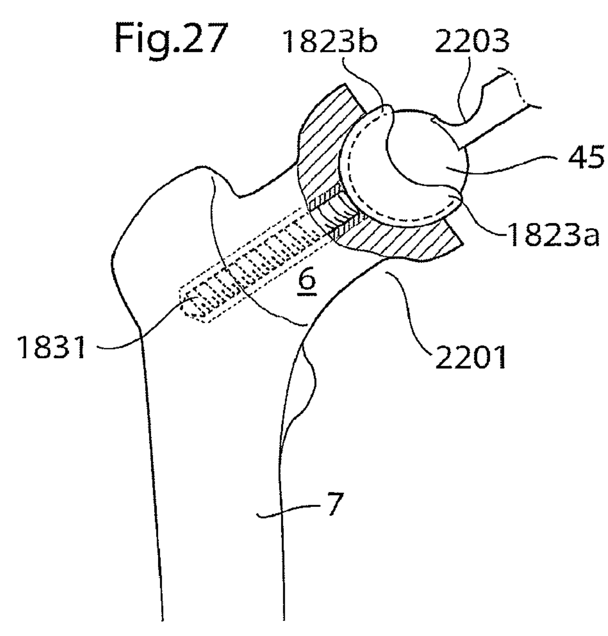
FIG. 27 shows a medical device placed in the femoral bone.

FIG. 27 shows the medical device according to an embodiment in which the medical device comprises two extending portions 1823*a,b*. The medical device is placed on a prosthetic elongated portion 2201, to which a prosthetic spherical portion 45 is attached. The prosthetic elongated member 2201 is here adapted to further improve the motion range of the hip joint, or not limiting the natural motion range of the hip joint, by the prosthetic elongated portion 2201 comprising a recess 2203 in which the extending portions 1823 can enter.

Figure 28A:
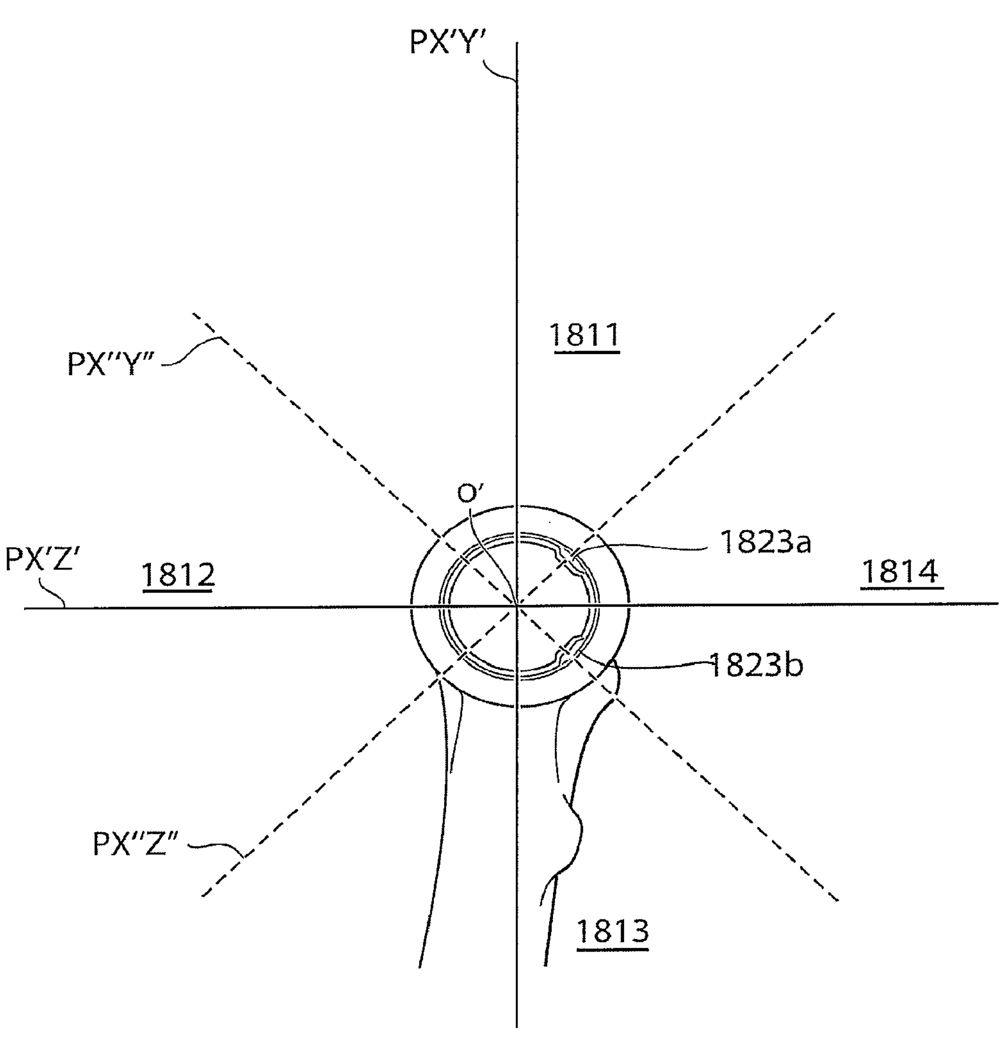
FIG. 28*a* shows the femoral bone in a lateral view.

FIG. 28*a* shows the pelvis in a lateral view, the prosthetic replacement for the acetabulum 65 in the femoral bone comprises two extending portions 1823*a,b*, both extending circumferentially along the equator line (as disclosed in for example FIG. 5) dorsal to the caudal-cranial axis Y when being in the base position and being adapted to clasp the caput femur or a prosthetic replacement therefor. The extending portions 1823*a,b* extending dorsal to the caudal-cranial axis Y when being in the base position and thus reducing the limiting effect that the extending portions 1823*a,b*, have on the motion range of the hip joint. According to the embodiment shown in FIG. 15*a* the extending portion 1823*a*, placed proximally in the acetabulum, extends circumferentially a distance of about ¼ of the length of the equator line, and the extending portion 1823*b*, placed distally in the acetabulum when being in the base position, extends circumferentially a distance of about 1/10 of the length of the equator line, however it is equally conceivable that this relationship is the other way around, or that any of the extending portions circumferentially extends a distance of as much as half of the length of the equator line, thus extending the entire distance of the equator line being dorsal to the vertical acetabulum plane PX'Y', or that any of the extending portions 1823*a,b* extends a distance being as little as 1/30 of the distance of the equator line. According to the embodiment shown in FIG. 15*a*, the first extending portion 1823*a* extends in distal-lateral direction from the acetabulum, and the second extending portion 1823*b* extends medially towards foramen obturatum when being in the base position.

Figure 28B:
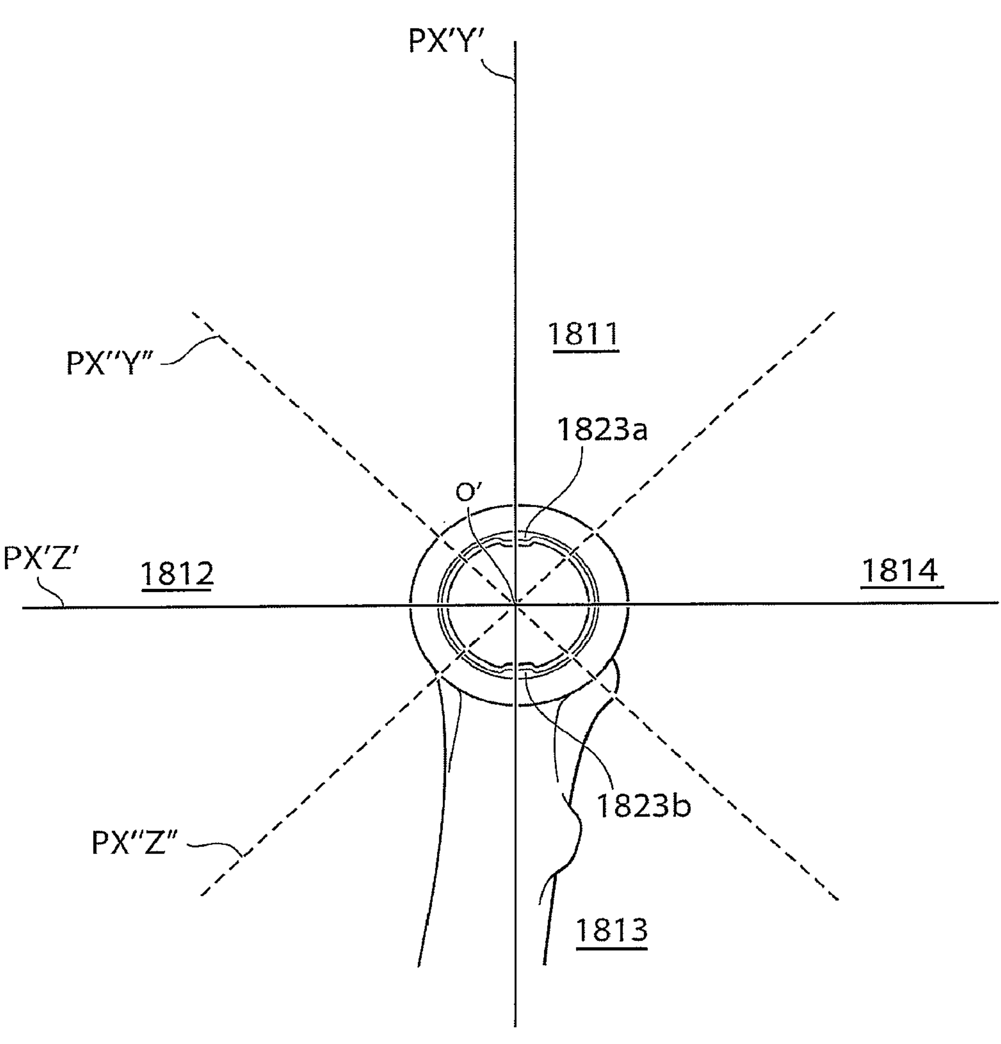
FIG. 28*b* shows the femoral bone in a lateral view.

FIG. 28*b* shows the pelvis in a lateral view, the prosthetic replacement for the acetabulum 65 in the femoral bone comprises two extending portions 1823*a,b*, the two extending portions 1823*a,b* extends in the proximal quadrant 1811 and the distal quadrant 1813 when being in the base position, respectively.

There are multiple ways in which the extending portions 1823 can be adapted to reduce the effects that the extensions have on the motion range of the hip joint.

Figure 29:
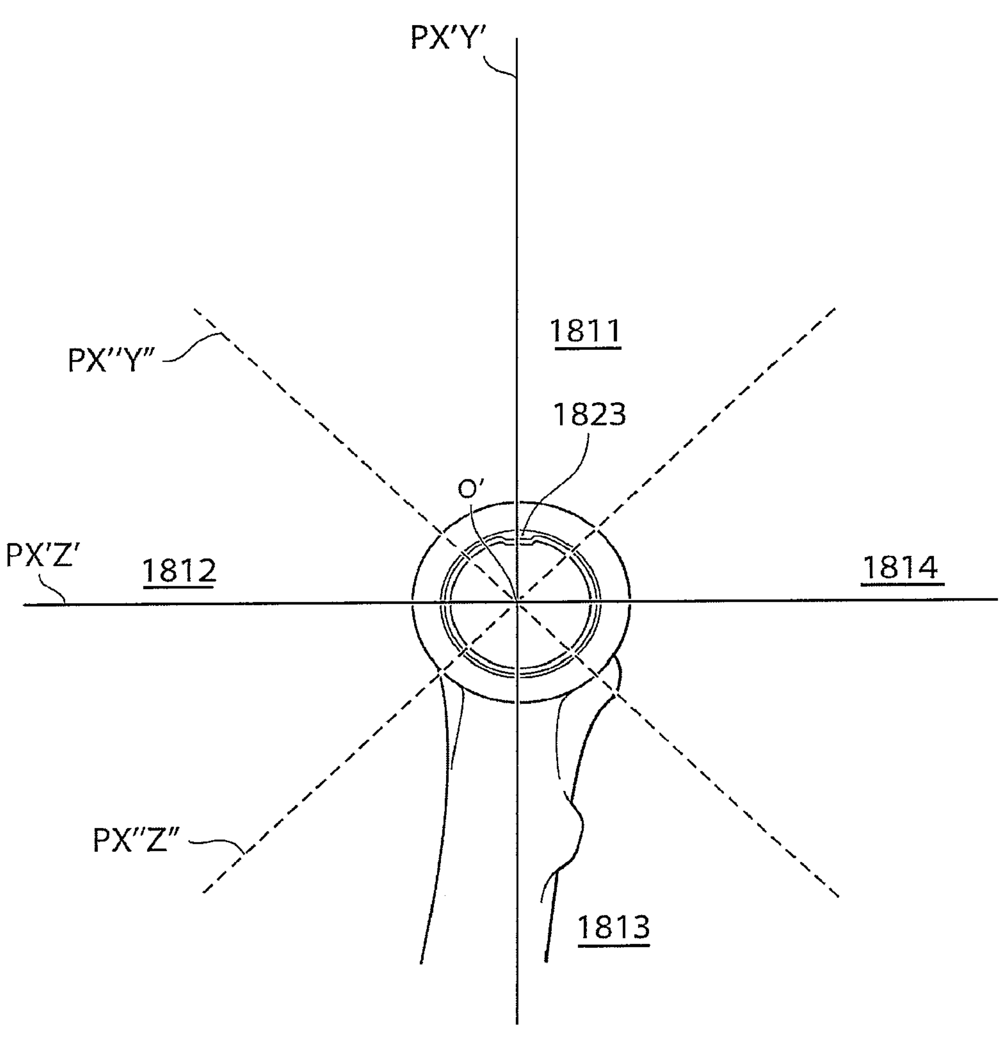
FIG. 29 shows the femoral bone in a lateral view.

FIG. 29 shows the pelvis in a lateral view, the prosthetic replacement for the acetabulum 65 in the femoral bone shown comprises one extending portion 1823 extending and being adapted to clasp the caput femur, or a prosthetic replacement therefor. The extending portion 1823 extends circumferentially along the equator line within the proximal quadrant 1811 when being in the base position, which is further disclosed with reference to FIG. 3. According to the embodiment shown in FIG. 10, the extending portion 1823 extends in distal-lateral direction from the acetabulum when being in the base position.

Figure 30:
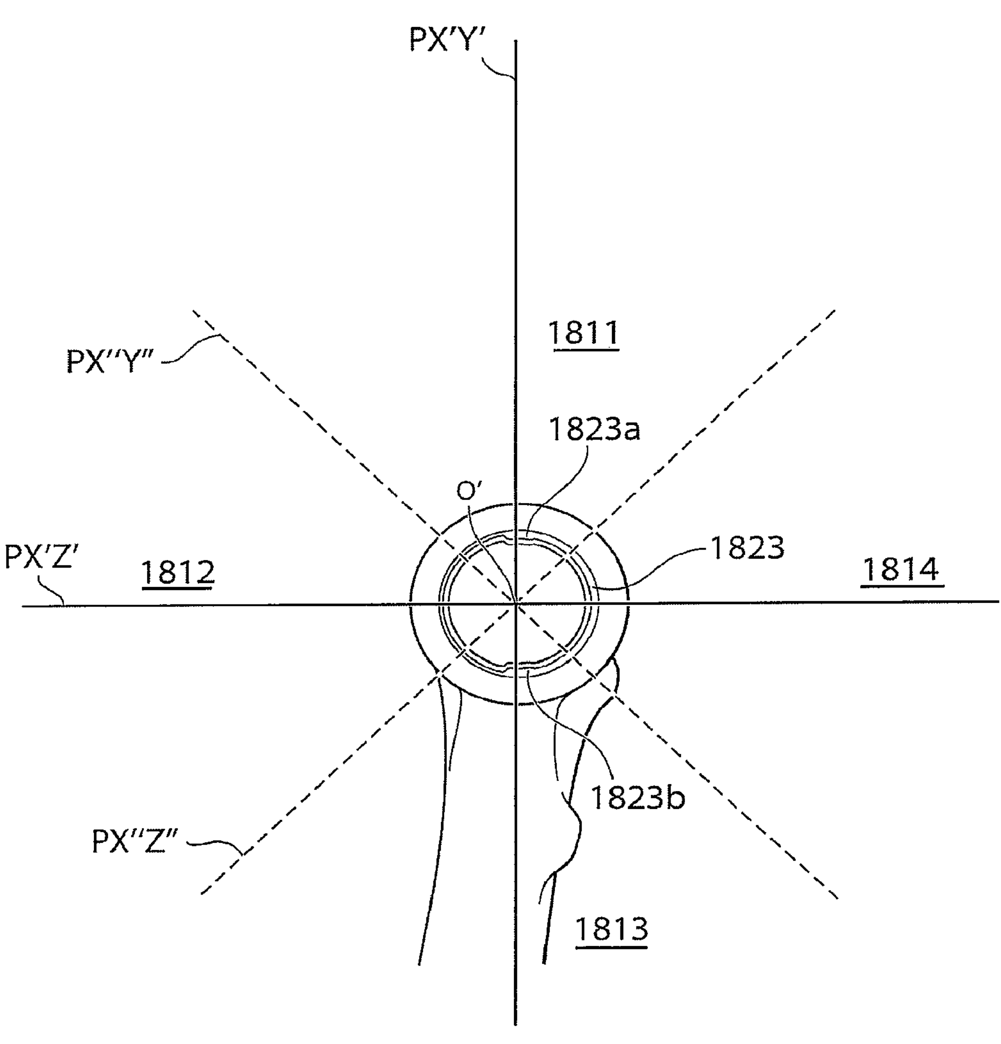
FIG. 30 shows the femoral bone in a lateral view.

FIG. 30 shows the pelvis in a lateral view, the prosthetic replacement for the acetabulum 65 in the femoral bone shown comprises a continuously extending portion 1823 with two extending portions 1823*a* and 1823*b* extending further in relation to the average extension of the extending portion. The entire extending portion is placed in the proximal, distal and dorsal quadrants and the extending portions 1823*a,b* extending further than the average extension of the extending portion 1823 extends in the proximal and distal quadrant when being in the base position.

Figure 31:
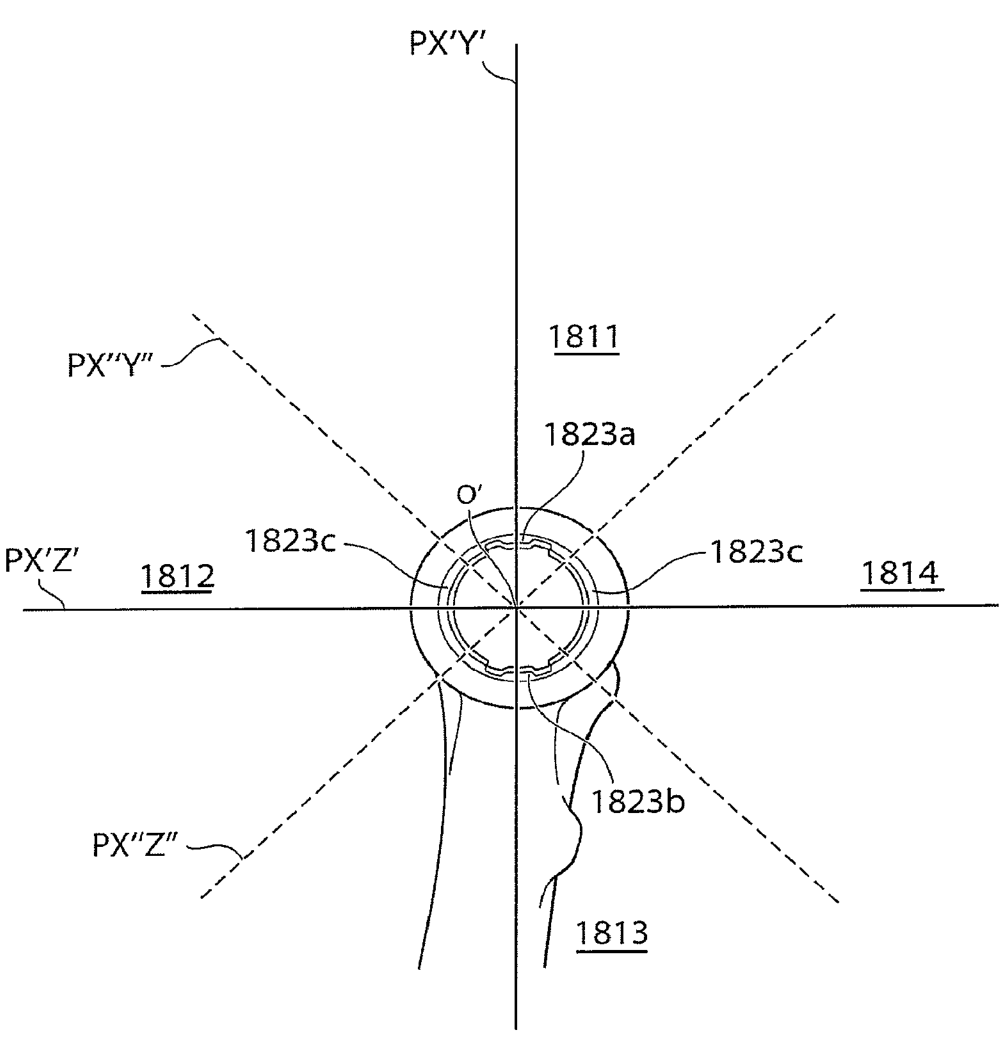
FIG. 31 shows the femoral bone in a lateral view.

FIG. 31 shows the pelvis in a lateral view, the prosthetic replacement for the acetabulum 65 in the femoral bone shown comprises four extending portions 1823*a,b,c,d*, wherein the first 1823*a* and second 1823*b* extending portions extends in the proximal and distal quadrant, respectively, thus the first extending portion 1823*a* extending in distal-lateral direction from the acetabulum, and the second extending portion 1823*b* extending medially towards foramen obturatum when being in the base position. The third extending portion 1823*c* when being in the base position extending in the frontal quadrant 1812, out from the acetabulum in dorsal direction, extends less than the first and second extending portion, since extending portions 1823*c* in the frontal quadrant is more limiting to the normal motion range of the hip joint. The fourth extending portion 1823*d* extends in the dorsal quadrant in accordance with the third extending portion 1823*c* do not extend as far as the first and second extending portions when being in the base position.

Figure 32:
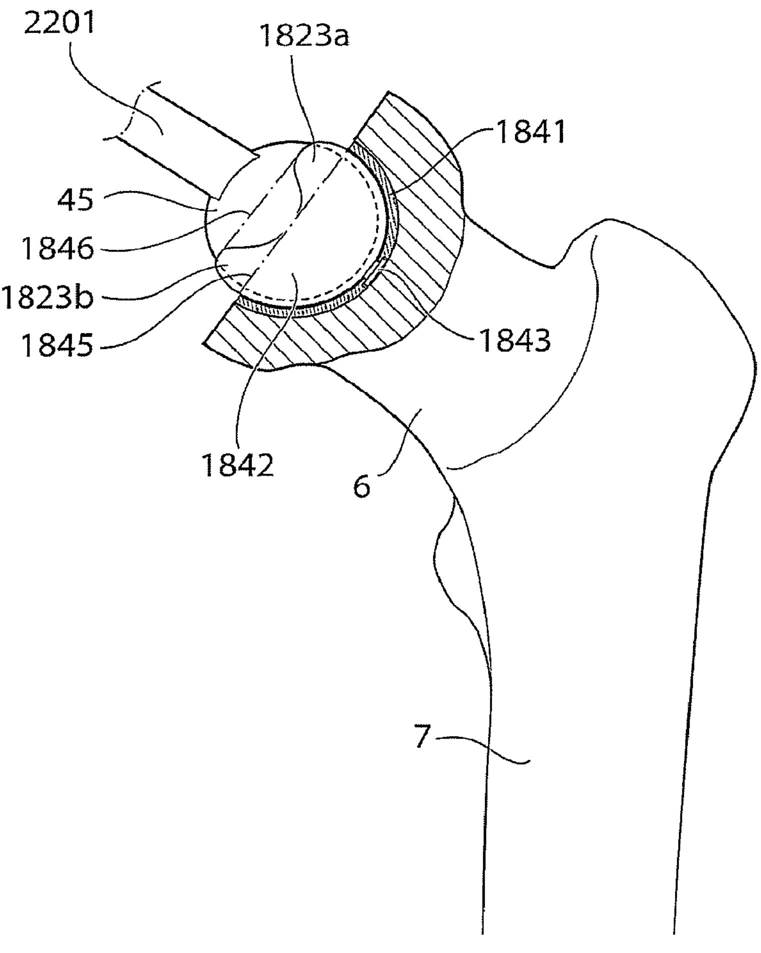
FIG. 32 shows a medical device placed in the femoral bone.

FIG. 32 shows an alternative embodiment of the prosthetic replacement for the acetabulum 65. In the alternative embodiment, the prosthetic replacement for the acetabulum 65 comprises a first part 1841 adapted to be fixated to the femoral bone of the patient. The first part comprises an inner contacting surface adapted to be in movable connection with an outer contacting surface of a second part 1842. The second part 1842 is rotatably fixated to the first part 1841 by a rotatable connecting member 1843. An outer contacting surface of a prosthetic spherical portion 45 is adapted to be placed in contact with the inner surface of the second part 1842 and be movable in multiple directions, thus replicating the natural ball and socket joint of the hip. The second part 1842 comprises two extending portions 1823*a,b* extending beyond the equator line 1845 of the second part 1842. The extending portions 1823*a,b* extends longitudinally discontinuously along the equator line, thus creating an area between the extending portions, in which area a portion of the prosthetic collum femur can be placed, thus being placed partially between the equator line 1845 and the extension line 1846. The construction shown in FIG. 26 enables the second part 1842 to rotate if the prosthetic elongated portion 2201 engages the extending portions 1823*a,b*, which are sloped for this purpose. This way the second part 1842 are always placed such that the prosthetic elongated portion 2201 can be placed partially between equator line 1845 and the extension line 1846, which creates an optimal range of movement whilst the second part clasps the prosthetic spherical portion 45, and thus restricting the spherical portion 45 in the second part 1842 of the prosthetic replacement for the acetabulum 65.

Figure 33A:
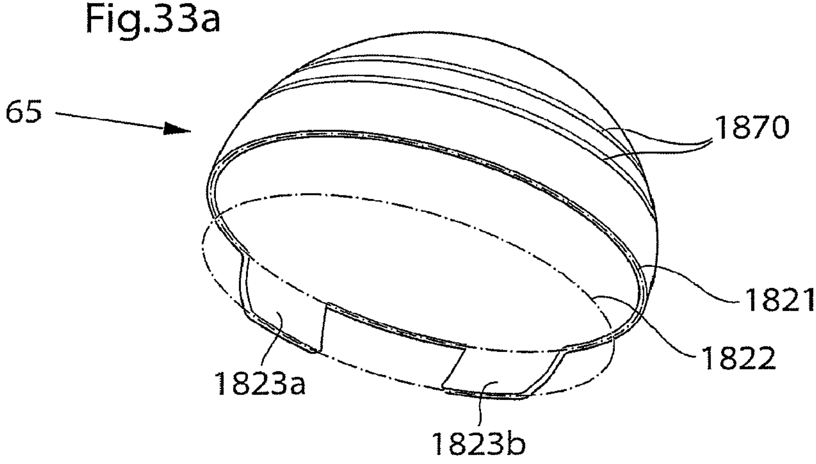
FIG. 33*a*-33*f* shows embodiments of prosthetic replacements for the acetabulum.

FIG. 33*a* shows the prosthetic replacement for the acetabulum 65 according to one embodiment. In this embodiment the prosthetic replacement for the acetabulum 65 comprises two extending portions 1823*a, b*. The prosthetic replacement for the acetabulum 65 is according to this embodiment adapted to be fixated to the femoral bone by means of an adhesive which is adapted to be placed in connection with the adhesive recesses 1870 of the outer surface of the prosthetic replacement for the acetabulum 65.

Figure 33B:
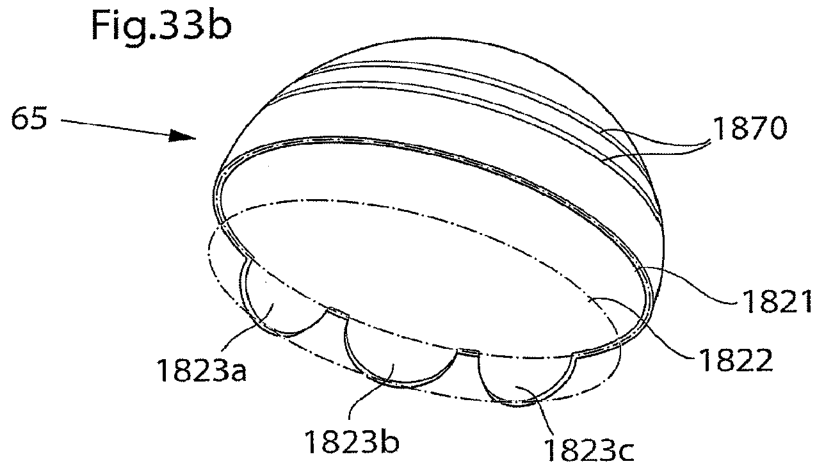

FIG. 33*b* shows a prosthetic replacement for the acetabulum 65 similar to the prosthetic replacement for the acetabulum 65 disclosed with reference to FIG. 33*a*, but with the difference that it comprises three equally extending portions 1823*a,b,c*.

Figure 33C:
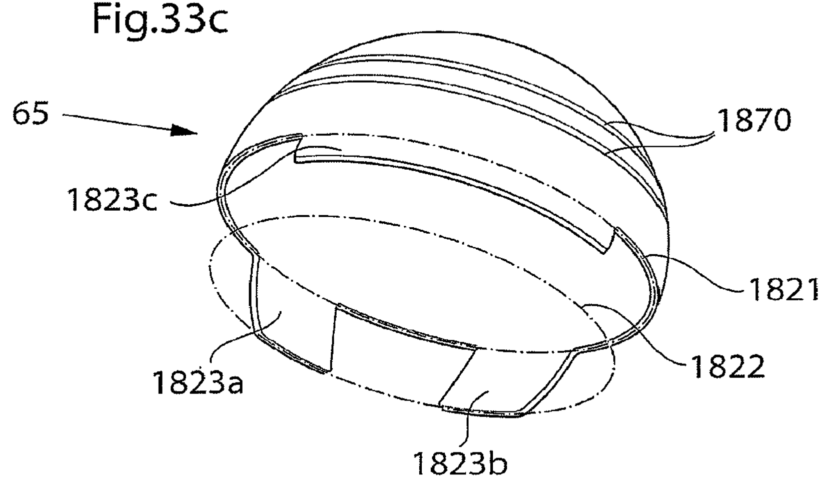

FIG. 33*c* shows a prosthetic replacement for the acetabulum 65, similar to the prosthetic replacement for the acetabulum 65 disclosed with reference to FIG. 33*a*, but with the difference that it comprises two equally extending portions 1823*a,b* and one less extending portion 1823*c*.

Figure 33D:
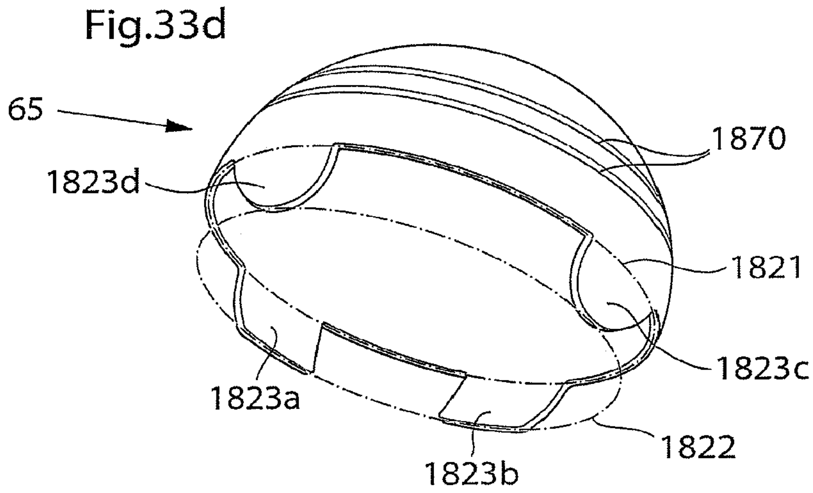

FIG. 33*d* shows a prosthetic replacement for the acetabulum 65 similar to the prosthetic replacement for the acetabulum 65 disclosed with reference to FIG. 33*a*, but with the difference that it comprises four equally extending portions 1823*a,b,c,d*.

Figure 33E:
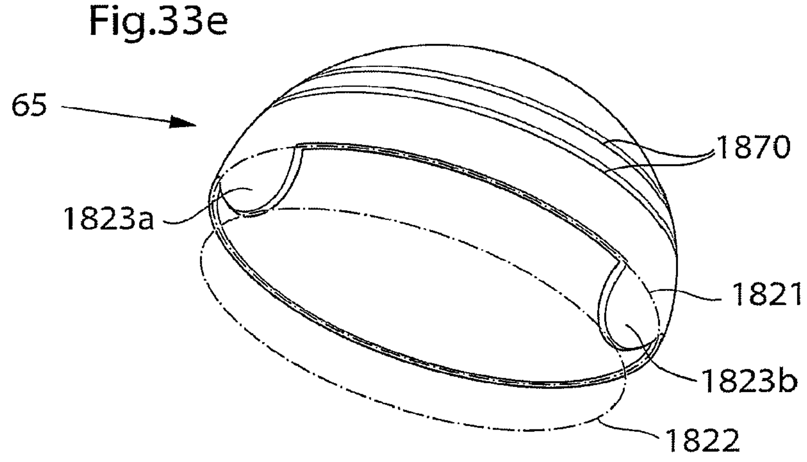

FIG. 33*e* shows a prosthetic replacement for the acetabulum 65 similar to the prosthetic replacement for the acetabulum 65 disclosed with reference to FIG. 33*a*, but with the difference that the two extending portions are placed further from each other, and thus being adapted to be placed in the proximal and distal quadrant, when implanted and being in the base position.

Figure 33F:
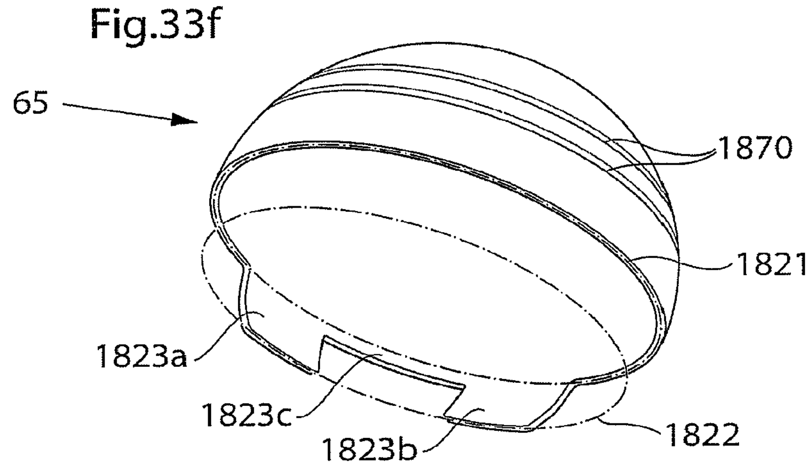

FIG. 33*f* shows a prosthetic replacement for the acetabulum 65 similar to the prosthetic replacement for the acetabulum 65 disclosed with reference to FIG. 33*a*, but further comprising a less extending portion 1823*c* placed between the first and second extending portions 1823*a,b*.

The extending portions of the prosthetic replacement for the acetabulum 65 which have been described could be made from an elastic material, enabling the extending portions to pass onto the a prosthetic spherical portion, according to any of the embodiments herein.

FIG. 34*a* shows the prosthetic elongated portion 2201, also shown in FIG. 7*a*, when placed in the prosthetic replacement for the acetabulum 65 in a cross-sectional view, and in a side view. In the embodiment of FIG. 34*a*, the prosthetic replacement for the acetabulum surface comprises four extending portions 1823*a,b,c,d* clasping the prosthetic spherical portion 45 when implanted in the functional position in the hip joint. Each of the extending portions 1823*a,b,c,d* of the prosthetic replacement for the acetabulum has a rounded shape adapted to match corresponding rounded recesses of the elongated portion 2201. By the extending portions 2823*a,b,c,d* of the prosthetic acetabulum 65 entering the rounded recesses of the elongated portion 2201 the motion range of the prosthetic acetabulum 65 is further increased. According to the embodiment shown in FIG. 34*a*, the elongated portion 2201 is placed centered in relation to the collum and caput center axis, such that the an equal portion of the elongated portion is placed in the proximal 1811, distal 1813, frontal 1812 and dorsal 1814 quadrants, respectively.

FIG. 34*b* shows the prosthetic elongated portion 2201, also shown in FIG. 20*b*, when placed in the prosthetic replacement for the acetabulum 65 in a cross-sectional view, and in a side view. In the embodiment of FIG. 34*b*, the prosthetic replacement for the acetabulum surface comprises two rounded extending portions 1823*c,d* clasping the prosthetic spherical portion 45 when implanted in the functional position in the hip joint. The cross section of the prosthetic elongated portion is a more narrow, elliptically shaped cross section which enables further movement of the prosthetic replacement for the acetabulum 65 in the narrow direction of the elliptically shaped elongated portion, where according to this embodiment, the extending portions of the prosthetic acetabulum is placed. The prosthetic replacement for the acetabulum 65 and the prosthetic elongated portion 2201 are oriented in relation to the acetabulum, such that the extending portions 1823*c,d* are placed in the proximal 1811 and distal 1813 quadrant when being in the base position, and the major parts of the elongated portion 2201 are placed in the frontal 1812 and dorsal 1814 quadrants, while only minor parts are placed in the proximal 1811 and distal 1813 quadrants. This configuration enables the prosthetic replacement for the acetabulum 65 to have extending portions 1823*c,d*, and the elongated portion to have a relatively large cross-section without restricting the motion range of the hip joint in excess of the restriction of a natural hip joint, in any direction.

FIG. 34*c* shows the prosthetic elongated portion 2201, also shown in FIG. 20*c*, when placed in the prosthetic replacement for the acetabulum 65 in a cross-sectional view, and in a side view. In the embodiment of FIG. 21*c*, the prosthetic replacement for the acetabulum surface comprises two rounded extending portions 1823*c,d* clasping the prosthetic spherical portion 45 when implanted in the functional position in the hip joint. The two extending portions 1823*c,d* of the prosthetic replacement for the acetabulum 65 has a rounded shape adapted to match corresponding rounded recesses of the elongated portion 2201. The shape of the prosthetic replacement for the acetabulum 65 is so adapted that the prosthetic replacement for the acetabulum 65 can move along a relatively large motion range whilst the extending portions still clasping the prosthetic spherical portion 45. This configuration enables the prosthetic replacement for the acetabulum 65 to have extending portions 1823*c,d*, and the elongated portion to have a relatively large cross-section without restricting the motion range of the hip joint in excess of the restriction of a natural hip joint, in any direction.

FIG. 34*d* shows the prosthetic elongated portion 2201, also shown in FIG. 20*d*, when placed in the prosthetic replacement for the acetabulum 65 in a cross-sectional view, and in a side view. In the embodiment of FIG. 34*d*, the prosthetic replacement for the acetabulum 65 comprises two rounded extending portions 1823*c,d*, and one circumferentially elongated extending portion 1823*b* clasping the prosthetic spherical portion 45 when implanted in the functional position in the hip joint. The two extending portions 1823*c,d* of the prosthetic replacement for the acetabulum 65 has a rounded shape adapted to match corresponding rounded recesses of the elongated portion 2201. The third extending portion 1823*b* is not extending as far as the two 1823*c* and 1823*d*, thus not limiting the motion range as much. The shape of the prosthetic replacement for the acetabulum 65 is so adapted that the prosthetic replacement for the acetabulum 65 can move along a relatively large motion range whilst the extending portions still clasping the prosthetic spherical portion 45. The prosthetic replacement for the acetabulum 65 and the prosthetic elongated portion 2201 are oriented in relation to the acetabulum, such that the extending portions 1823*c,d* are placed in the proximal 1811 and distal 1813 quadrant when being in the base position, where only minor parts of the elongated portion 2201 are placed. A large portion if the elongated portion 2201 is placed in the dorsal quadrant 1814, where no extending portion is present, while a smaller, but still relatively large portion of the elongated portion 2201 is placed in the frontal 1812 quadrants, where a less extending portion is placed. This configuration enables the prosthetic replacement for the acetabulum 65 to have extending portions 1823*c,b,d* in three directions, creating a very stable configuration, whilst still enabling the elongated portion to have a relatively large cross-section without restricting the motion range of the hip joint in far excess of the restriction of a natural hip joint.

Examples of embodiments of different adaptations of the elongated portion, alone, or adaptations in conjunction with corresponding adaptations of the prosthetic replacement for the acetabulum have been shown. The placement of the elongated member in relation to the prosthetic replacement for the acetabulum is critical to the obtained motion range for a prosthetic hip joint comprising a prosthetic replacement for the acetabulum with portions extending beyond the equator of the spherical portion clasped therein. According to some embodiments 1/10 of the cross section of the restricting portion of the elongated member is placed in the proximal and distal quadrants, whereas 9/10 are placed in the frontal and dorsal quadrants, which 9/10 could be equally distributed between the two quadrants, or a major part, such as 6/10 could be placed in the dorsal quadrant and 4/10 could be placed in the frontal quadrants, however it is equally conceivable that it is the other way around depending of the design of the prosthetic replacement for the acetabulum. In embodiments comprising deep recesses or adaptations, or in embodiments where the restricting portion of the elongated portion is placed eccentrically in relation to the collum and caput center axis, as little as 0/10 of the elongated portion could be placed in a particular quadrant and from that the entire range from 1/10-10/10 of the restricting portion of the elongated portion could be placed in any of the quadrants to obtain an advantageous motion range, all depending on the placement of the prosthetic replacement for the acetabulum in relation to the femoral bone, and in particular the extending portions of the prosthetic replacement for the acetabulum when being in the base position.

The medical device according to any of the embodiments could comprise at least one material selected from a group consisting of: polytetrafluoroethylene (PTFE), perfluoroalkoxy (PFA) and fluorinated ethylene propylene (FEP). It is furthermore conceivable that the material comprises a metal alloy, such as cobalt-chromium-molybdenum or titanium or stainless steel, or polyethylene, such as cross-linked polyethylene or gas sterilized polyethylene. The use of ceramic material is also conceivable, in the contacting surfaces or the entire medical device such as zirconium or zirconium dioxide ceramics or alumina ceramics. The part of the medical device in contact with human bone for fixation of the medical device to human bone could comprise a poorhouse structure which could be a porous micro or nano-structure adapted to promote the growth-in of human bone in the medical device for fixating the medical device. The porous structure could be achieved by applying a hydroxy-apatite (HA) coating, or a rough open-pored titanium coating, which could be produced by air plasma spraying, a combination comprising a rough open-pored titanium coating and a HA top layer is also conceivable. The contacting parts could be made of a self lubricated material such as a waxy polymer, such as PTFE, PFA, FEP, PE and UHMWPE, or a powder metallurgy material which could be infused with a lubricant, which preferably is a biocompatible lubricant such as a Hyaluronic acid derivate. It is also conceivable that the material of contacting parts or surfaces of the medical device herein is adapted to be constantly or intermittently lubricated. According to some embodiments the parts or portions of the medical device could comprise a combination of metal materials and/or carbon fibers and/or boron, a combination of metal and plastic materials, a combination of metal and carbon based material, a combination of carbon and plastic based material, a combination of flexible and stiff materials, a combination of elastic and less elastic materials, Corian or acrylic polymers.

Please note that any embodiment or part of embodiment as well as any method or part of method could be combined in any way. All examples herein should be seen as part of the general description and therefore possible to combine in any way in general terms.

According to the above mentioned embodiments the medical device is adapted to be inserted through a hole in the pelvic bone, however it is equally conceivable that the medical device according to any of the embodiment above is adapted to be inserted through a hole in the hip joint capsule or the femoral bone of the human patient.

Please note that any embodiment or part of embodiment as well as any method or part of method could be combined in any way. All examples herein should be seen as part of the general description and therefore possible to combine in any way in general terms.

The invention claimed is:

1. A method for implantation of a medical device in a hip joint of a human patient, a natural hip joint having a ball shaped caput femur integrated with a collum femur having a collum and caput center axis, extending longitudinally along the collum and caput femur, in the center thereof, as the proximal part of a femoral bone with a convex hip joint surface towards the center of the hip joint and a bowl shaped acetabulum as part of a pelvic bone with a concave hip joint surface towards the center of the hip joint, the medical device comprising;

an artificial convex caput femur comprising a convex surface towards the center of the hip joint, an elongated portion connected to a prosthetic spherical portion of said artificial convex caput femur and adapted to be fixated to the pelvic bone of the patient, wherein the artificial convex caput femur has a center point, being the radius center of the prosthetic spherical portion, and wherein said method comprises the steps:

a. fixating the artificial convex caput femur to the pelvic bone of the human patient through said elongated portion fixation to the pelvic bone, b. movably connecting the artificial convex caput femur with a prosthetic artificial acetabulum surface, c. fixating the prosthetic artificial acetabulum surface to the femoral bone of the patient, the prosthetic artificial acetabulum surface comprising at least one extending portion clasping said prosthetic spherical portion, and wherein said elongated portion comprises a restricting portion formed at a distal portion of said elongated portion abutting the prosthetic spherical portion, d. restricting a motion range of said prosthetic artificial acetabulum surface in relation to said artificial convex caput femur with said restricting portion, wherein the distal portion of said elongated portion is rotationally asymmetric with respect to a central axis extending along a longitudinal extension of the elongated portion, due to a form of the restricting portion, wherein said restricting portion is formed such that the restricting portion enables a motion range of said prosthetic artificial acetabulum surface which is larger in some movements and smaller in some movements in relation to said artificial convex caput femur, and e. placing a major portion of said restricting portion of said elongated portion, when implanted, dorsal to a vertical acetabulum plane (PX'Y') coinciding with the collum and caput center axis, to enable an advantageous motion range in relation to said prosthetic artificial acetabulum surface.

2. The method according to claim 1, wherein said major portion of said restricting portion is eccentrically placed by the elongated portion comprising at least one recess to receive a portion of said prosthetic artificial acetabulum surface, when implanted.

3. The method according to claim 2, wherein said recess is placed frontal to a coronal pelvis plane, when implanted.

4. The method according to claim 2, wherein said recess is more than at least one of 2 mm deep, 4 mm deep, 6 mm deep, and 8 mm deep.

5. The method according to claim 2, wherein said recess receives said at least one extending portion when implanted.

6. The method according to claim 1, wherein said elongated portion comprises a bent portion.

7. The method according to claim 1, wherein a cross-section of said restricting portion of said elongated portion, perpendicular to the caput and collum center axis, comprises a first distance and a second distance, wherein a center point of a line of said first distance intersects a center point of a line of said second distance, and wherein said first distance is shorter than said second distance.

8. The method according to claim 1, wherein a cross section of the restricting portion of the elongated portion, perpendicular to the collum and caput center axis, is at least one of placed such that adduction is restricted more degrees than flexion, when implanted, placed such that abduction is restricted more degrees than flexion, when implanted, placed such that adduction is restricted more degrees than extension, when implanted, and placed such that abduction is restricted more degrees than extension, when implanted.

9. The method according to claim 1, wherein:

a) an inner contacting surface of the prosthetic artificial acetabulum surface comprises an equator line, being the largest circular circumference of said inner contacting surface, being a surface adapted to be in contact with said spherical portion, and b) said at least one extending portion passes beyond said equator line, such that an end portion of said inner contacting surface forms a circular extension line having a smaller circumference than said equator line, c) said at least one extending portion circumferentially extends discontinuously along said equator line, such that a portion of said medical device can be placed between said circular extension line and said equator line, and d) wherein said circular extension line is placed proximal to the equator line, when the medical device is implanted.

10. The method according to claim 9, wherein at least a first portion of said prosthetic artificial acetabulum surface is an extending portion, extending beyond said equator line, and at least a second portion of said prosthetic artificial acetabulum surface is a portion not extending beyond said equator line, wherein said first portion circumferentially extends at least in one of, along at least ¼ of said equator line, along at least ⅓ of said equator line, along at least ½ of said equator line, and along at least ⅒ of said equator line.

11. The method according to claim 1, wherein said at least one extending portion extends circumferentially along an equator line, in at least one of the following positions, dorsal to a coronal pelvis plane (PXY) and proximal to a horizontal pelvis (PXZ) plane when being in a base position, dorsal to the coronal pelvis plane (PXY) and distal to the horizontal pelvis (PXZ) plane when being in the base position, extends circumferentially along said equator line dorsal to the coronal pelvis plane (PXY) and proximal to the horizontal pelvis (PXZ) plane, and at least one second extending portion extends in at least one of the following positions;

dorsal to the coronal pelvis plane (PXY) and distal to the horizontal pelvis (PXZ) plane when being in the base position, in a proximal quadrant of the equator line when being in the base position, in a distal quadrant of the equator line when being in the base position, or at least one second extending portion and at least one third extending portion, which extends in at least one of the following positions;

in a distal and proximal quadrant of the equator line when being in the base position, in a proximal and dorsal quadrant of the equator line when being in the base position, in a distal and dorsal quadrant of the equator line when being in the base position, and in a distal, dorsal and proximal quadrant of the equator line when being in the base position.

12. The method according to claim 1, wherein at least a first portion of said prosthetic artificial acetabulum surface is an extending portion, extending beyond an equator line, and at least a second portion of said prosthetic artificial acetabulum surface is a portion not extending beyond said equator line, wherein said second portion circumferentially extends at least in one of, along at least ¼ of said equator line, along at least ⅓ of said equator line, and along at least ½ of said equator line.

13. The method according to claim 1, wherein said at least one extending portion of said prosthetic artificial acetabulum surface is, when implanted in a base position, placed such that the at least one extending portion in relation to the restricting portion enables a motion range such that extension is more restricted than flexion.

14. The method according to claim 1, the method further comprising the steps of:

i. cutting the skin of the patient, and ii. dissecting an area of the pelvic bone.

15. The method according to claim 1, wherein the restricting portion of said elongated portion is placed, according to one of the placements selected from the list consisting of:

such that adduction is restricted more degrees than flexion, such that abduction is restricted more degrees than flexion, such that adduction is restricted more degrees than extension, and such that abduction is restricted more degrees than extension.

16. A method for implantation of a medical device in a hip joint of a human patient, the medical device comprising an elongated portion connected to a prosthetic spherical portion, said elongated portion comprising a restricting portion formed at a distal portion of said elongated portion abutting the prosthetic spherical portion, wherein the distal portion of said elongated portion is rotationally asymmetric with respect to a central axis extending along a longitudinal extension of the elongated portion wherein said method comprises the steps:

a. fixating the elongated portion to a pelvic bone of the patient, b. fixating an artificial acetabulum surface to a femoral bone of the patient, c. movably connecting the prosthetic spherical portion to the artificial acetabulum surface by clasping said prosthetic spherical portion with at least one extending portion of the artificial acetabulum surface, d. restricting a motion range of said artificial acetabulum surface in relation to said prosthetic spherical portion, e. placing a major portion of said restricting portion of said elongated portion, when implanted, dorsal to a vertical acetabulum plane (PX'Y') coinciding with a collum and caput center axis, to enable an advantageous motion range of said relation to said prosthetic spherical portion.

* * * * *